Figure 1:
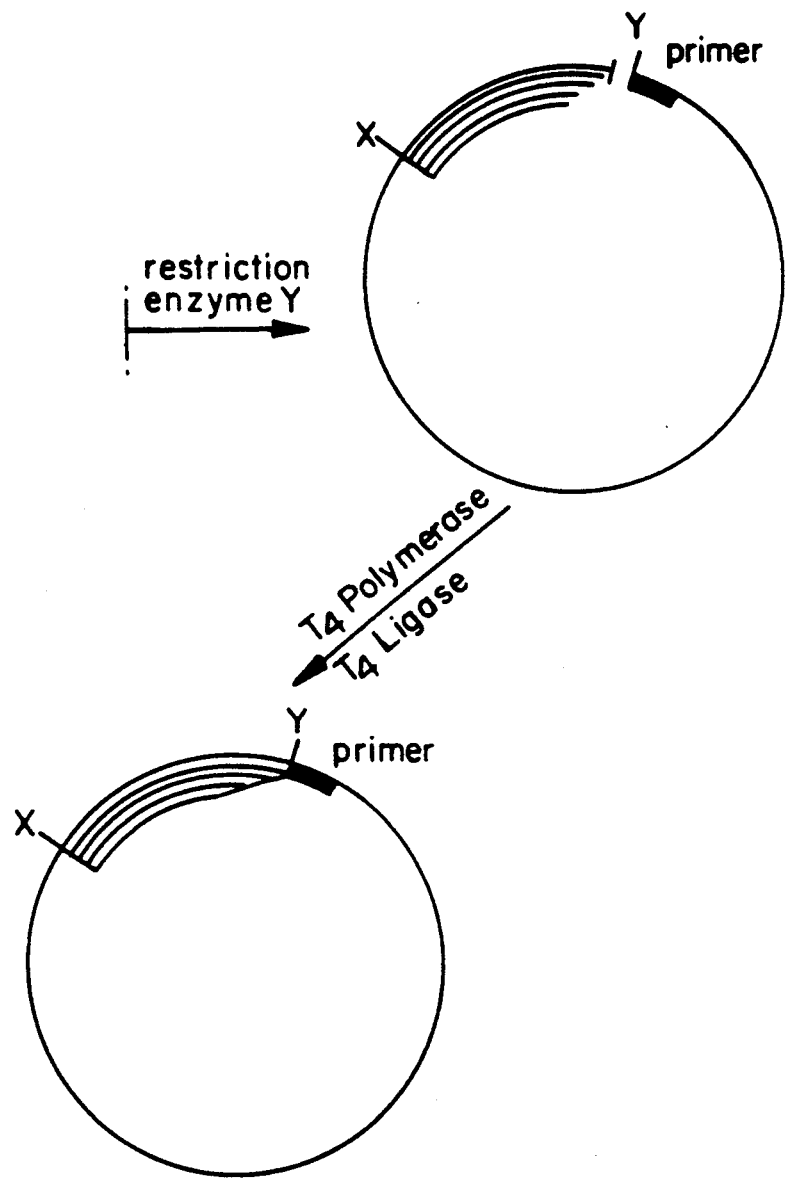

United States Patent [19]
Ledeboer et al.

[11] Patent Number: 5,240,838
[45] Date of Patent: Aug. 31, 1993

[54] REGULATORY SEQUENCES OF ALCOHOL OXIDASE (MOX) AND DIHYDROXYACETONESYNTHASE (DAS) OF HANSENULA POLYMORPHA

[75] Inventors: Adrianus M. Ledeboer, Rotterdam; Jan Maat, Monster; Cornelis T. Verrips, Maasslius; Christiaan Visser, Capelle a/d IJssel, all of Netherlands; Zbigniew A. Janowicz, Erkrath-Unterfeldhaus; Cornelis P. Hollenberg, Dusseldorf, both of Fed. Rep. of Germany

[73] Assignee: Internationale Otrool Maatschappij "Octropa" B.V., Rotterdam, Netherlands

[21] Appl. No.: 587,555

[22] Filed: Sep. 24, 1990

Related U.S. Application Data

[63] Continuation of Ser. No. 300,211, Jan. 23, 1989, abandoned, which is a continuation of Ser. No. 759,315, Jul. 26, 1985, abandoned.

[30] Foreign Application Priority Data

Jul. 27, 1984 [EP] European Pat. Off. ......... 84 201114
Feb. 7, 1985 [GB] United Kingdom ................. 8503160

[51] Int. Cl.⁵ .................. C12N 1/19; C12N 15/81; C12N 15/11
[52] U.S. Cl. .................. 435/254.2; 435/254.21; 435/69.1; 435/320.1; 536/24.1; 935/6; 935/37; 935/69
[58] Field of Search .............. 536/27; 435/69.1, 172.3, 435/320.1, 255, 256; 935/6, 9, 14, 37, 69

[56] References Cited

U.S. PATENT DOCUMENTS

| | | | |
|---|---|---|---|
| 4,438,032 | 3/1984 | Golde et al. | 435/255 |
| 4,628,033 | 12/1986 | DeZeeuw | 435/172.3 X |
| 4,657,857 | 4/1987 | Edens et al. | 435/69.1 |
| 4,808,537 | 2/1989 | Stroman et al. | 435/6 |

FOREIGN PATENT DOCUMENTS

| | | |
|---|---|---|
| 0066857 | 6/1982 | European Pat. Off. |
| 0066994 | 12/1982 | European Pat. Off. |
| 0086139 | 8/1983 | European Pat. Off. |
| 0098533 | 1/1984 | European Pat. Off. |
| 0103887 | 3/1984 | European Pat. Off. |

OTHER PUBLICATIONS

Gleeson, M. et al., *J. Gen. Micro*, vol. 132, p. 3459–3465, 1986.
Janowicz, Z. et al, *Nuc. Acids Res*, vol. 13, pp. 3043–3062, May, 1985.
Ledeboer, A. et al, *Nuc Acids Res*, vol. 13, pp. 3063–3082, May, 1985.
Roggenkamp, R. et al, *Mol. Gen Genet*, vol. 202, pp. 302–308, 1986.

(List continued on next page.)

*Primary Examiner*—Richard A. Schwartz
*Assistant Examiner*—Mary E. Mosher
*Attorney, Agent, or Firm*—Cushman, Darby & Cushman

[57] ABSTRACT

The structural genes and their regulatory DNA sequences of an alcohol oxidase (MOX) and a dihydroxyacetone synthase (DHAS) of *Hansenula polymorpha* have been isolated and the nucleotide sequences determined. The invention relates to the use of the MOX gene, as well as the use of the regulatory DNA sequences of MOX and/or DAS in combination with the MOX gene, optionally after modification thereof, or other oxidase genes, or other genes, to produce engineered microorganisms, in particular yeasts. Said engineered microorganisms can produce oxidases or other enzymes in yields that allow industrial application on a large scale. Moreover, said engineered microorganisms can produce oxidases having improved properties with respect to their application in oxidation reactions and/or in bleaching and detergent products.

4 Claims, 49 Drawing Sheets

OTHER PUBLICATIONS

Hitzeman, R., et al, *Nature*, vol. 293, p. 717-722, 1981.

Urdea, M. et al, *Proc. Nat. Acad Sci*, vol. 80, pp. 7461-7465, 1983.

Murooka, Y. et al, *Agric Biol Chem*, vol. 47(8), pp. 1807-1815, 1983.

Ronchi, S. et al, *J. Biol. Chem*, vol. 257, pp. 8824-8834, 1982.

Roggenkamp, R. et al, *Mol. Gen. Genet.* vol. 194, pp. 489-493, May, 1984.

Sakaguchi, J. et al, *Proc. Nat. Acad. Sci*, vol. 79, pp. 7819-7823, 1982.

Das, S. et al, *Current Genetics*, vol. 6, pp. 123-128, 1982.

Tikhomiroua, L. et al, *Current Genetics*, vol. 10, 741-747, 1986.

Feb Letters, vol. 126, No. 2, Apr. 1981, Elsevier/North-Holland Biomedical Press, Geissler et al, "Yeast Methanol Oxidases: An Unusual Type of Flavorprotein".

Tikhamirova, L. P. et al. 1985. *Doklady AkademiiNank SSSR* 1985, v. 282, No. 3, pp. 741-743.

Chemical Abstracts, vol. 99, No. 1, July 1983, p. 227, ref No. 2206q.

Chemical Abstracts, vol. 94, No. 21, May 1981, p. 375, ref. No. 170905G.

Journal of Biochemistry, vol. 91, No. 4, Apr. 1982 pp. 1205-1212.

Chemical Abstracts, vol. 96, No. 13, Mar. 29, 1982, p. 560, ref No. 102478m.

Chemical Abstracts, vol. 95, No. 5, Aug. 3, 1981, p. 291, ref. No. 37855v.

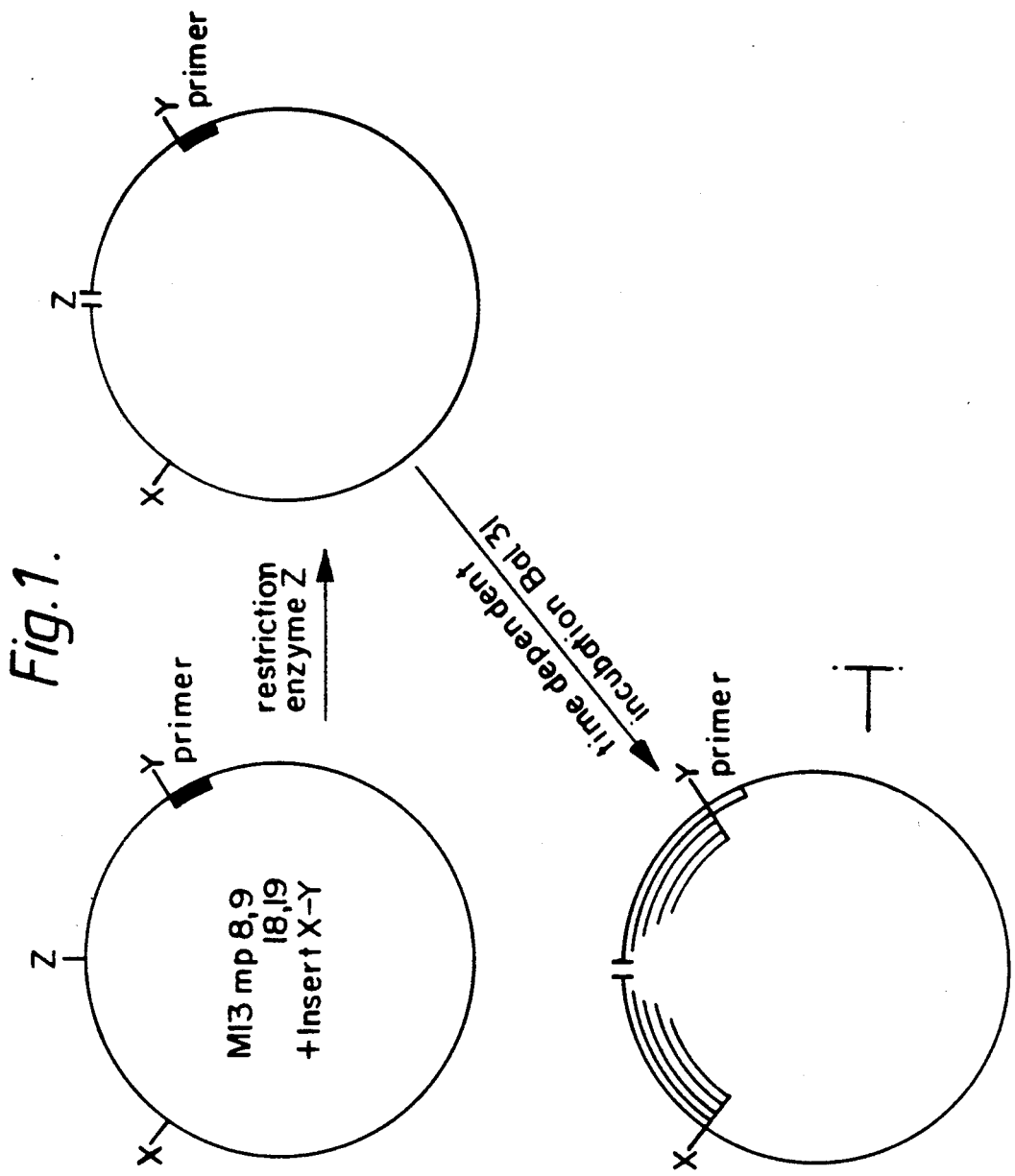

1 2 3 4 5 6 7 8 9 10 11 12 13

1  2 3 4 5 6 7  8

Fig. 7

NH2-Ala-Ile-Pro-Asp-Glu-Phe-Asp-Ile-Ile-Val-Val-Gly-

CCA GAC GAA TTC GA
CCA GAT GAA TTC GA

-Gly-Gly- * -Thr-Gly-Cys-Cys-Ile-Ala-Gly- * -Leu-
-Ala-Asn-Leu-Asp-Asp-Gln-Asn-Leu

Fig. 10A

```
GTCGACGCGG AGAACGATCT CCTCGAGCTG CTCGCGGATC AGCTTGTGGC CCGGTAATGG
                -1501
AACCAGGCCG ACGGACGCT CCTTGCGGAC CACGGTGGCT GGCGAGCCCA GTTTGTGAAC
-1451                                                          -1401
GAGGTCGTTT AGAACGTCCT CGGCAAAGTC CAGTGTCAGA TGAATGTCCT CCTCGGACCA
                                                 -1351
ATTCAGCATG TTCTCGAGCA GCCATCTGTC TTTGGAGTAG AAGCGTAATC TCTGCTCCTC
                                 -1301
GTTACTGTAC CGGAAGAGGT GCCCCCATA ATGAACAGGT TCTCTTTCTG
GTGCCCTGTG AGCAGCGGGG ACGTCTGGAC GGCGTCGATG AGGCCCTTGA GGCGCTCGTA
-1201
GTACTTGTTC CGTCGCTGTA GCCGGCCGCG GTGACGATAC CCACATAGAG GTCCTTGGCC
-1151                                                          -1101
ATTAGTTTGA TGAGGTGGGG CAGGATGGGC GACTCGGCAT CGAAATTTTT GCCGTCGTCG
TACAGTGTGA TGTCACCATC GAATGTAATG AGCTGCCAGCT TGCGATCTCG GATGGTTTTG
                                         -1001
GAATGGAAGA ACCCCGACAT CTCCAACAGC TGGGCCCTGT TGAGAATGAG CCGGACGTCG
                                 -951
TTGAACGAGG GGCCCACAAG CCGGGCGTTTG CTGATGCCCC GCCGCTCGTC CTCGATGTAG
AAGGCCTTTT CCAGAGGCAG TCTCGTGAAG AAGCTGCCAA CGCTCGGAAC CAGCTGCACG
-851                                                           -801
AGCCGAGACA ATTCGGGGGT GCCGGCTTTG GTCATTTCAA TCTTGTCGTC GATGAGGAGT
                                                 -751
TCGAGGTCGT GGAAGATTTC CGGGTAGCCGG CGTTTTGCCT CAGAGTTTAC CATGAGGTCG
                                 -701
```

Fig. 10B

```
TCCACTGCAG AGATGCCGTT GCTCTTCACC GCGTACAGGA CGAACGGCCT GGCCAGCAGG
                                                                    -651
CCCTTGATCC ATTCTATGAG GCCATCTCGA CGGTGTTCCT TGAGTGCGTA CTCCACTCTG
                      -601
TAGCCACTGG ACATCTCGAG ACTGGGCTTG CTGTGCTCGA TGCACCAATT AATTGTTGCC
-551                                                                -501
GCATGCCATC TTGCACCGCA AGTTTTTAAA ACCCACTCGC TTTAGCCCGTC GCGTAAAACT
                                            -451
TGTGAATCTG GCAACTGAGG GGGTTCTGCA GCCGCAACCG AACTTTTCGC TTCGAGGACG
                                 -401
CAGCTGGATG CGTGTCATGT AGGCTCTGTT TGCTGGGCGTA GCCTACAACG TGACCTTGCC
                      -351
TAACCCGGACG GCGCTACCCA CTGCTGTCTG TGCCTGCTAC CAGAAAATCA CCAGAGCAGC
-301
AGAGGGCCCGA TGTGGCAACT GCTGGGGTGT CGGACAGGCT GTTCTCCAC AGTGCAAATG
                                                                    -201
CGGGTGAACC GGCCAGAAAG TAAATTCTTA TGCTACCCGTG CAGCGGACTCC GACATCCCCA
                                                         -151
GTTTTTGCCC TACTTGATCA CAGATGGGGT CAGCCCTGCC GCTAAGTGTA CCCAACCGTC
                                            -101
CCCACACGGT CCATCTATAA ATACTGCTGC CAGTGCACGG TGCTGACATC AATCTAAAGT
                      -51

1                                                              15
    MET ALA ILE PRO ASP GLU PHE ASP ILE ILE VAL VAL GLY GLY SER THR
    ATG GCC ATT CCT GAC GAA TTC GAT ATC ATT GTT GTT GGT GGA GGT TCC ACC
-11
        20                              25                              30                              35
    GLY CYS ILE ALA GLY ARG LEU ALA ASN LEU ASP GLN ASN LEU THR VAL ALA LEU
    GGC TGC ATT GCG GGC AGA CTC GCA AAC CTC GAC CAA AAC CTC ACA GTT GCC CTG
        40                              45                              50                              55
```

Fig. 10C

| | | | | | | | | | |
|---|---|---|---|---|---|---|---|---|---|
| ILE ATC | GLU GAG | GLY GGT 60 | ASN AAC | ASN AAC | PRO CCT | TRP TGG | VAL GTC 70 | TYR TAC | LEU CTT | PRO CCC | GLY GGA | VAL GTG 75 | TYR TAT | PRO CCT |
| ARG AGA | ASN AAC | MET ATG 80 | ASP GAC | LYS AAG | THR ACG | ALA GCC | THR ACC | PHE TTC | SER TCC | ARG AGA | PRO CCA | SER TCG 85 | LYS AAG | ALA GCT |
| LEU CTG | ASN AAC | GLY GGC 100 | ARG AGA | ALA GCG | ILE ATC | VAL GTT 105 | PRO CCT | CYS TGC | LEU CTT | GLY GGA | GLY GGC | SER TCG 115 | SER TCG | ILE ATC |
| ASN AAC | PHE TTT | LEU CTG 120 | MET ATG | TYR TAC | THR ACC | ARG AGA | ALA GCC 125 | SER TCT | ALA GCT | TYR TAC | ASP GAC | TRP TGG | GLU GAG 135 | GLY GGA |
| TRP TGG | SER AGC | THR ACC 140 | ASP GAC | GLU GAG | LEU TTG | PRO CCT 145 | LYS AAA | ILE ATC | LYS AAA | GLU GAA | THR ACT | TYR TAC | GLN CAG | PRO CCT 155 | CYS TGC |
| ASN AAC | ASN AAC | ARG AGA 160 | ASP GAT | PHE TTT | HIS CAC | GLY GGC 165 | PHE TTT | ASP GAC | GLY GGA | PRO CCT | VAL GTT 175 | ASN AAC | TYR TAC | THR ACG |
| TYR TAT | THR ACG | PRO CCT 180 | CYS TGC | ASP GAC | PHE TTC | LYS AAG 185 | THR ACA | ARG AGA | GLU GAG | ALA GCA | GLU GAG | SER TCG 190 | HIS CAC | VAL GTG | ASP GAC |
| ASP GAC | LEU CTG | GLU GAG 200 | ARG AGA | PHE TTC | LYS AAG | THR ACA 205 | HIS CAT | GLY GGT | ALA GCA | TYR TAC | HIS CAC 210 | PRO CCA | THR ACT | MET ATG | ARG AGA | ASN AAC |
| ASP GAC | LEU CTG | GLY GGC 220 | ARG AGA | ARG AGA | SER TCG | ASP GAT 225 | SER TCT | ALA GCC | HIS CAC | ALA GCA | TYR TAC | VAL GTC 230 | ALA GCC | ARG AGA | ASN AAC | LYS AAG |
| GLN CAG | SER AGC | LEU CTG 240 | PHE TTC | LEU CTC | ILE ATC | THR ACC 245 | SER TCG | LYS AAG | CYS TGT | ASP GAC | LYS AAG 250 | VAL GTG | ILE ATC | GLU GAG | ASP GAC | GLY GGC | LYS AAG 255 |
| ALA | VAL | ALA | VAL | ARG | THR | VAL | PRO | MET | LYS | PRO | LEU | ASN | PRO | LYS | LYS | PRO | VAL | SER | ARG |

Fig. 10D

```
GCT GTG GCC GTG AGA ACA GTG CCA ATG AAG CCT CTG AAC CCT AAG AAG CCT GTG TCC AGA
        260                 265                 270                 275
THR PHE ARG ALA ARG LYS GLN ILE VAL ILE SER CYS GLY THR ILE SER SER PRO LEU VAL
ACC TTC AGA GCC AGA AAG CAG ATT GTG ATC TCC TGC GGA ACC ATC TCG TCT CCT CTG GTG
        280                 285                 290                 295
LEU GLN ARG SER GLY ILE GLY ALA ALA HIS HIS LEU ARG SER VAL GLY VAL LYS PRO ILE
CTC CAG AGA TCT GGT ATT GGT GCA GCT CAC CAC TTG AGA TCC GTG GGG GTC AAG CCA ATC
        300                 305                 310                 315
VAL ASP LEU PRO GLY VAL GLY GLU ASN PHE GLN ASP HIS TYR CYS PHE PHE THR PRO TYR
GTC GAC CTG CCA GGT GTG GGT GAG AAT TTC CAG GAC CAC TAC TGT TTC TTC ACT CCA TAC
        320                 325                 330                 335
TYR VAL LYS PRO ASP VAL PRO THR PHE ASP ASP PHE VAL ARG GLY ASP PRO VAL ALA GLN
TAC GTC AAG CCT GAC GTT CCT ACG TTC GAC GAC TTT GTC AGG GGC GAC CCA GTT GCC CAG
        340                 345                 350                 355
LYS ALA ALA PHE ASP GLN TRP TYR SER ASN LYS ASP GLY PRO LEU THR THR ASN GLY ILE
AAG GCC GCT TTC GAC CAG TGG TAC TCC AAC AAG GAC GGT CCA TTG ACC ACC AAC GGT ATT
        360                 365                 370                 375
GLU ALA GLY VAL LYS ILE ARG PRO THR GLU GLU GLU LEU ALA THR ALA ASP GLU ASP PHE
GAA GCC GGA GTC AAG ATC AGA CCT ACC GAA GAG GAG CTG GCT ACC GCG GAC GAG GAC TTC
        380                 385                 390                 395
ARG ARG GLY TYR ALA GLU TYR PHE GLU ASN LYS PRO ASP LYS PRO LEU MET HIS TYR SER
AGA CGC GGC TAC GCA GAG TAC TTC GAG AAC AAG CCA GAC AAG CCT CTG ATG CAC TAC TCT
        400                 405                 410                 415
VAL ILE SER GLY PHE PHE GLY ASP HIS THR LYS ILE PRO ASN GLY LYS PHE MET THR MET
GTC ATC TCC GGC TTC TTT GGA GAC CAC ACC AAG ATT CCT AAC GGC AAG TTC ATG ACC ATG
        420                 425                 430                 435
PHE HIS PHE LEU GLU TYR PRO PHE SER ARG GLY PHE VAL ARG ILE THR SER ALA ASN PRO
TTC CAC TTC CTG GAG TAT CCA TTC TCC AGA GGA TTT GTT AGA ATC ACC TCG GCA AAC CCA
        440                 445                 450                 455
```

Fig. 10E

```
                                            440                 445                 450                                 455
TYR ASP ALA PRO ASP PHE ASP GLY PHE LEU ASN ASP GLU ARG ASP LEU PRO MET
TAC GAC GCT CCT GAC TTC GAT GGC TTC CTC AAT GAC GAA AGA GAC CTG CCT ATG
            460                 465                 470                                 475

VAL TRP ALA TYR LYS LYS SER ARG GLU THR ALA ARG ALA SER PHE ALA GLY GLU
GTC TGG GCA TAC AAG AAG TCC AGA GAG ACG GCC AGC TTT GCA GGA GAG
            480                 485                 490                                 495

VAL THR SER HIS HIS PRO LEU PHE LYS VAL ASP SER ARG ALA ARG ASP LEU ASP
GTC ACC TCG CAC CCA TTG AAG GTT GAC TCG AGA GCC AGA GAC CTG GAC
            500                 505                 510                                 515

LEU GLU THR CYS SER ALA TYR ALA GLY PRO LYS HIS LEU THR ALA ASN LEU TYR HIS GLY
CTC GAG ACA TGC AGT GCA TAT GCC GGT CCT AAG CAC CTC ACT GCC AAC CTG TAC CAC GGC
            520                 525                 530                                 535

SER TRP THR VAL PRO ILE ASP SER ASN LYS PRO THR ALA PHE HIS VAL THR SER ASN
TCG TGG ACC GTT CCT ATC GAC AAC AAG CCT ACG GCC TTC CAC GTG ACC TCC AAC
            540                 545                 550                                 555

GLN VAL GLN LEU HIS SER ASP ILE GLU TYR THR GLU GLY ALA GLU VAL ASN
CAA GTC CAA CTG CAC TCC GAC ATC GAG TAC ACC GAG GAG GCC ATC AAC
            560                 565                 570                                 575

TYR ILE LYS GLU HIS THR GLU THR TRP HIS CYS LEU GLY THR CYS SER MET ALA PRO
TAC ATT AAG GAA CAC ACC GAG ACT TGG CAC TGT CTG GGT ACC TGC TCG ATG GCC CCA
            580                 585                 590                                 595

ARG GLU GLY SER LYS ILE ALA PRO LYS GLY VAL LEU ASP ALA ARG LEU ASN VAL TYR
AGA GAG AGT AAG ATT GCT CCT AAG GGA GTC TTG GAC GCC AGA CTG AAC GTT TAC
            600                 605                 610                                 615

GLY VAL GLN ASN LEU LYS VAL ALA ASP LEU SER VAL CYS PRO ASP ASN VAL GLY CYS ASN
```

Fig. 10F

```
GGA GTC CAG AAC CTC AAG GTT GCG GAC CTT TCT GTT TGT CCC GAC AAC GTT GGA TGC AAC
    620                             625                             630                             635
THR TYR SER THR ALA LEU THR ILE GLY GLU LYS ALA THR LEU VAL ALA GLU ASP LEU
ACC TAC TCT ACT GCA TTG ACC ATC GGT GAG AAG GCT ACT CTT GTT GCT GAA GAT CTT
            640                             645                             650                             655
GLY TYR SER GLY SER ASP LEU ASP MET THR ILE PRO ASN PHE ARG LEU GLY THR TYR GLU
GGC TAC TCA GGC TCC GAC CTG GAC ATG ACG ATT CCA AAC TTC AGA CTC GGA ACT TAC GAG
            660
GLU THR GLY LEU ALA ARG PHE ***
GAG ACC GGA CTT GCC AGA TTC TAA GGAG ACGTGGAAGC ACATACCGCT TTTGAGAAGC
                                              2000
GTGTTTGAAA ATAGTTCTTT TTCTGGTTTA TATCGTTTAT GAAGTGATGA GATGAAAAGC
                                     2050
TGAAATAGCG AGTATAGGAA AATTTAATGA AAATTAAATT AAATATTTTC TTAGGCTATT
                                2100
AGTCACCTTC AAAATGCCGG CCGCTTCTAA GAACGTTGTC ATGATCGACA ACTACGACTC
           2150                                                                    2200
GTTTACCTGG AACCTGTACC AGTACCTGTG TCAGGAGGGA GCAGCTCAAG AGGTTTTCAG
                                                                   2250
GAACGATCAG ATCACCATTC CGGAGATTGA GAACAGACTC GGGAATATCT TGGTGATATC
                                              2300
CCCTGGTCCT GGCCATCCAA GAACAGACTC CGGGAATATCT CGGGACGTGA TCAGCCATTT
                                              2350
TAAAGGCAAG ATTCCTGTCT TTGGTGTCTG TATGGGCCAG CAGTGTATCT TCCAGGAGTT
           2400
TGGCCGAGAC GTCGAGTATG CGGGCCAGAT TGTCCATGGA AAAACGTCCA CTGTTAAGCA
           2450                                                                    2500
```

Fig. 10G

```
CGACAACAAG GGAATGTTCA AAAACGTTCC GCAAGATGTT GCTGTCACCA GATACCACTC
GCTGGCCCGA ACGCTCAAGT CGCTTCCGGA CTGTCTAGAG ATCACTGCTC GCACAGACAA
                                   2600
CGGGATCATT ATGGGTGTGA GACACAAGAA GTACACCATC GAGGGCCTCC AGTTTCATCC
                       2650
AGAGAGCATT CTGACCGAGG AGGGCCATCT GATGATCCAG AATATCCTCA ACGTTTCCGG
                 2700
TGGTTACTGG GAGGAAAATG CCAACGGCGC GGCTCAGAGA AAGGAAAGCA TATTGGAGAA
 2750                                                         2800
AATATACGCG CAGAGACGAA AAGACTACGA GTTTGAGATG AACAGACCGG GGCGGCAGATT
TGCTGATCTA GAACTGTACT TGTCCATGGG ACTGCACCCG CGCTAATCAA TTTTTACGAC
                                  2900                        
AGATTGGAGC AGAACATCAG CGCCGGCAAG GTTGCAATTC TCAGCGAAAT CAAGAGAGCG
TCGCCTTCTA AAGGCGTCAT CGACGGAGAC GCTAACGCTG CCAAACAGGC CCTCAACTAC
           3000
GCCAAGGCTG GAGTTGCCAC AATTTCTGTT TTGACCGAGC CAACCTGGTT TAAAGGAAAT
 3050                                                         3100
ATCCAGGACC TGGAGGTGGC CAGAAAAGCC ATTGACTCTG TGCCCAATAG ACCGTGTATT
                                                 3150
TTGCGGAAGC AGTTTATCTT CAACAAGTAC CAAATTCTAG AGGCCCGACT CGGCGGGAGCA
                                  3200
GACACGGGTC TGCTGATTGT CAAGATGCTG AGCTC
                        3250
```

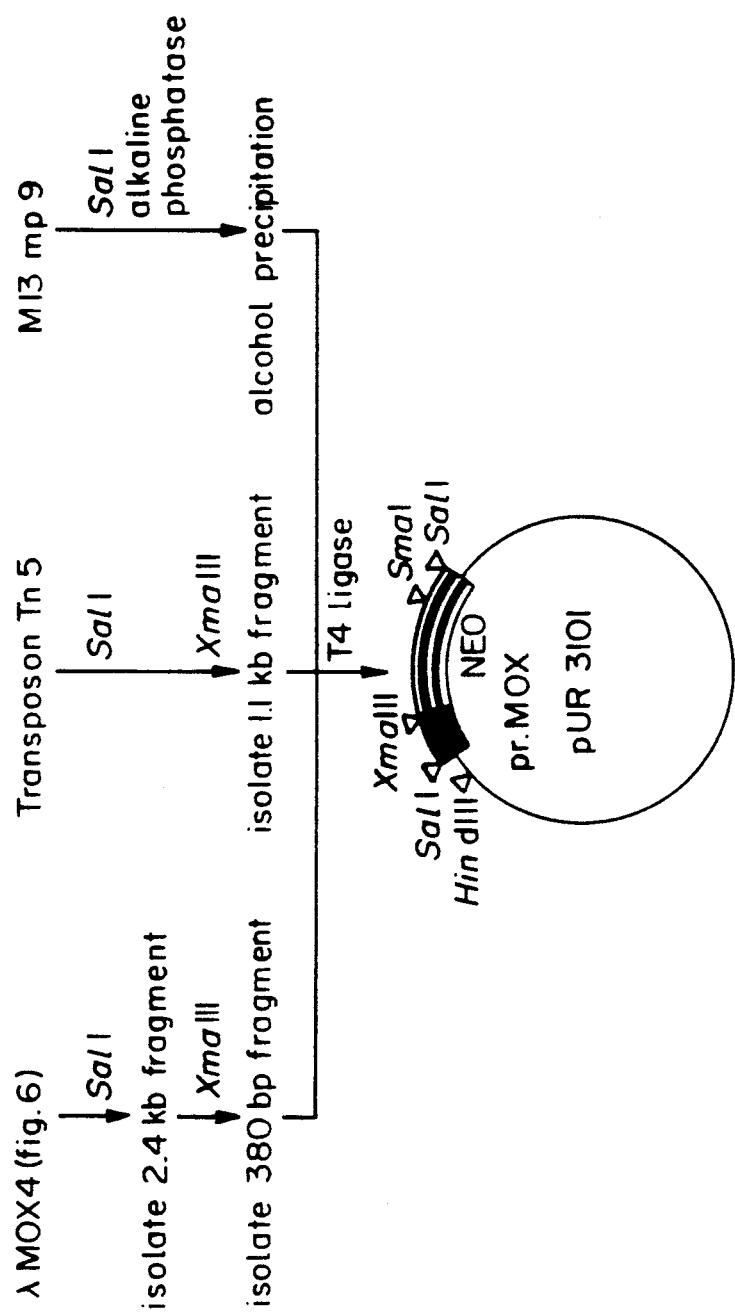
Fig. IIA

Fig. 11B

Promoter MOX-Neomycinphosphotransferase adaptor fragments

NEO3 5'CGGTGGTGACATCAATCTAAAGTACAAA 3'

NEO6 5'TCATTTTGTTTTTGTACTTTAGATTGATGTCACCACCGTGCA 3'

NEO7 5'AACAAAATGATTGAACAAGATGGATTGCACCGCAGGTTCTCCGGCCCGCTTG 3'

NEO8 5'AATTCAAGCGGGCCGGAGAACCTGCGGTGCAATCCATCTTGTTCAA 3'

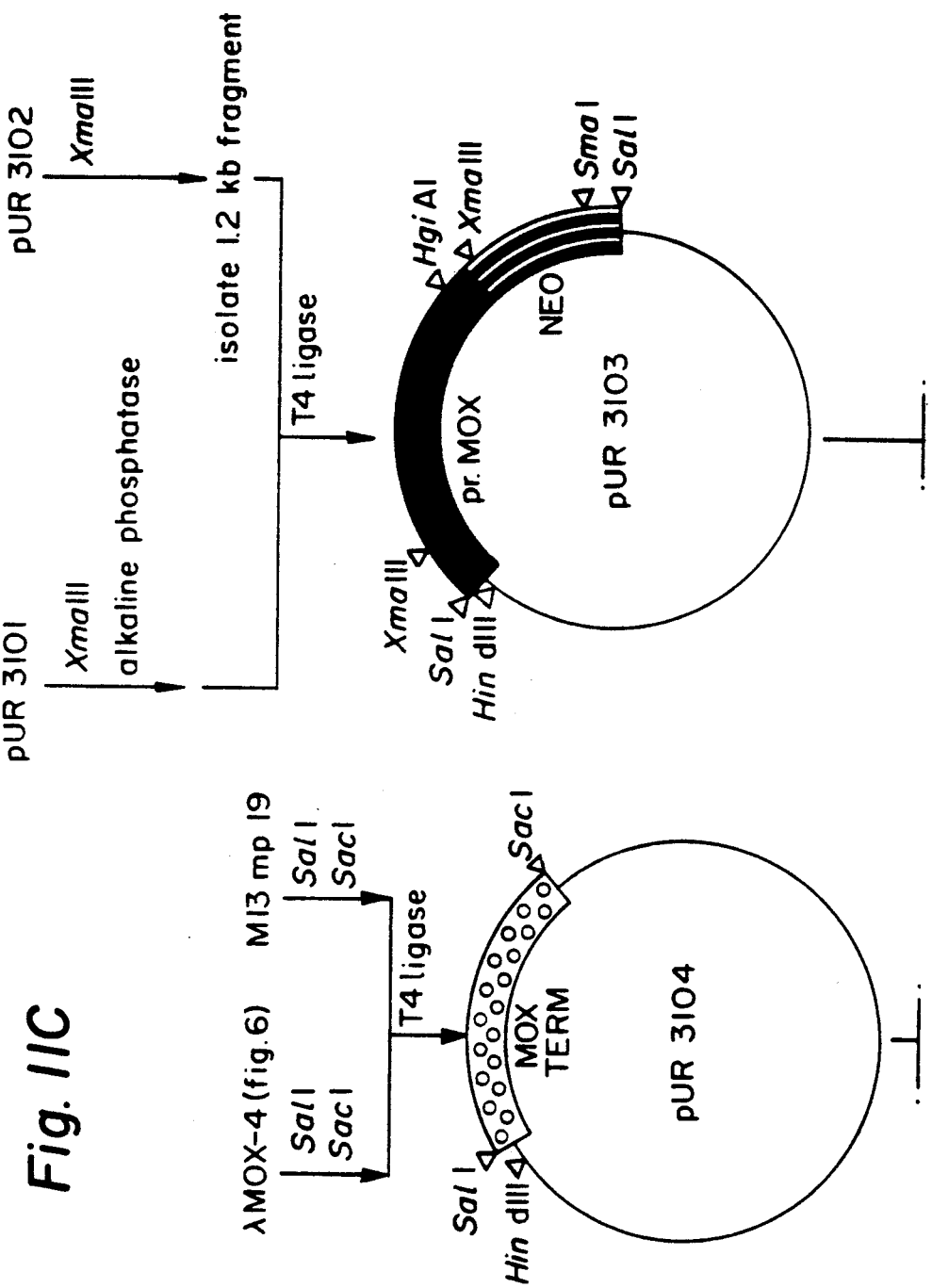
Fig. IIC

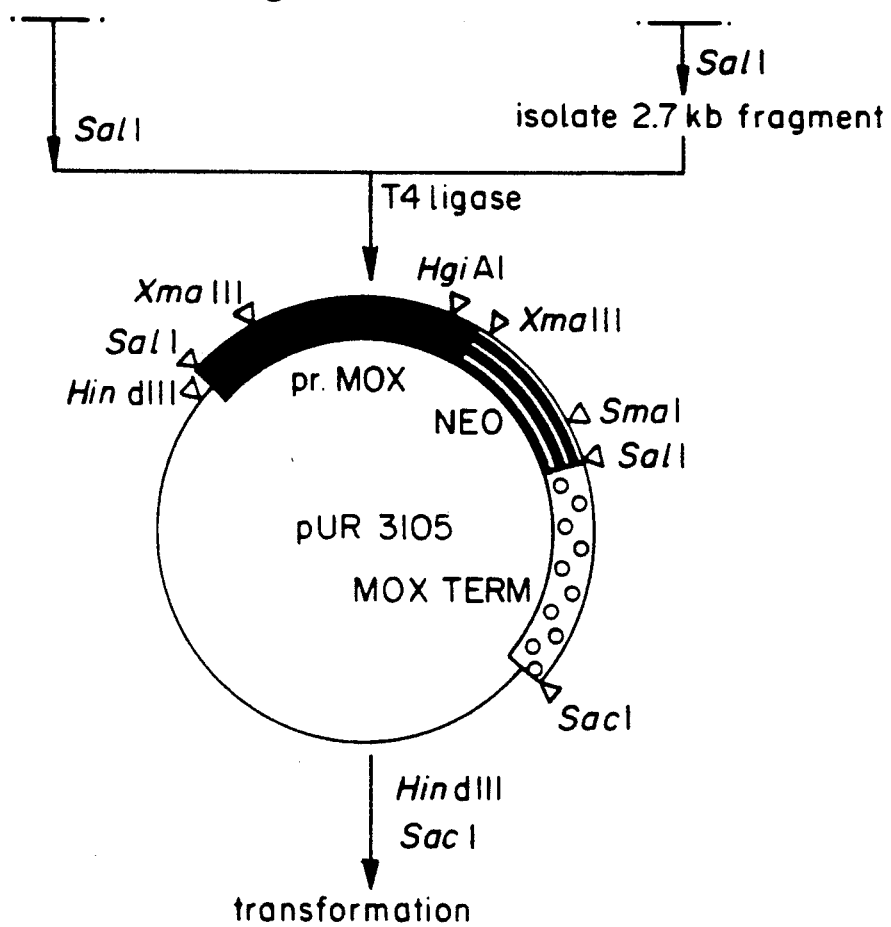
Fig. IIC(Cont.)

Fig. 12A

```
<~~~~~~~~~~ PROMOTER MOX/AAO ADAPTOR~~~~~~~~~~~~~~~~~~~>>
    -34                                                  1
      CGGTGG TGACATCAAT CTAAAGTACA AAAACAAAAT GAGAGTTGTC GTTATTGGTG
      ACCTGCCACC ACTGTAGTTA GATTTCATGT TTTGTTTTA CTCTCAACAG CAATAACCAC
      HgiaI                                    Met
<<~~~~~~~~~~~~~~>
                                62
CCGGTGTCAT CGGTCTGTCG ACCGCCCTGT GTATCCACGA GAGATACCAC TCCCGTTCTGC
GGCCACAGTA GCCAGACAGC TGGCGGGACA CATAGGTGCT CTCTATGGTG AGGCAAGACG
           SalI 122
AGCCTCTGGA CGTTAAGGTC TACCCCGACA GATTCACCCC TTTCACCACC ACCGACGTTG
TCGGAGACCT GCAATTCCAG ATGCGGCTGT CTAAGTGGGG AAAGTGGTGG TGGCTGCAAC 182
CCGCCGGTCT GTGGCAGCCT TACACCTCCG AGCCTTCCAA CCCTCAGGAG GCCAACTGGA
GGCGGCCAGA CACCGTCGGA ATGTGGAGGC TCGGAAGGTT GGGAGTCCTC CGGTTGACCT 242
ACCAGCAGAC CTTCAACTAC CTCCCTCTCCC ACATCGGTTC GCCTAACGCC GCCAACATGG
TGGTCGTCTG GAAGTTGATG GAGGAGAGGG TGTAGCCAAG CGGATTGCGG CGGTTGTACC 302
GTCTGACCCC TGTCTCCGGGT TACAACCTGT TCAGAGAGGC CGTTCCTGAC CCTTACTGGA
CAGACTGGGG ACAGAGCCCA ATGTTGGACA AGTCTCTCCG GCAAGGACTG GGAATGACCT
```

Fig. 12B

```
                                                  362
AGGACATGGT CCTCGGTTTC AGAAAGCTTA CCCCTAGAGA GCTGGACATG TTCCCTGACT
TCCTGTACCA GGAGCCAAAG TCTTTCGAAT GGGGATCTCT CGACCTGTAC AAGGGACTGA
                                HindIII 422
ACAGATACGG TTGGTTCAAC ACCTCCCTGA TCCTGGAGGG TAGAAAGTAC CTGCAGTGGC
TGTCTATGCC AACCAAGTTG TGGAGGGACT AGGACCTCCC ATCTTTCATG GACGTCACCG 482
TGACCGAGAG ACTGACCGAG AGAGCTGTTA AGTTCTTCCT GAGAAAGGTC GAGTCCTTCG
ACTGGCTCTC TGACTGGCTC TCTCCACAAT TCAAGAAGGA CTCTTTCCAG CTCAGGAAGC 542
AGGAGGTTGC CAGAGGTGGT GCCGACGTCA TCATCATGTG TACCCGGTGTC TGGGCCCGTG
TCCTCCAACG GTCTCCACCA CGGCTGCAGT AGTAGTACAC ATGGCCACAG ACCCGGCCAC 602
TCCTGCAGCC TGACCCCTCTG CTGCAGCCCCG GGAGAGGTCA GATCATTAAG GTTGACGCCC
AGGACGTCGG ACTGGGAGAC GACGTCGGGC CCTCTCCAGT CTAGTAATTC CAACTGCGGG
                              XmaI 662
CATGGCCTGAA GAACTTCATC ATTACCCACG ACCTGGAGAG AGGTATCTAC AACTCCCCTT
GTACCGGACTT CTTGAAGTAG TAATGGGTGC TGGACCTCTC TCCATAGATG TTGAGGGGAA 722
ACATTATCCC TGGTCTGCAG GCCGTCACCC TGGTGGTAC CTTCCAGGTC GGTAACTGGA
TGTAATAGGG ACCAGACGTC CGGCAGTGGG ACCCACCATG GAAGGTCCAG CCATTGACCT
                                    KpnI
```

Fig. 12C

```
                                                        782
ACGAGATCAA  CAACATCCAG  GACCACAACA  CCATCTGGGA  GGGTTGTTGT  AGACTGGAGC
TGCTCTAGTT  GTTGTAGGTC  CTGGTGTTGT  GGTAGACCCT  CCCAACAACA  TCTGACCTCG

842
CTACCCTGAA  GGACGCCAAG  ATCGTTGGTC  AGTACACCGG  TTTCAGACCT  GTTAGACCTC
GATGGGACTT  CCTGCGGGTTC TAGCAACCAC  TCATGTGGCC  AAAGTCTGGA  CAATCTGGAG

902
AGGTCAGACT  GGAGAGAGAG  CAGCTGAGAT  TCGGTTCCTC  CAACACCCGAG GTCATTCACA
TCCAGTCTGA  CCTCTCTCTC  GTCGACTCTA  AGCCAAGGAG  GTTGTGGGCTC CAGTAAGTGT

962
ACTACGGGTCA CGGTGGTTAC  GGTCTCGACCA TCCACTTGGG  TTGTGCCCCTG GAGGTTGCCA
TGATGCCCAGT GCCACCAATG  CCAGAGCTGGT AGGTGAACCC  AACACGGGAC  CTCCAACGGT

1022
AGCTGTTCGG  TAAGGTCCCTG GAGGAGAGAA  ACCTGCTGAC  CATGCCCTCCA TCCCACCCTGT
TCGACAAGCC  ATTCCAGGAC  CTCCTCTCTT  TGGACGACTG  GTACGGAGGT  AGGGTGGACA
                                                                    *
GAG
CTCAGCT
**SalI
```

Fig. 14

```
<------PROMOTER MOX-HGRF ADAPTOR------>>
     -34
     CGGTG GTGACATCAA TCTAAAGTA CAAAAACAAA
     ACGTGCCAC CACTGTAGTT AGATTTCAT GTTTTTGTTT
     HgiAI

<------------------------------------------->>
  1
  ATGTACGCCG ACGCCATCTT CACCAACTCC TACAGAAAGG TTCTGGGTCA GCTCTCGGCC
  TACATGCGGC TGCGGTAGAA GTGGTTGAGG ATGTCTTTCC AAGACCCAGT CGAGAGCCGG
  Met

--->
  61
  AGAAAGCTTC TGCAGGACAT CATGTCGAGA CAGCAGGGTG AGTCCAACCA GGAGAGAGGT
  TCTTTCGAAG ACGTCCTGTA GTACAGCTCT GTCGTCCCAC TCAGGTTGGT CCTCTCTCCA
  HindIII  PstI 121
  GCCAGAGCCA GACTGTGAG
  CGGTCTCGGT CTGACACTCA GCT
                    ***SalI
```

Fig. 16

```
1
CATGTACGCCG ACGCCATCTT CACCAACTCC TACAGAAAGG TTCTGGGTCA GCTCTCGGCC
CATGGTACATGCGGC TGCGGGTAGAA GTGGTTGAGG ATGTCTTTCC AAGACCCAGT CGAGAGCCGG
KpnI Met

61
AGAAAGCTTC TGCAGGACAT CTGTTCGAGA CAGCAGGGTG AGTCCAACCA GGAGAGAGGT
TCTTTCGAAG ACGTCCTGTA GACAAGCTCT GTCGTCCCAC TCAGGTTGGT CCTCTCTCCA
         HindIII PstI      cys 121
GCCAGAGCCA GACTGTGAGGTAC
CGGTCTCGGT CTGACACTC
           *** KpnI
```

Fig. 17A

```
                                                                   G GATCCACCTG
                                                                     -2125
CTTGGCCAAT GATTCAGCTG CTGGACCGAA AACGCCCTCTT TTGGCCAAAA AAAGCCCACC
           -2104
GTTGATAACT GCGGAGGCCA TATTTCAAAG AACAGCGAAT AAGAAAAAAA GGTGAATGAA
-2054                                                              -2004
ATGCGCGAAA CGATACCACT TATTAGCATA AACAAAAAAA AAAAAATCT ATTAGCTGTT
ATTATAATTA GTTCAATAAT TTCATAAGCA TCATGGTTGC GCGGCCTATT GTCATCAGTG
                                 -1904
GTCCCTCTGG AACAGGTAAA TCCACTTTGC TGAAGAAGCT GTTTGCTGAG TTCCCAGACA
                      -1854
AGTTTGGATT TTCCGTGTCC AACACCACGA GAAAACCTAG ACCTGGTGAA AAAGACGGTG
-1804
TCGATTACCA CTTCACCACG CTAGAGGACT TCAAGAAGAT GATTGAAGAA AACAAATTCA
-1754                                                              -1704
TTGAATGGGC CCAGTTCTCC GGCAACTACT ACGGCCACCTC TGTGAAAGCT GTGCAAGACG
                      -1654
TGGCCGAAGT GATGAAGAGA ACCTGTATTT TGGACATTGA TATGCAGGGT GTCAAGAGCG
                                 -1604
TCAAGAAGAC CAACCTGGGA GCCCGATTCC TCTTTATTTC TCCCTCCGTCC ATCGAAGAGC
                      -1554
TCAAGAAGAG GCTCGAGAGC CGTGGAACAG AGACCCCTGA ATCTCTTGCC AAGCGGCTTG
-1504
CTGCTGCCATC TGCGGAGATG GAGTACGCCA GGGCAGTGGA CACGACAAGG TCATTGTCAA
-1454                                                              -1404
CGATGACCTT GAGAAGGGCT ACTCTGAGCT GAAGGAGTTC ATTTCGCCCG AGCCCATCTA
                                 -1354
AGCATTCATA AATTTTTAAT ATCTAGAGCT ACAGTATCTC CTCCAACCTT
                                                      -1304
```

Fig. 17B

```
GCGTCAAGCT TGTCCTCTTC ATGCTCCTCA ACAGTCATGG CATCCAGCTG CTGCTGCTTT
                      -1254
TGCTCCAGCC TGGCATATAT GTCGGCCATAC AGCTTGAGTT GGATTTTGAT GAAACTCTCA
                      -1204
AAGGTAGGGT CCACCAGTGA CAGTCGCCAGC GCAATGAACT GCTCGATTTC GTTCTTGAGC
-1154                                                             -1104
CGTGTGTTGA TGTCCCTGTA GATATTTTCT GCCTCGTCGT ACTCAACTTT GAACTTCTGC
                                                      -1054
AGCTTGTCCA GGCTCTTCTG TAACTGGTCT GTTTTCTCGG TGTGATGCTG CTCGGTCACC
                                 -1004
TGTCGGCTCAA TCGCCTTCGTA CTCGGCTCTGC AGCTTCGAAA CCTTGAATCG TGAAACGTCG
                                                      -954
TAATCCACCT TTTGCGTGTC GCGCTTCTTG ATCAGCTTGT TGATCTCGTC GTTGTACTTC
        -904
TTCAGCTCGT TAATCGGGCTC CACGACCGTG ATGCTCATTG GCTCCAGAAT TTCTGGCAGA
-854                                                              -804
ATATTGTCTT TGATGTCTTC CACCATCTGC AGATAATTCA GAGAAATACC ATCTCTGGGG
TTCACCTTGT GCTCTTCTGG CCGTTCCGCA CCGTTCCGACC GCTTATCAGC CTTGAGCTCA
                                 -704
AAGCTATAGT CTCCGTAAAA CGAGTCCAGT GTTCTAGCCA TAGTTCCTGG TCCAGCTCGT TGGTGTAAGT
                      -654
AGATTCTCCG AAATTGCCCA CCTCCTGGAC GTCAAACTCA GGATCAACAG AGGGCTCACC
        -604                                                      -504
CTCGAGTTTG CGGAAATTGG CCTCCTGGAC GTCAAACTCA GGATCAACAG AGGGCTCACC
-554
TTTGTTTGTG CGTAGTATCA CATGTGCTCC GGCACCGATTG ACAGCTTTTT TAAACCCAAC
                                                      -454
```

Fig. 17C

```
CCATGACATG TCGAGGAAAG GGTCGTTTCG GGGAGTTAAA TATTTTGGC TATGTAGCAG
                                              -404
ACATGTTTCG ACGCTGGCGT CGCGTCGATC GGAAAATATT ACCCCAGGAA CAAGCACTTG
                         -354
CTTGGGTTAG CCACCACCCT GGGCAAGCCT TTTGCCCGGC TCTACACAGG GCCAATGAAA
              -304
TCTGGGCGGA ATCTGAAACC GATGAAACGG ACGACACTGG CAACAAGCTC ACTGCACTAT
   -254                                                     -204
TTTTTTTC TAGTGAAATA GCCTATCCTC CTCTCGCCTC CCTCATACCT GTAAAGGGGT
                                              -154
GCAATTTAGC CTCGTTCCAG CCATTCACGG CCCACTCAAC AACACGTCGG CTACCATGGG
                              -104
GTGCTTGGGC ACCAAAAGGC CTATAAATAG GCCCCCCATCC GTCTGCTACA CAGTCATCTC
                        -54
       1                                    5                          10                        15
   MET SER MET ARG ILE PRO LYS ALA ALA SER VAL ASN ASP GLU GLN HIS
TGTCTTTTCTTCCC ATG AGT ATG AGA ATC CCT AAA GCA GCG TCG GTC AAC GAC GAA CAA CAC
 -14
       20                                   25                         30                        35
   GLN ARG ILE ILE LYS TYR GLY ARG ALA LEU VAL LEU ASP ILE VAL GLU GLN TYR GLY GLY
   CAG AGA ATC ATC AAG TAC GGT CGT CGC CTT GTC CTG GAC ATT GTC GAG CAG TAC GGA GGA
                         40                                  45                        50                         55
       GLY PRO GLY SER ALA MET GLY ALA MET ALA ILE GLY ILE ALA LEU TRP LYS TYR THR
       GGC CAC CCG GGC TCG GCC ATG GGC GCC ATG GCT ATC GGA ATT GCT CTG TGG AAA TAC ACC
                          60                                 65                        70                         75
       LEU LYS TYR ALA PRO ASN ASP PRO ASN TYR PHE ASN ARG ASP ARG PHE VAL LEU SER ASN
       CTG AAA TAT GCT CCC AAC GAC CCT AAC TAC TTC AAC AGA GAC AGG TTT GTC CTG TCG AAC
                           80                                 85                        90                         95
       GLY HIS VAL CYS LEU PHE GLN TYR ILE PHE GLN HIS LEU TYR GLY LEU LYS SER MET THR
```

Fig. 17D

| GGT | CAC | GTC | TGT | CTG | TTC | CAG | TAT | ATC | TTC | CAG | CAC | CTG | TAC | GGT | CTC | AAG | TCG | ATG | ACC |
|---|---|---|---|---|---|---|---|---|---|---|---|---|---|---|---|---|---|---|---|
| | | | 100 | | | | 105 | | | | 110 | | | | 115 | | | | |

| MET | ALA | GLN | LEU | LYS | SER | TYR | HIS | ASN | ASP | PHE | HIS | LEU | SER | CYS | PRO | GLY | HIS | PRO |
|---|---|---|---|---|---|---|---|---|---|---|---|---|---|---|---|---|---|---|
| ATG | GCG | CAG | CTG | AAG | TCC | TAC | CAC | AAT | GAC | TTC | CAC | CTG | TCG | TGT | CCC | GGT | CAC | CCA |
| | | 120 | | | | 125 | | | | 130 | | | | 135 | | | |

| GLU | ILE | GLU | HIS | ASP | ALA | VAL | GLU | THR | THR | GLY | PRO | LEU | GLY | GLN | GLY | ILE | SER | ASN |
|---|---|---|---|---|---|---|---|---|---|---|---|---|---|---|---|---|---|---|
| GAA | ATC | GAG | CAC | GAC | GCC | GTC | GAG | ACA | ACG | GGC | CCG | CTC | GGC | CAG | GGC | ATC | TCG | AAC |
| | 140 | | | | 145 | | | | 150 | | | | 155 | | | | |

| SER | VAL | GLY | LEU | LEU | ALA | ILE | ALA | THR | LYS | ASN | LEU | ALA | ALA | TYR | ASN | LYS | PRO | GLY | PHE |
|---|---|---|---|---|---|---|---|---|---|---|---|---|---|---|---|---|---|---|---|
| TCT | GTT | GGT | CTG | CTG | GCC | ATA | GCT | ACC | AAA | AAC | CTG | GCC | GCC | TAC | AAC | AAG | CCG | GGC | TTT |
| 160 | | | | 165 | | | | 170 | | | | 175 | | | | | | |

| ASP | ILE | THR | ASN | LYS | VAL | TYR | CYS | MET | VAL | GLY | ASP | ALA | CYS | LEU | GLN | GLU | GLY | PRO |
|---|---|---|---|---|---|---|---|---|---|---|---|---|---|---|---|---|---|---|
| GAT | ATC | ACC | AAC | AAG | GTG | TAC | TGC | ATG | GTT | GGC | GAT | GCG | TGC | TTG | CAG | GAG | GGC | CCT |
| | | 180 | | | | 185 | | | | 190 | | | | 195 | | | |

| ALA | LEU | GLU | ILE | SER | ILE | CYS | CYS | ASP | ILE | GLY | HIS | MET | GLY | SER | VAL | ASP | ILE | VAL | LEU | TYR |
|---|---|---|---|---|---|---|---|---|---|---|---|---|---|---|---|---|---|---|---|---|
| GCT | CTC | GAG | ATC | TCG | ATC | TGC | TGT | GAC | ATT | GGG | CAC | ATG | GGC | AGT | GTT | GAC | CTG | CTC | TAC |
| | | 200 | | | | 205 | | | | 210 | | | | 215 | | | | |

| ASN | ASN | GLN | VAL | CYS | CYS | ASN | TRP | GLY | SER | VAL | ASP | ILE | ALA | ASN | THR | GLU | ASP | ILE | SER |
|---|---|---|---|---|---|---|---|---|---|---|---|---|---|---|---|---|---|---|---|
| AAC | AAC | CAG | GTC | TGC | TGT | AAC | TGG | GGC | AGT | GTT | GAC | ATT | GCC | AAC | ACG | GAG | GAC | ATC | AGT |
| | 220 | | | | 225 | | | | 230 | | | | 235 | | | | | |

| ALA | LYS | PHE | ALA | ALA | CYS | ASN | VAL | ILE | GLU | VAL | ILE | GLU | VAL | ALA | SER | GLU | ASP | VAL |
|---|---|---|---|---|---|---|---|---|---|---|---|---|---|---|---|---|---|---|
| GCC | AAG | TTC | AAG | GCC | TGC | AAC | GTG | ATC | GAG | GTC | ATC | GAG | GTC | TCC | GAG | GAC | GTG |
| 240 | | | | 245 | | | | 250 | | | | 255 | | | | | |

| ALA | THR | ILE | VAL | LYS | ALA | LEU | GLU | TYR | ALA | GLN | ALA | GLU | LYS | HIS | ARG | PRO | THR | LEU | ILE |
|---|---|---|---|---|---|---|---|---|---|---|---|---|---|---|---|---|---|---|---|
| GCT | ACC | ATT | GTC | AAG | GCC | TTG | GAG | TAC | GCG | CAG | GCC | GAG | AAG | CAC | AGA | CCA | ACA | CTT | ATC |
| 260 | | | | 265 | | | | 270 | | | | 275 | | | | | |

| ASN | CYS | ARG | THR | VAL | ILE | GLY | SER | GLY | ALA | ALA | PHE | GLU | ASN | HIS | CYS | ALA | HIS | GLY |
|---|---|---|---|---|---|---|---|---|---|---|---|---|---|---|---|---|---|---|
| AAC | TGC | AGA | ACT | GTG | ATT | GGA | TCG | GGT | GCT | GCG | TTC | GAG | AAC | CAC | TGT | GCG | CAC | GGT |

Fig. 17E

```
ASN ALA LEU GLY GLU ASP GLY VAL ARG GLU LEU LYS ILE TYR GLY MET ASN PRO ALA
AAC GCT CTG GGC GAG GAC GGT GTG CGC GAG CTC AAA ATC TAC GGC ATG AAC CCG GCC
            280             285             290             295

GLN LYS PHE TYR ILE PRO GLN ASP PHE PHE LYS GLU LYS TYR GLY MET PRO ALA GLU GLY
CAG AAG TTC TAC ATT CCG CAG GAC TTC TTC AAA GAG AAG TAC GGC ATG CCG GCC GAG GGC
    300             305             310             315             320

ASP LYS LEU VAL ALA GLU TRP LYS LYS VAL ALA LYS TYR VAL ALA TYR PRO GLU
GAC AAG CTG GTG GCC GAA TGG AAG AAG GTC GCC AAG TAC GTC GCG TAC CCT GAG
        325             330             335             340

GLU GLN GLN PHE LEU ALA ARG GLY LEU LEU PRO THR ARG LYS ASN TRP LYS SER PHE
GAG CAG CAG TTT TTG GCC CGG GAG CTG CTG CCA ACA AGG AAG AAC TGG TCG TTC
    345             350             355             360

LEU PRO GLN GLU PHE THR GLY ASP PRO THR ARG ALA ALA ALA ARG GLU LEU VAL
CTG CCG CAA TTC ACC GGC GAC CCT ACA AGG GCC GCC GCT GCC AGA GAG CTT GTG
        365             370             375             380

ARG ALA LEU ASN TRP PRO GLY VAL LYS SER VAL ILE ALA GLY CYS ASP LEU SER SER
AGA GCC CTG AAC TGG CCA GGG GTC TCG ATT GCC GGT TGC GAC CTG TCT TCT
    385             390             395             400

VAL ASN LEU GLN TRP PRO GLY TYR PHE MET ASP TYR ILE GLU TYR ILE ARG GLU HIS ALA MET
GTC AAT TTG CAG TGG CCA GGG TAT TTC ATG GAC TAC ATT GAG TAC ATC AGA GAA CAC GCC ATG
        405             410             415             420

GLY SER GLY ASP TYR ALA ARG TYR ASN GLY LYS THR SER
GGC CTG AGC GCC TAC TCC GGC AGA TAC AAC AAG GGC ACG
    425             430             435             440

CYS ALA ILE ALA ASN GLY LEU ALA ALA TYR ASN LYS GLY PHE LEU PRO ILE THR SER
TGT GCT ATC GCC AAT GGC CTT GCC GCC TAC AAC AAG GGC TTC CTG CCG ATC ACG TCG
        445             450             455             460

THR PHE PHE MET PHE TYR LEU TYR ALA ALA PRO ALA ILE ARG MET ALA GLY LEU GLN GLU
ACG TTC TTC ATG TTC TAC CTG TAC GCC GCC CCG GCC ATC CGG ATG GCC GGC CTG CAG GAG
            465             470             475
```

Fig. 17F

| | | | | | | | | | | |
|---|---|---|---|---|---|---|---|---|---|---|
| ACT | TTC | ATG | TTC | TAC | CTG | TAC | GCT | GCC | CCA | ATC | AGA | ATG | GCC | CTG | CAG | GAG |
| | | 480 | | | | | 485 | | | | 490 | | | | 495 | |
| LEU | LYS | ALA | HIS | ILE | GLY | THR | ASP | SER | ILE | ASN | GLY | GLU | ASN | GLY | PRO | THR |
| CTC | AAG | GCG | CAC | ATC | GGC | ACC | GAC | TCG | ATC | AAT | GAG | GGT | AAC | GGC | CCT | ACG |
| | | 500 | | | | | 505 | | | | 510 | | | | 515 | |
| HIS | GLN | PRO | VAL | GLU | SER | PRO | ALA | PHE | ARG | ALA | TYR | ASN | ILE | TYR | MET | ARG |
| CAC | CAG | CCG | GTC | GAG | TCG | CCA | GCA | TTG | CGG | GCC | TAT | AAC | ATT | TAC | ATG | AGA |
| | | 520 | | | | | 525 | | | | 530 | | | | 535 | |
| PRO | VAL | ASP | SER | ALA | GLU | VAL | PHE | GLY | LEU | PHE | GLN | LYS | VAL | GLU | PHE | SER |
| CCG | GTC | GAC | TCT | GCA | GAA | GTG | TTT | GGC | CTG | TTC | CAA | AAA | GTC | GAG | TTC | AGC |
| | | 540 | | | | | 545 | | | | 550 | | | | 555 | |
| SER | ILE | LEU | SER | LEU | SER | ARG | ASN | GLU | VAL | LEU | GLN | TYR | LEU | ALA | SER | ARG | ALA | GLN | ARG |
| TCG | ATT | CTG | TCG | CTC | TCG | AGA | AAC | GAG | GTG | CTG | CAA | TAC | CTG | GCA | AGT | CGA | GCG | CAG | AGA |
| | | 560 | | | | | 565 | | | | 570 | | | | 575 | |
| ARG | ARG | ASN | ALA | ALA | GLY | TYR | ILE | LEU | GLU | ASP | ALA | GLU | ALA | GLU | VAL | GLN | ILE | ILE |
| AGG | CGC | AAC | GCG | GCC | GGC | TAT | ATT | CTG | GAG | GAT | GCG | GAG | GCC | GAG | GTG | CAG | ATT | ATT |
| | | 580 | | | | | 585 | | | | 590 | | | | 595 | |
| GLY | VAL | GLY | ALA | GLU | MET | GLU | PHE | ALA | ASP | LYS | ALA | LYS | ILE | LEU | GLY | ARG | LYS | PHE |
| GGA | GTT | GGT | GCA | GAG | ATG | GAG | TTT | GCA | GAC | AAG | GCC | AAG | ATC | TTG | GGC | AGA | AAG | TTC |
| | | 600 | | | | | 605 | | | | 610 | | | | 615 | |
| ARG | THR | ARG | VAL | LEU | SER | ILE | PRO | CYS | THR | ARG | LEU | PHE | ASP | GLU | GLN | SER | ILE | GLY | TYR |
| AGG | ACC | AGA | GTT | CTC | TCC | ATC | CCA | TGC | ACG | CGG | CTG | TTT | GAC | GAG | CAG | TCG | ATC | GGC | TAT |
| | | 620 | | | | | 625 | | | | 630 | | | | 635 | |
| ARG | SER | VAL | LEU | ARG | LYS | ASP | GLY | ARG | GLN | VAL | PRO | THR | VAL | VAL | ASP | GLY | HIS |
| AGA | CGC | TCG | GTT | TTG | AGA | AAG | GAC | GGC | CAG | GTG | CCA | ACG | GTG | GTG | GAC | GGC | CAC |
| | | 640 | | | | | 645 | | | | 650 | | | | 655 | |
| VAL | ALA | PHE | GLY | TRP | GLU | ARG | TYR | ALA | THR | ALA | SER | TYR | CYS | MET | ASN | THR | TYR | GLY | LYS |
| GTT | GCG | TTC | GGC | TGG | GAG | AGA | TAC | GCT | ACG | GCT | TCC | TAC | TGT | ATG | AAC | ACG | TAC | GGC | AAG |

Fig. 17G

```
SER LEU PRO PRO GLU VAL ILE TYR GLU TYR PHE GLY TYR ASN PRO ALA THR ILE ALA LYS
TCT CTG CCT CCA GAA GTG ATC TAC GAG TAC TTT GGA TAC AAC CCG GCA ACG ATT GCC AAG
                660                 665                 670                 675
LYS VAL GLU ALA TYR VAL ARG ALA CYS GLN ARG ASP PRO LEU LEU HIS ARG LEU PRO
AAG GTC GAA GCG TAC GTC CGG GCG TGC CAA AGA GAC CCT TTG CTG CAC CGA CTT CCT
                680                 685                 690                 695
GLY PRO GLU GLY LYS ALA ***
GGA CCT GAA GGA AAA GCC TAA CCACGAT AAAGTAAATA AGCTCTGATT AAGTAAGATG
                700                      2110

AATAAGTTCT TTGTCTGTGA ATGCCACCCC ACAATAACCC CACAAATAAA ACTTTCACAC
2160                                                              2210
TTGCGTCAGA AACTGTCGAG CCGCACGGGA CTGACTGTTT GGCGGCCGTGC CTCTGTCCCC
                                                        2260
ACACGGATAT TTCGCACGGA ACAGAAACCA TTGGACAAGG GGTTGCTGCC GATACCAAAT
                                           2310

AGAATGCATC GGATCC
                2350
```

Fig. 19

Identical sequences in -1000 region of DAS and MOX genes

```
DAS -1076
TAGATATTTCTGCCTCGTACTCA-54N-GTGTGATG-8N-TCACC-9N-
*  ** *****  **********       *         *****       *****
  *  **  **********  **************************
         TCGAAATTTTTGCCGTCGTACAGTGTGATGTCACC
MOX -1052

DAS                                          -937
         ATCGCTTCGTACTCGCTCTGCAGCTTCGA
         ****  ****  *  *********** ***
         ****  ****  ** **********  ***
         ATCGAATGTAATGAGCTGCAGCTTGCGA
MOX                                          -987
```

REGULATORY SEQUENCES OF ALCOHOL OXIDASE (MOX) AND DIHYDROXYACETONESYNTHASE (DAS) OF HANSENULA POLYMORPHA

This is a continuation of application Ser. No. 07/300,211, filed on Jan. 23, 1989, now abandoned, which is a continuation of Ser. No. 06/759,315, filed Jul. 26, 1985, now abandoned.

The present invention relates to a process for microbiologically preparing oxidoreductases, use of these enzymes in bleaching and/or detergent compositions, as well as to microorganisms transformed by DNA sequences coding for an oxidoreductase and optionally for a dihydroxyacetone synthase-enzyme, and *H. polymorpha* alcohol oxidase and/or dihydroxyacetone synthase regulation sequences, the microorganisms being suitable for use in the process.

Oxidoreductases, especially those which use oxygen as electron acceptor, are enzymes suitable for use in bleaching and/or detergent compositions in which they can be used for the in situ formation of bleaching agents, e.g. $H_2O_2$, during the washing or bleaching process. See for example GB-PS 1 225 713 (Colgate-Palmolive Company), in which the use of a mixture of glucose and glucose oxidase and other ingredients in a dry powdered detergent composition has been described, DE-PA 2 557 623 (Henkel & Cie GmbH), in which the use of a $C_1$ to $C_3$ alkanol and alcohol oxidase, or galactose and galactose-oxidase, or uric acid and uratoxidase, and other ingredients in a dry detergent composition having bleaching properties has been described, and GB-PA 2 101 167 (Unilever PLC) in which the use of a $C_1$ to $C_4$ alkanol and a $C_1$ to $C_4$ alkanol oxidase in a liquid bleach and/or detergent composition has been described, wherein the alkanol and the enzyme are incapable of substantial interaction until the composition is diluted with water, and/or has come into contact with sufficient oxygen.

Up to now natural oxidase-enzymes cannot be produced at a cost price that allows industrial application on a large scale, e.g. detergent products. Moreover, the oxidase-enzymes have to act under non-physiological conditions when used in detergent and bleaching products. Further the natural oxidases that have been investigated for use in detergent compositions are accompanied by the natural catalase-enzyme which decomposes almost immediately the peroxide(s) formed, so that no effective bleaching is obtained. Thus a need exists for oxidase-enzymes that are more suitable for use under the conditions of manufacture and use of detergent and bleaching products.

For an economically feasible production of these oxidases it is further required to reach a yield of these enzymes in fermentation processes in the order of that of alcohol oxidase of *H. polymorpha,* which is up to 20% of the cellular protein (van Dijken et al., 1976).

One way of finding new microorganisms producing enzymes in higher amounts or finding new oxidase-enzymes having improved properties is to check all sorts of microorganisms and try to isolate the relevant oxidases, which are then checked for their abilities to generate peroxides and their stabilities under the conditions of manufacture and use of detergent and bleaching products. One can hope that some day a suitable enzyme will be found, but the chance of success is unpredictable and probably very low.

Another way is to apply another trial and error method of crossing the natural microorganisms producing these oxidases by classical genetic techniques, in the hope that some day one will find a more productive microorganism or a more suitable enzyme, but again the chance of success is rather low.

Clearly, a need exists for a method for preparing oxidase-enzymes in higher yield and/or without the concomitant formation of catalase and/or having improved properties during storage and/or use in e.g. bleach and/or detergent compositions. The problem of trial and error can be overcome by a process for preparing an oxidase-enzyme by culturing a microorganism under suitable conditions, and preferably concentrating the enzyme and collecting the concentrated enzyme in a manner known per se, which process is characterized in that a microorganism is used that has been obtained by recombinant DNA technology and which is capable of producing said oxidase-enzyme.

The microorganisms suitable for use in a process for preparing an oxidase-enzyme can be obtained by recombinant DNA technology, whereby a microorganism is transformed by a DNA sequence coding for an oxidase-enzyme (so-called structural gene) together with one or more other DNA sequences which regulate the expression of the structural gene in a particular microorganism or group of organisms, either via introduction of an episomal vector containing said sequences or via a vector containing said sequences which is also equipped with DNA sequences capable of being integrated into the chromosome of the microorganism.

The determination of a structural gene coding for the enzyme alcohol oxidase (EC 1.1.3.13; (mox) originating from *H. polymorpha* together with its regulatory 5'- and 3'-flanking regions will be described as an example of the invention without the scope of the invention being limited to this example. The spirit of the invention is also applicable to the isolation of DNA sequences of other oxidase-enzymes such as glycerol oxidase, glucose oxidase, D-amino acid oxidase etc.; the incorporation of the DNA sequences or modifications thereof into the genome of microorganisms or into episomal vectors used for transforming microorganisms and the culturing of the transformed microorganisms so obtained as such or for producing the desired oxidase-enzymes, as well as the use of these enzymes in bleaching compositions containing them.

Although the microorganisms to be used can be bacteria, e.g. of the genus Bacillus, as well as moulds, the use of yeasts is preferred for technological and economical reasons. In particular a mould or yeast can be selected from the genera Aspergillus, Candida, Geotrichum, Hansenula, Lenzites, Nadsonia, Pichia, Poria, Polyporus, Saccharomyces, Sporobolomyces, Torulopsis, Trichosporon and Zendera, more particularly from the species *A. japonicus, A. niger, A. oryzae, C. boidinii, H. polymorpha, Pichia pastoris* and Kloeckera sp. 2201. The latter name is sometimes used instead of *C. boidinii.*

Many $C_1$-utilizing yeasts have been isolated during the last decade, and for *Hansenula polymorpha* and *Candida boidinii* the methanol metabolism has been studied extensively (for a review see Veenhuis et al., 1983).

The first step in this metabolism is the oxidation of methanol to formaldehyde and $H_2O_2$ catalysed by MOX. Formaldehyde is oxidized further by the action of formaldehyde dehydrogenase and formate dehydrogenase. $H_2O_2$ is split into water and oxygen by catalase.

Alternatively, methanol is assimilated into cellular material. After its conversion into formaldehyde, this product is fixed through the xylulose monophosphate pathway into carbohydrates. Dihydroxyacetone synthase (DAS) plays a crucial role in this assimilation process.

The appearance of MOX, formate dehydrogenase, formaldehyde dehydrogenase, DAS and catalase is subject to glucose repression, e.g. on 0.5% glucose. However, synthesis of MOX is derepressed by growth in low concentrations of glucose (0.1%), contrary to the synthesis of DAS, which is still fully repressed under these conditions (Roggenkamp et al., 1984).

Regulation, i.e. the possibility to switch "on" or "off" of the gene for the polypeptide concerned, is desirable, because it allows for biomass production, when desired, by selecting a suitable substrate, such as, for example molasses, and for production of the polypeptide concerned, when desired, by using methanol or mixtures of methanol and other carbon sources. Methanol is a rather cheap substrate, so the polypeptide production may be carried out in a very economical way.

After derepression of the gene coding for alcohol oxidase (MOX) by growth on methanol, large microbodies, the peroxisomes are formed. While glucose-grown cells contain only a small peroxisome, up to 80% of the internal volume of the cell is replaced by peroxisomes in the derepressed state. The conversion of methanol into formaldehyde and $H_2O_2$ as well as the degradation of $H_2O_2$ has been shown to occur in these peroxisomes, while further oxidation or assimilation of formaldehyde most probably occurs in the cytoplasm. This process is a perfect example of compartmentalization of toxic products, of a strong co-ordinate derepression of several cellular processes and of the selective translocation of at least two of the enzymes involved in this process.

Most of the enzymes involved in the methanol metabolism have been purified and characterized (Sahm, 1977, Bystrykh et al, 1981). Especially methanol oxidase (EC 1.1.3.13) has been studied in detail. It is an octamer consisting of identical monomers with an $M_r$ value of about 74 kd and it contains FAD as a prosthetic group. Up to now no cleavable signal sequence for translocation could be detected, as concluded from electroelephoresis studies with in vivo and in vitro synthesized products (Roa and Blobel, 1983) or from in vitro synthesis in the presence of microsomal membranes (Roggenkamp et al., 1984).

Under derepressed conditions, up to 20% of the cellular protein consists of MOX.

FIG. 1. The exonuclease Bal31 digestion strategy used in sequencing specific MOX subclones. The fragment X-Y subcloned in M13mp-8 or -9, -18 or -19 is cut at the unique restriction site Z. The DNA molecule is subjected to a time-dependent exonuclease Bal31 digestion. The DNA fragment situated near the M13 sequencing primer is removed using restriction enzyme Y; ends are made blunt end by incubation with $T_4$-DNA polymerase and then ligated intramolecularly. Phage plaques are picked up after transformation and the fragment is sequenced from site Z in the direction of site X. Using the M13 derivative with a reversed multiple cloning site, the fragment is sequenced from site Z in the direction of site X.

Figure 2:
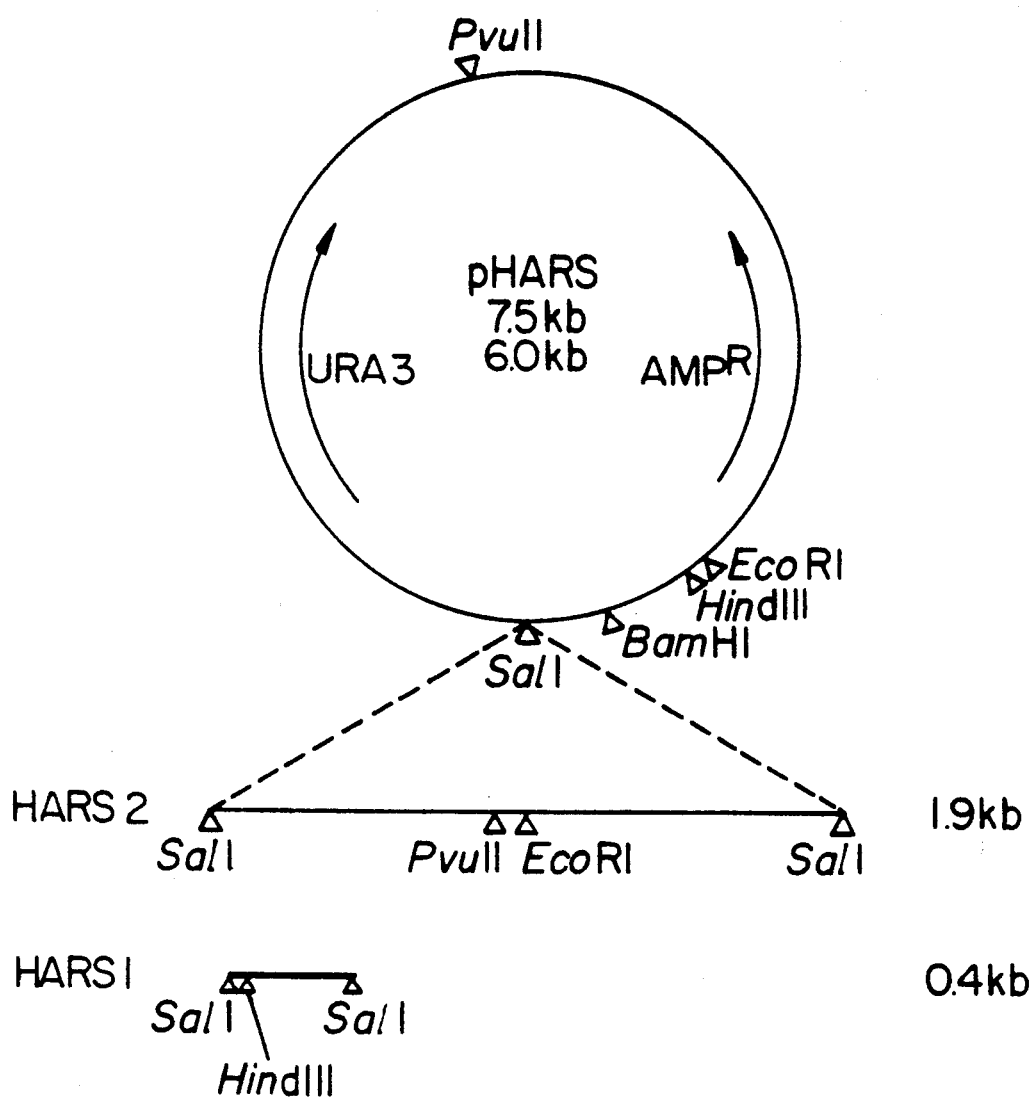

FIG. 2. Alignment of pHARS plasmids derived by insertion of HARS fragments into the single SalI site of YIp5.

Figure 3:
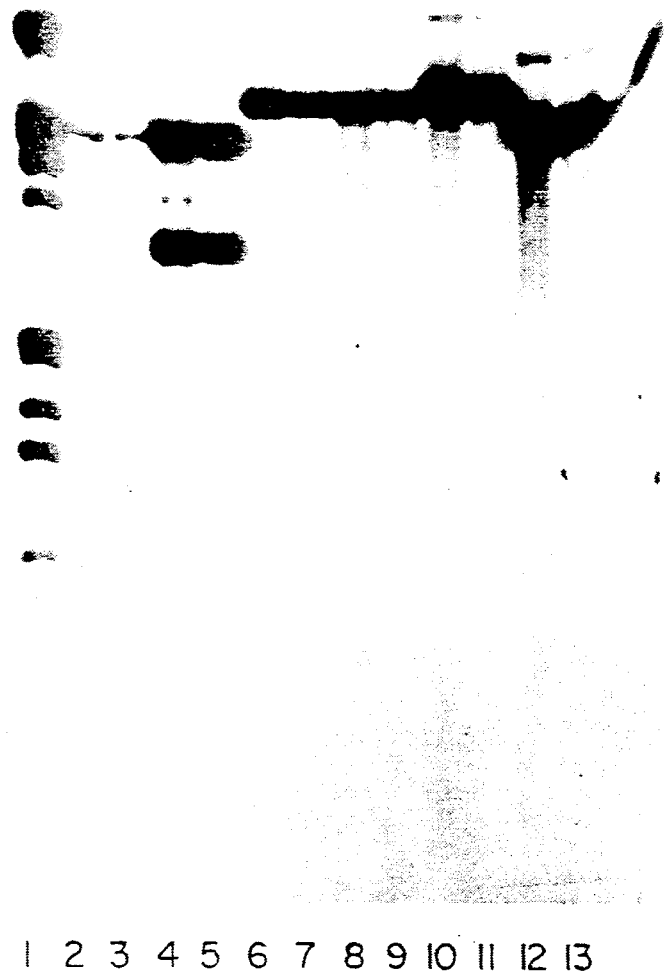

FIG. 3. Estimation of copy number by Southern hybridization of *H. polymorpha* transformants. An aliquot of 8 and 16 /μl of each probe was electrophoresed. Lane 1, phage lambda DNA digested with HindIII and EcoRI. Lanes 2,3 transformant of *K. Lactis* containing two copies of integrated plasmid, digested with HindIII (M. Reynen, K. Breunig and C.P. Hollenberg, unpublished); lanes 4-7, YNN 27, transformed with pRB58 (4-5) and YRP17 (6-7) digested with EcoRI respectively; lanes 8,9, LR9 transformed with YPR17 digested with EcoRI; lanes 10, 11, LR9 transformed with pHARS2 digested with HindIII; lanes 12,13, LR9 transformed with pHARS1 digested with EcoRI.

Figure 4:

FIG. 4. Autoradiogram of Southern blots of DNA from *H. polymorpha* mutant LR9 transformed by integration of plasmid YIp5. Lane 1, phage lambda DNA, digested both with HindIII and EcoRI; lane 2, pHARS-1, undigested; lanes 3-5 and lanes 6,7 show DNA from 2 different transformants. Lane 3, undigested; lane 4, digested with EcoRI; lane 5, digested with PvuII; lane 6, digested with EcoRI; lane 7, digested with PvuII; lane 8, plasmid YIp5, digested with EcoRI. Nick-translated YIp5 was used as a hybridization probe.

Figure 5:
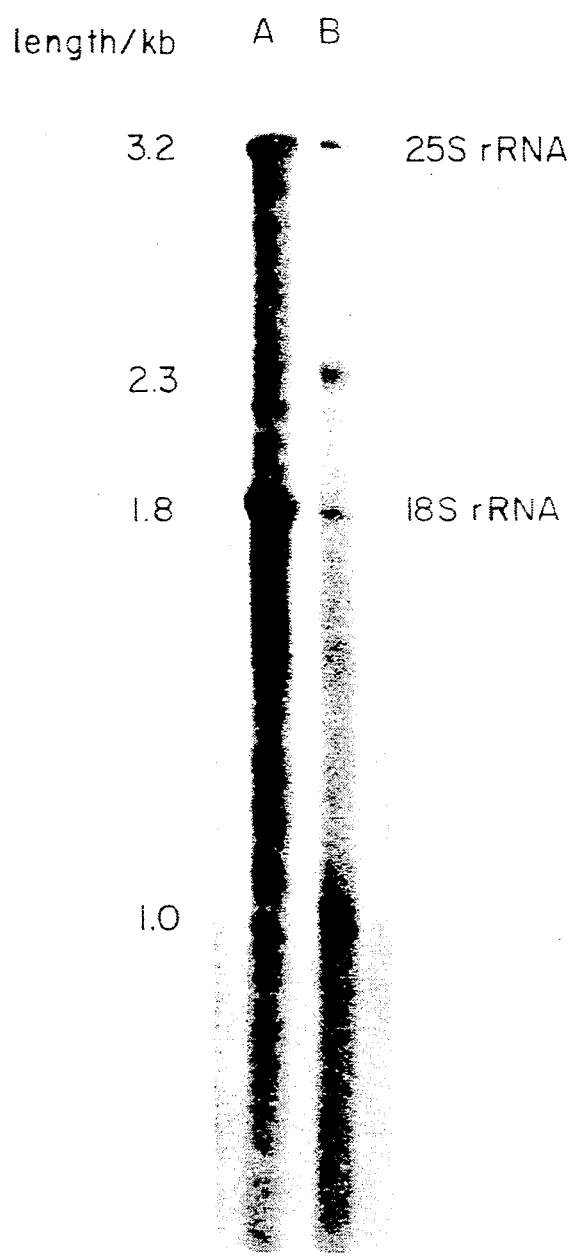

FIG. 5. Electrophoresis of $^{32}$p-labelled RNA from *Hansenula polymorpha*, purified once (lane A) or twice (lane B) on oligo(dT)cellulose. Electrophoresis was performed on a denaturing 7M urea 2.5% polyacrylamide gel. The position of the yeast rRNA's and their respective molecular weights are indicated by 18S and 25S. The 2.3 kb band, that can be seen in lane B, was converted into a cDNA probe which was subsequently used to isolate MOX and DHAS clones from the *Hansenula polymorpha* clone bank.

Figure 6:
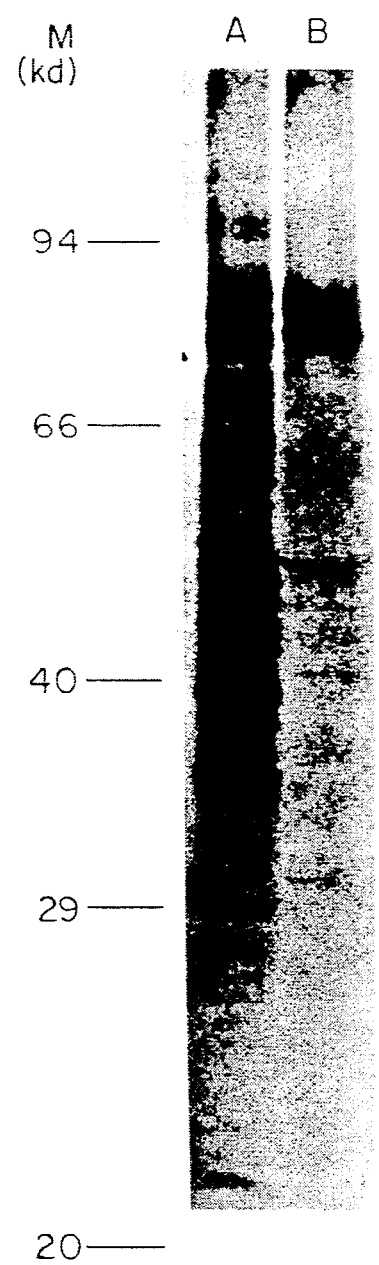

FIG. 6. $^{35}$S-labelled proteins obtained after in vitro translation of methanol derepressed, *Hansenula polymorpha* mRNA with a rabbit reticulocyte lysate. Either 2 microliters of the total lysate (lane A) or an immunoprecipitate of the remaining 18 microliters using a MOX specific antiserum (lane B) were separated on an 11.5% SDS-polyacrylamide gel. A mixture of proteins with known molecular weights was used as markers.

FIG. 7. The N-terminal sequence of purified MOX, as determined on a Beckman sequenator. The two probes that could be derived from the sequence Pro-Asp-Gln-Phe-Asp, using Saccharomyces preferred codons, are indicated.

Figure 8B:
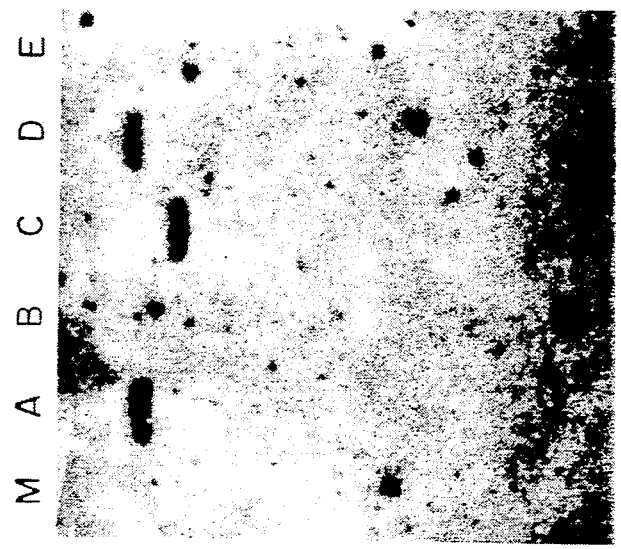
Figure 8A:
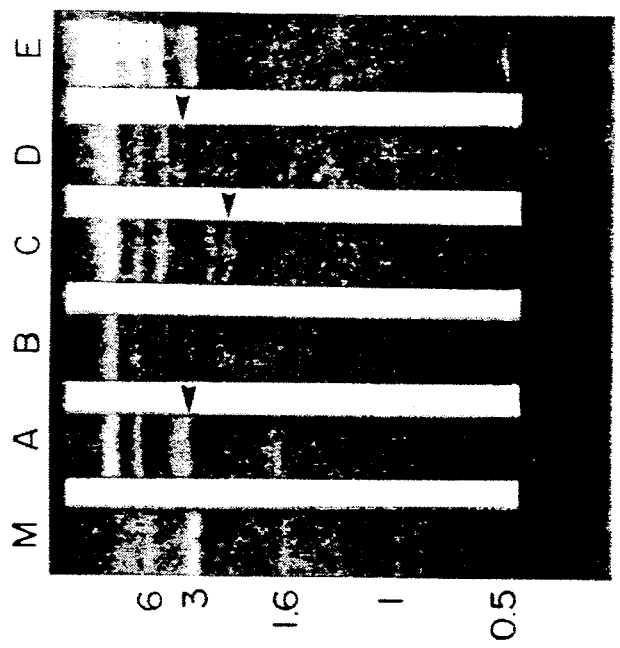

FIG. 8A, B. Hybridization of a DBM blot of HindIII/SalI cut MOX clones. The DNA was separated on a 1.5% agarose gel (FIG. 9A) and the blot was hybridized to a mixture of both MOX-derived synthetic DNA probes (FIG. 8). Only one band of clones 1, 4 and 5 hybridize (FIG. 9B), indicated by an arrow in FIG. 9A. Lane M: molecular weight markers as indicated. Lane A, B, C and D: clones 1, 3, 4 and 5, respectively. Lane E: lambda L47.1.

Figure 9:
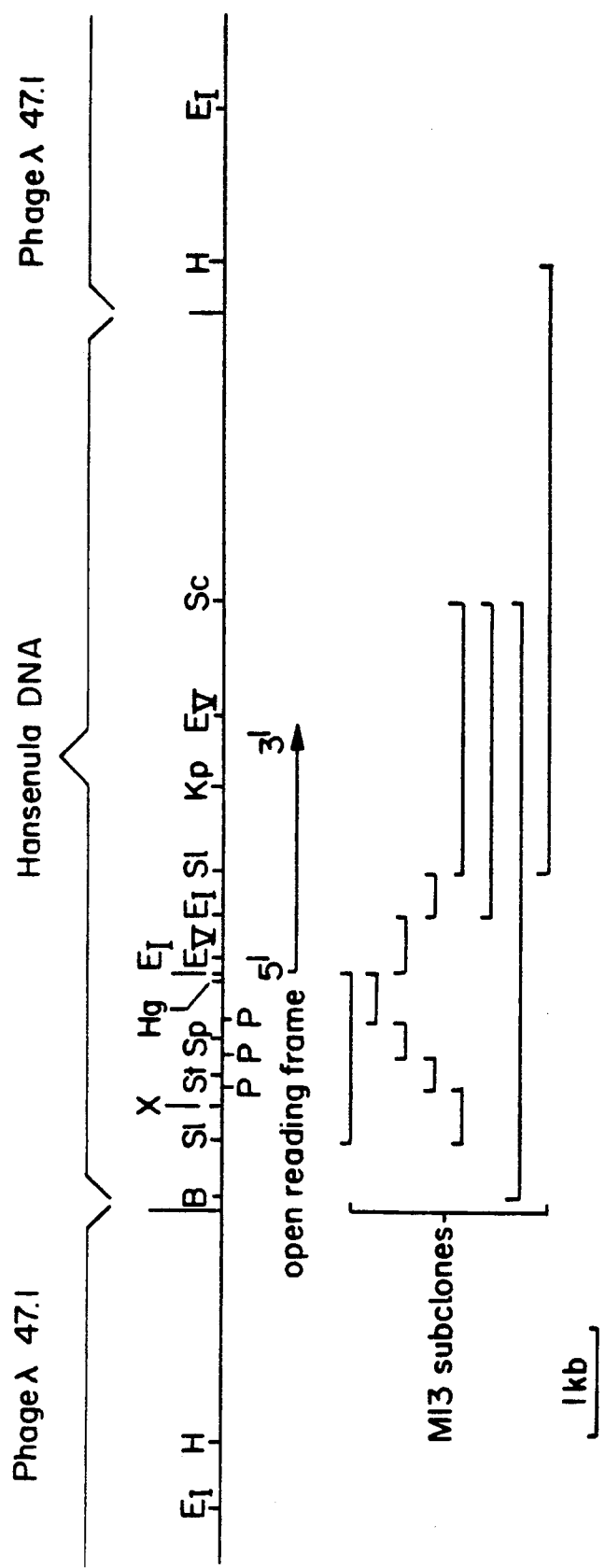

FIG. 9. Restriction map for MOX clone 4. Only relevant restriction sites are indicated that have been used for subcloning and sequencing of the MOX gene. The open reading frame, containing the structural MOX sequence, and the M13 subclones made are depicted. Restriction sites used are: B=BamHI, $E_I$=EcoRI, $E_V$=EcoRV, P=PatI, Sl=SalI, Sc=SacI, St=StuI, H=HindIII, Sp=SphI, K=KpnI, Hg=HgiAI and X=XmaI.

FIG. 10A-G. The nucleotide sequence of the MOX structural gene and its 5'- and 3'-flanking sequence.

Figure 11A:
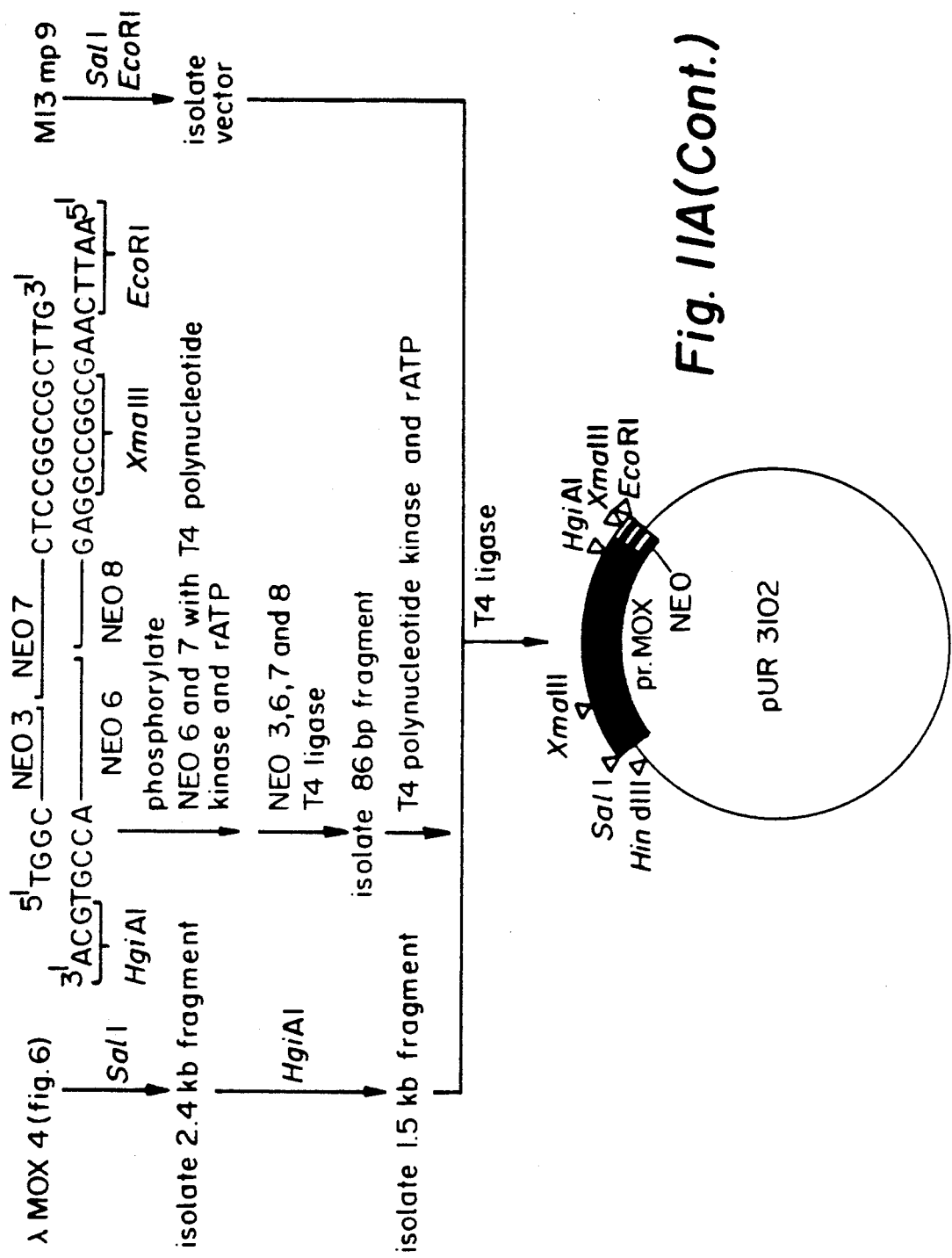

FIG. 11A,C. The construction of plasmid pUR 3105 by which the neomycin phosphotransferase gene integrates into the chromosomal MOX gene of *H. polymorpha*.

FIG. 11B. Promoter MOX-neomycin phosphotransferase adapter fragments.

FIG. 12A-C. The DNA sequence of the AAO gene, derived from the published amino acid sequence. The gene is synthesised in the optimal codon use for *H. polymorpha* in oligonucleotides of about 50 nucleotides long. Restriction sites, used for subcloning are indicated. The HgiAI-SalI fragment forms the adapter between the structural AAO gene and the MOX promoter. The translational start codon (met) and stop codon (***) are indicated. The structural sequence is numbered from 1 to 1044, while the MOX promoter is numbered from −34 to −1.

Figure 13A:
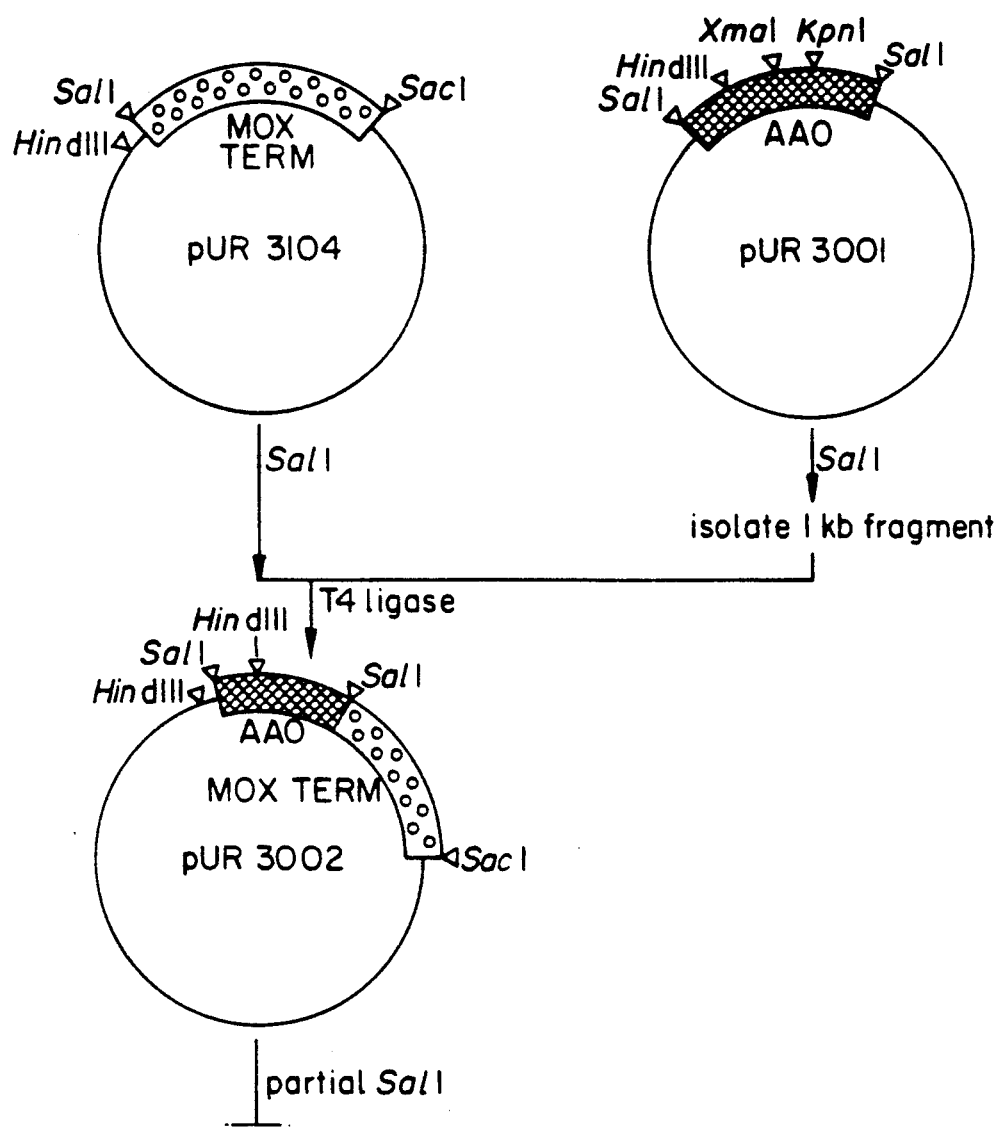
Figure 13A:
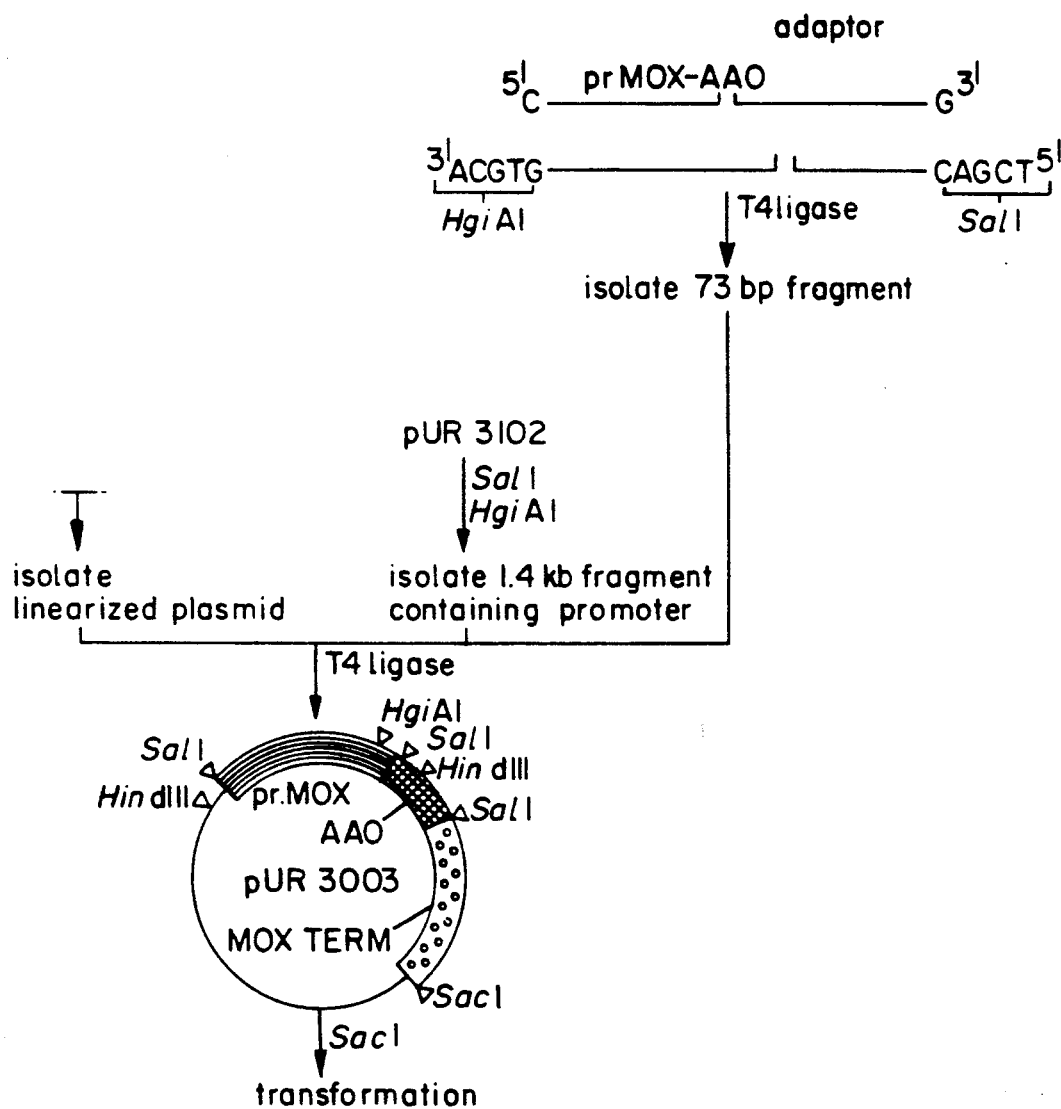

FIG. 13A. The construction of pUR 3003, by which the AAO gene integrates into the chromosomal MOX gene of *H. polymorpha*. Selection on activity of the AAO gene.

Figure 13B:
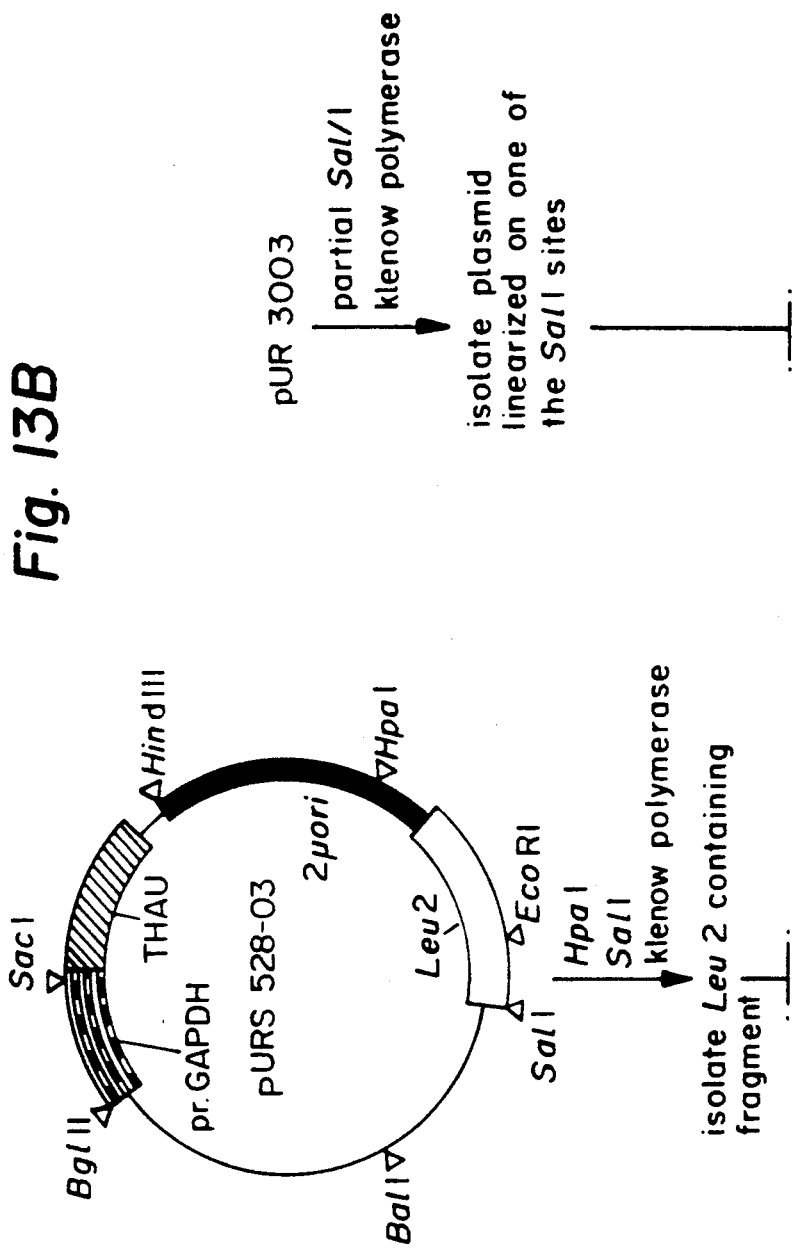
Figure 13B:
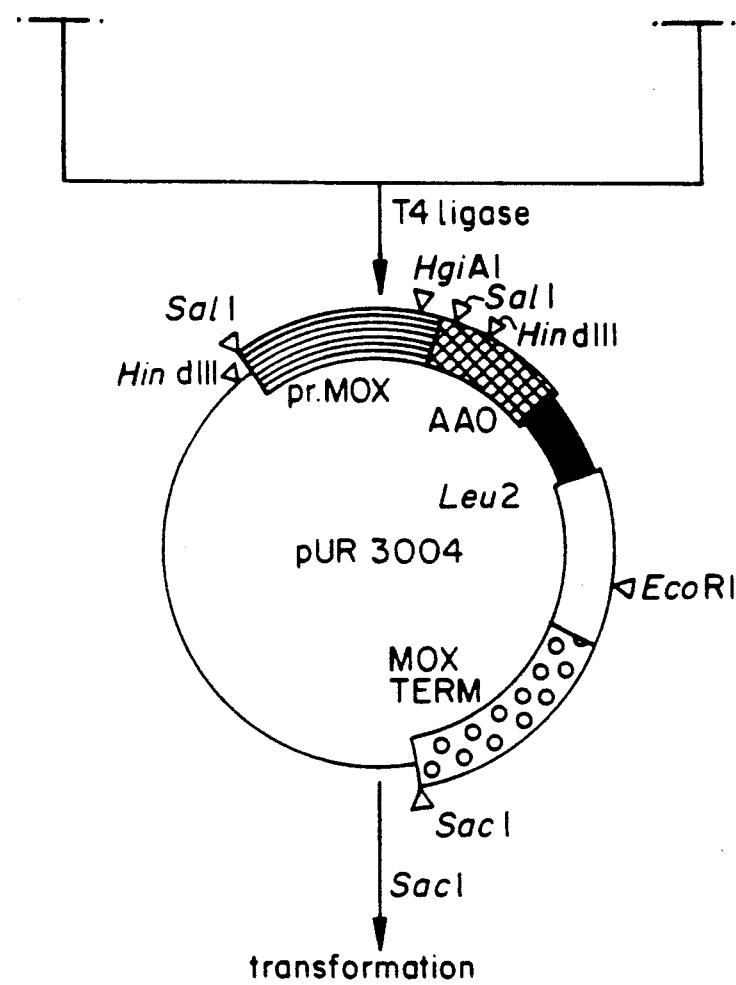

FIG. 13B. The construction of pUR 3004, by which the AAO gene integrates into the chromosomal MOX gene of a *H. polymorpha* leu− derivative. Selection on leu+.

Figure 13C:
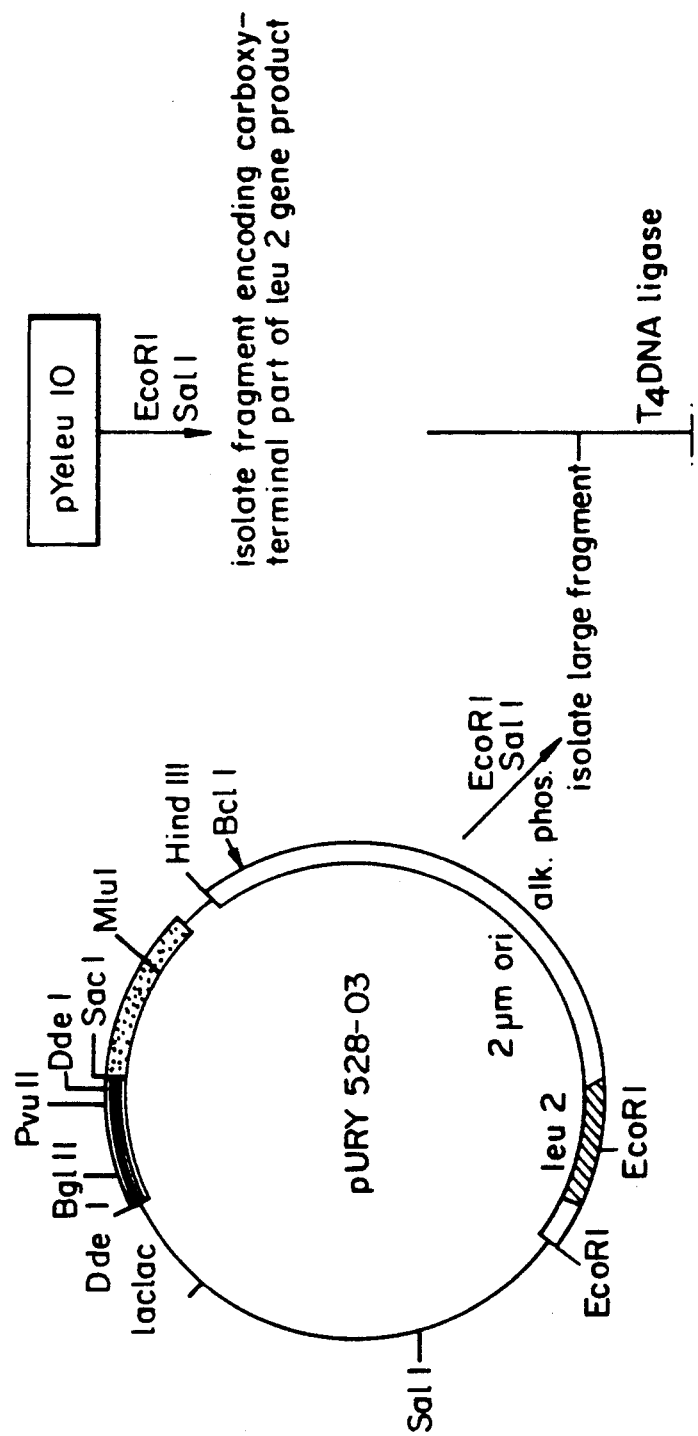
Figure 13C:
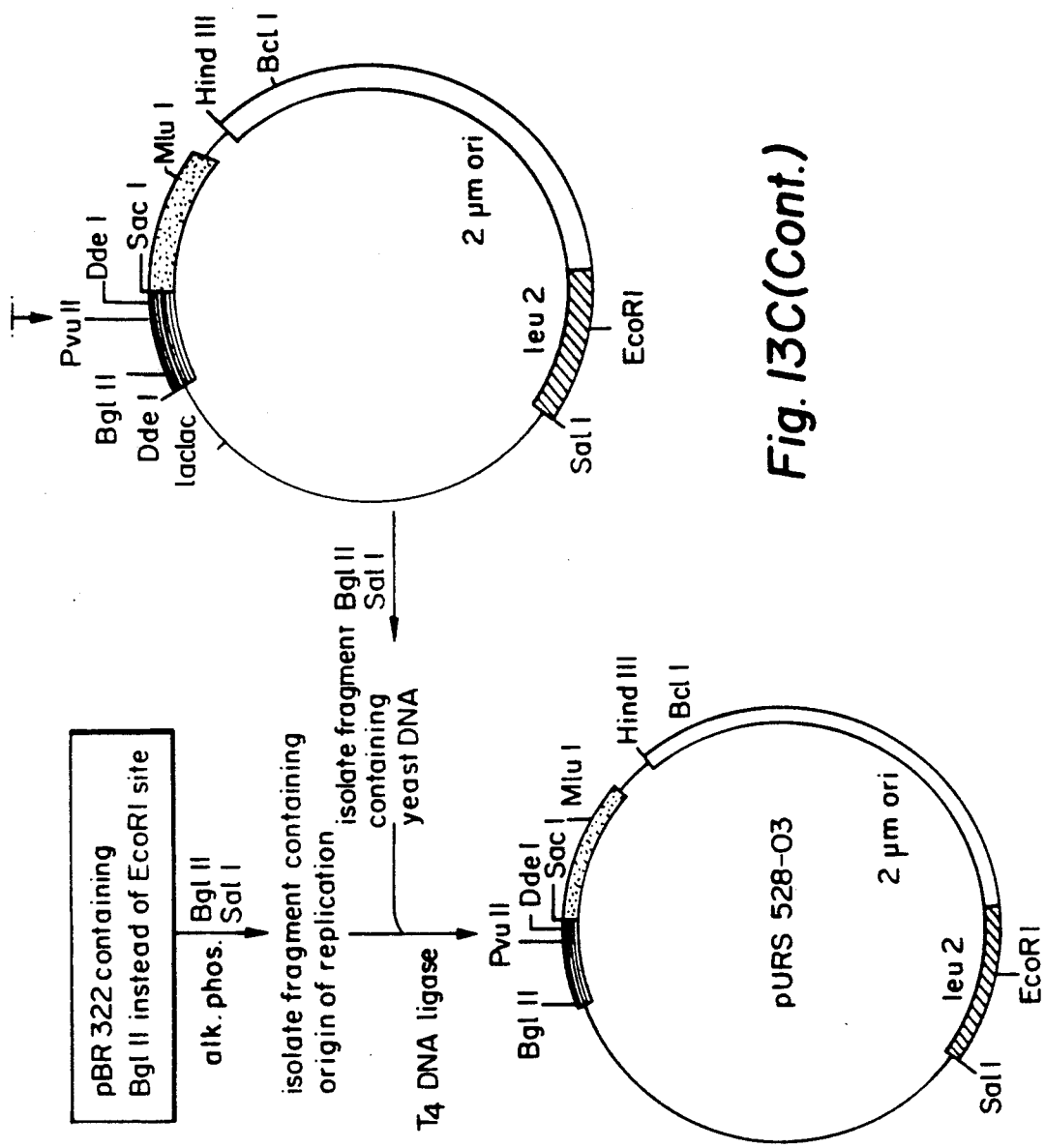

FIG. 13C. The construction of pURS 528-03. Owning to the removal of the pCR1 sequence and the double lac UV5 promoter, this plasmid is about 2.2 kb shorter than pURY 528-03.

FIG. 14. The DNA sequence of the HGRF gene, derived from the published amino acid sequence. The gene is synthesised in the optimal codon use for *H. polymorpha* in oligonucleotides of about 50 nucleotides long. HgiAI, HindIII and SalI sites are used for subcloning. The HgiAI-HindIII fragment forms the adapter between the structural HGRF gene and the MOX promoter. The translational start codon (met) and stop codon (***) are indicated. The structural sequence is numbered from 1 to 140, while the MOX promoter is numbered from −34 to −1.

Figure 15A:
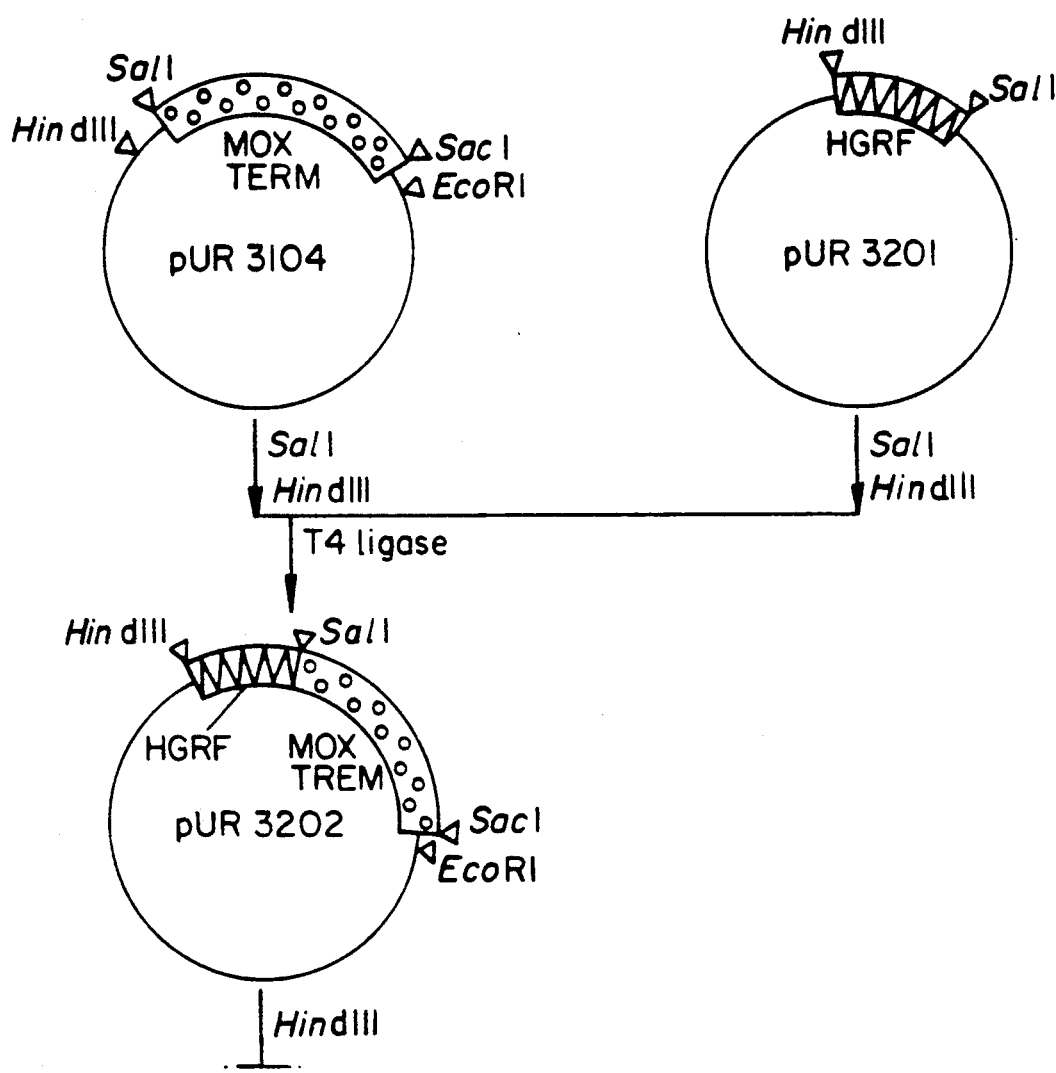
Figure 15A:
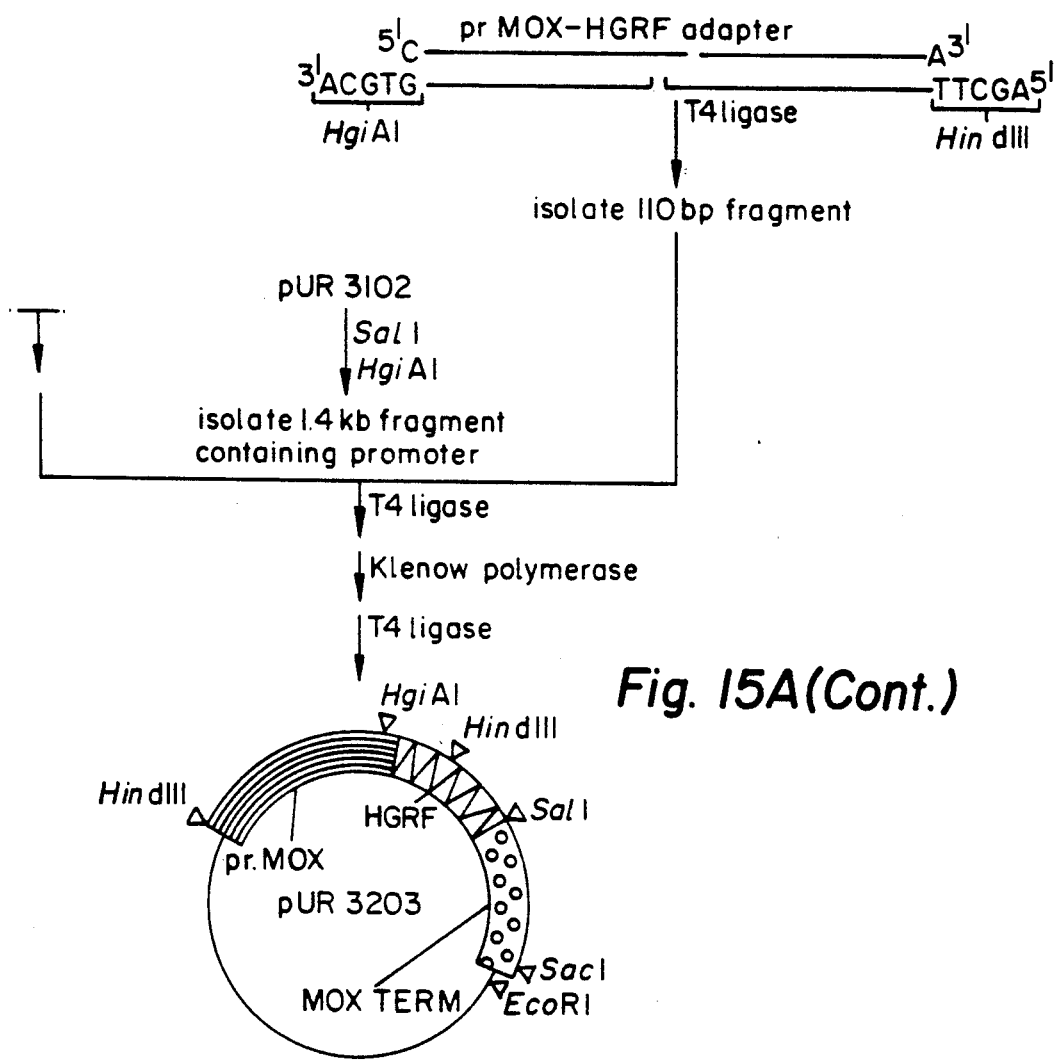

FIG. 15A. The construction of pUR 3203, by which the gene coding for HGRF integrates into the chromosomal MOX gene of *H. polymorpha*. Selection on immunological activity of HGRF.

Figure 15B:
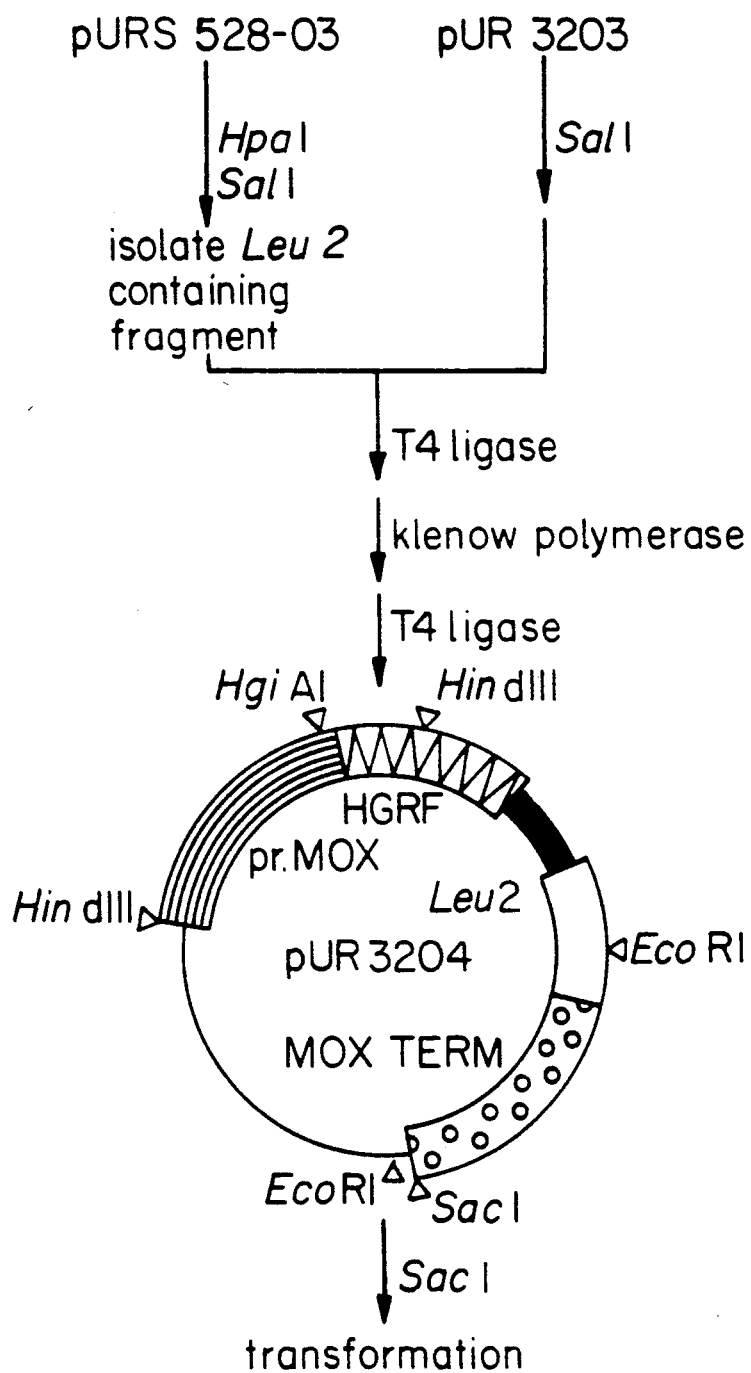

FIG. 15B. The construction of pUR 3204, by which the gene coding for HGRF integrates into the chromosomal MOX gene of a *H. polymorpha* leu− derivative. Selection on leu+.

Figure 15C:
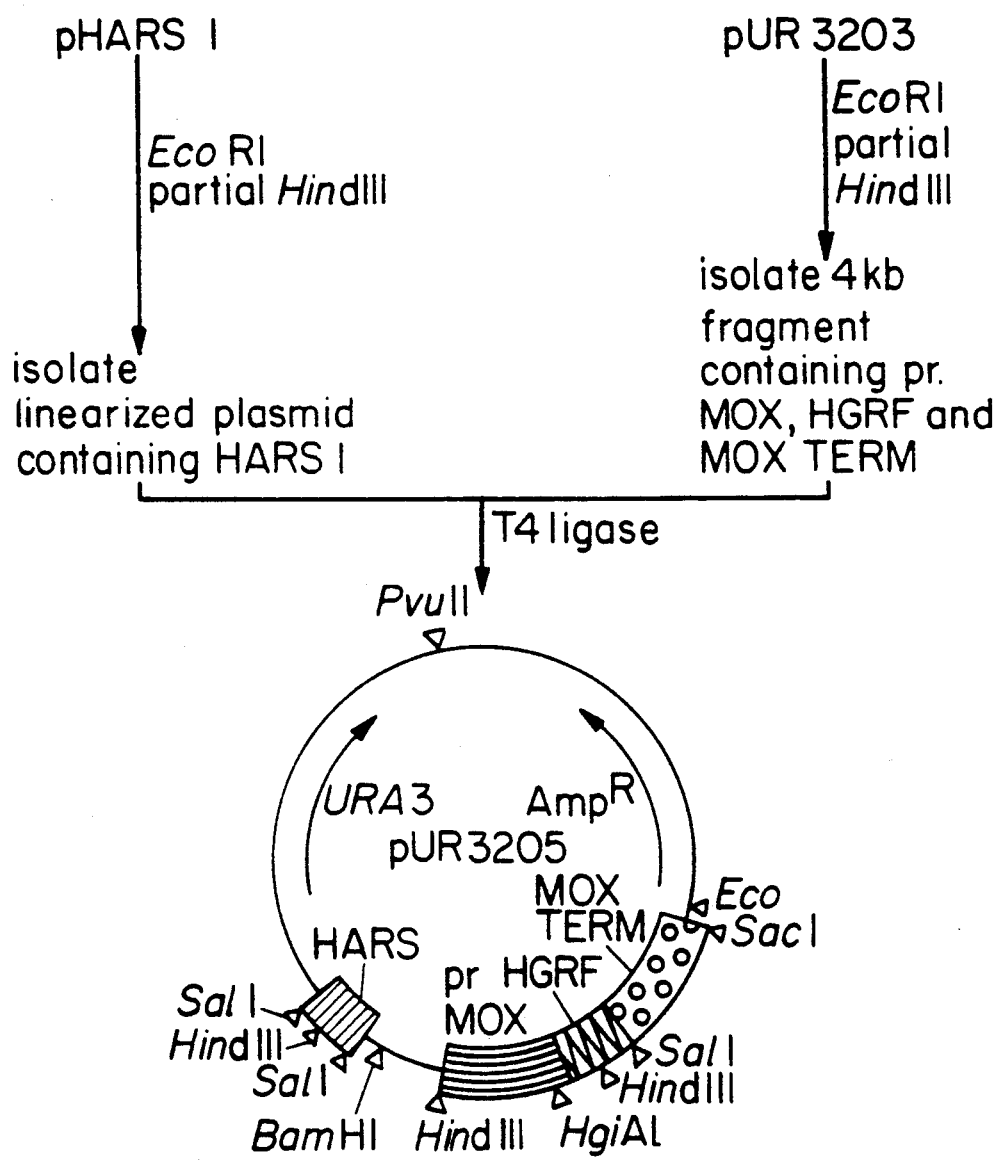

FIG. 15C. The construction of pUR 3205, by which the gene coding for HGRF is inserted into a HARS-1-containing plasmid, which replicates autonomously in *H. polymorpha*. Selection by transformation of a ura− mutant.

Figure 15D:
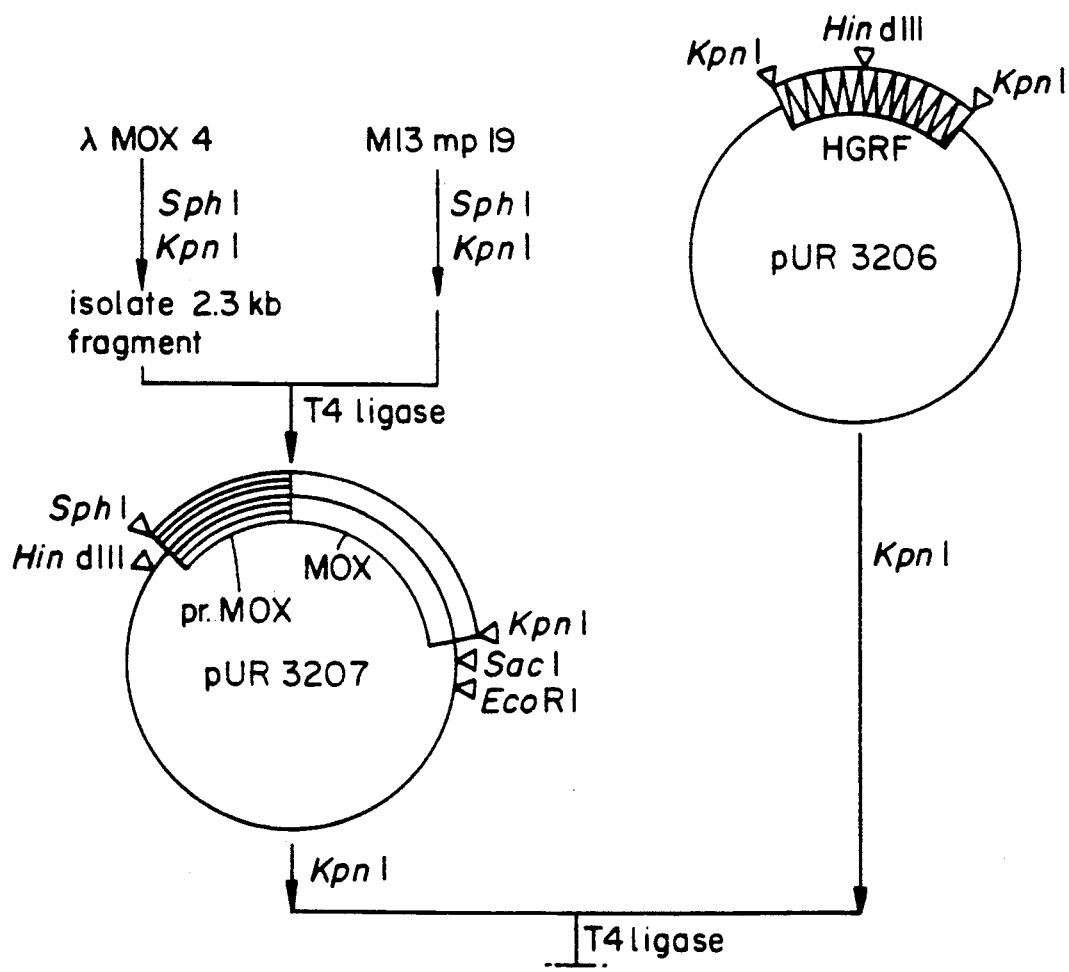
Figure 15D:
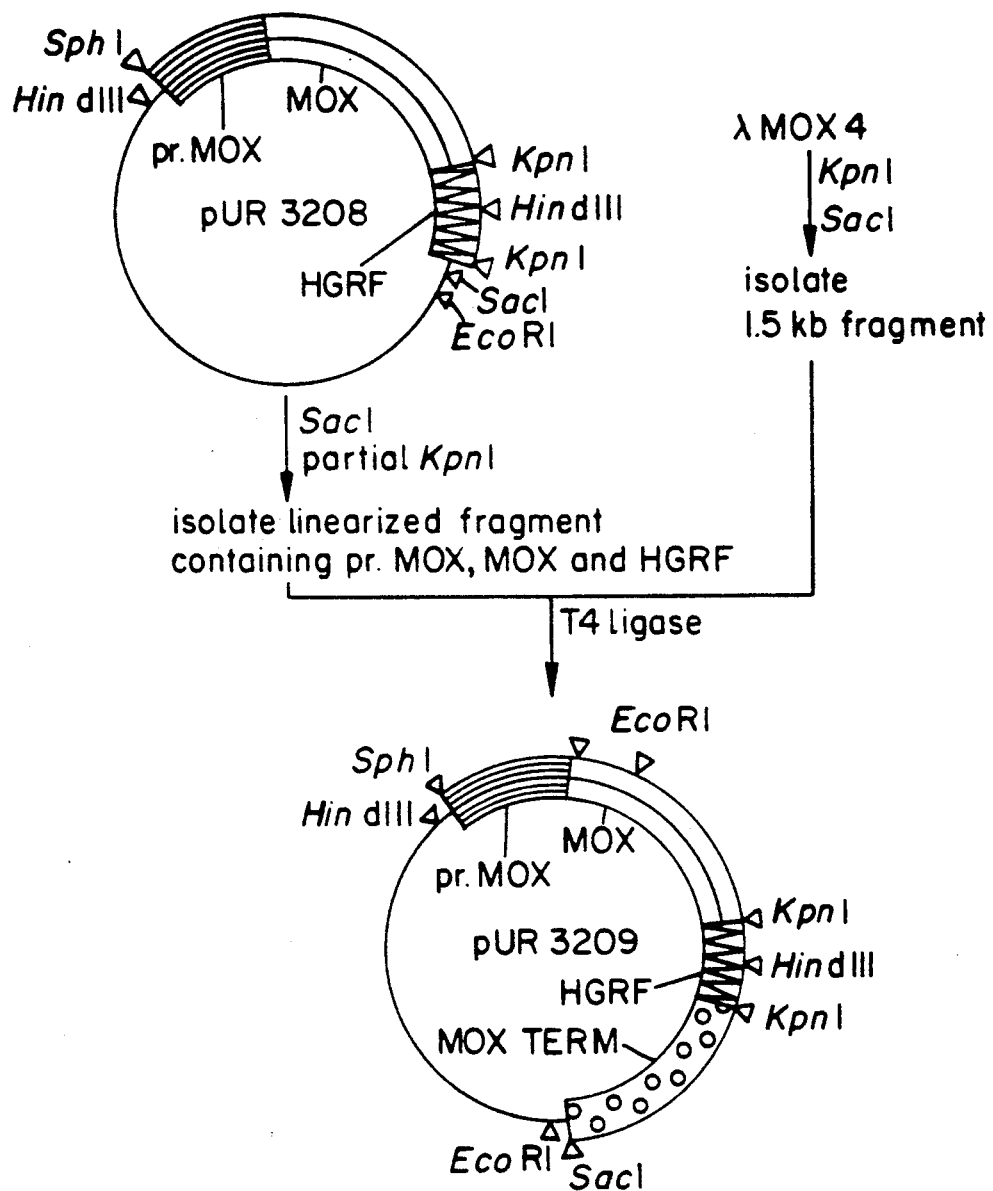

FIG. 15D. The construction of pUR 3209, by which the gene coding for HGRF integrates into the chromosomal MOX gene of *H. polymorpha*, fused to the structural MOX gene. HGRF is cleaved from the fusion protein by CNBr cleavage. Selection on immunological activity of HGRF.

Figure 15E:
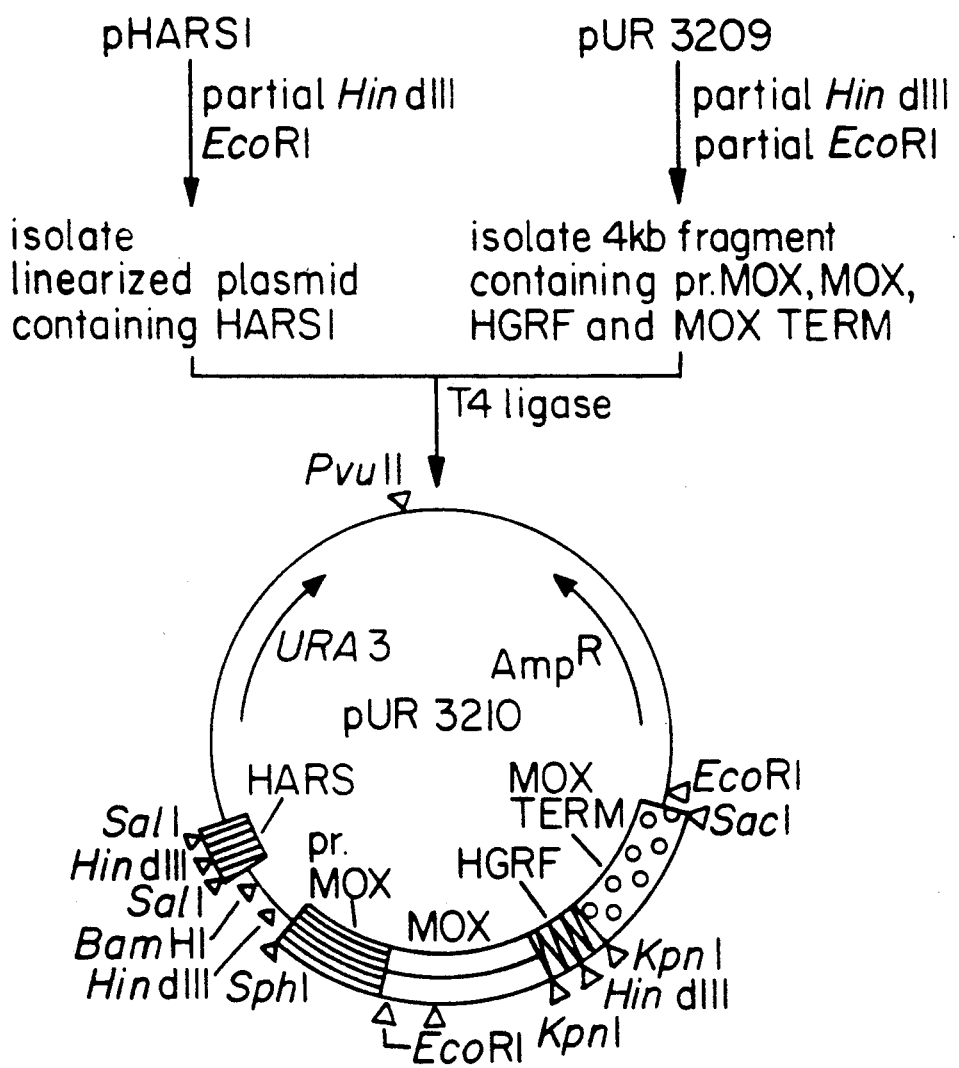

FIG. 15E. The construction of pUR 3210, by which the gene coding for HGRF is inserted into a HARS-1-containing plasmid, fused to the structural MOX gene. Selection as in FIG. 16C.

Figure 15F:
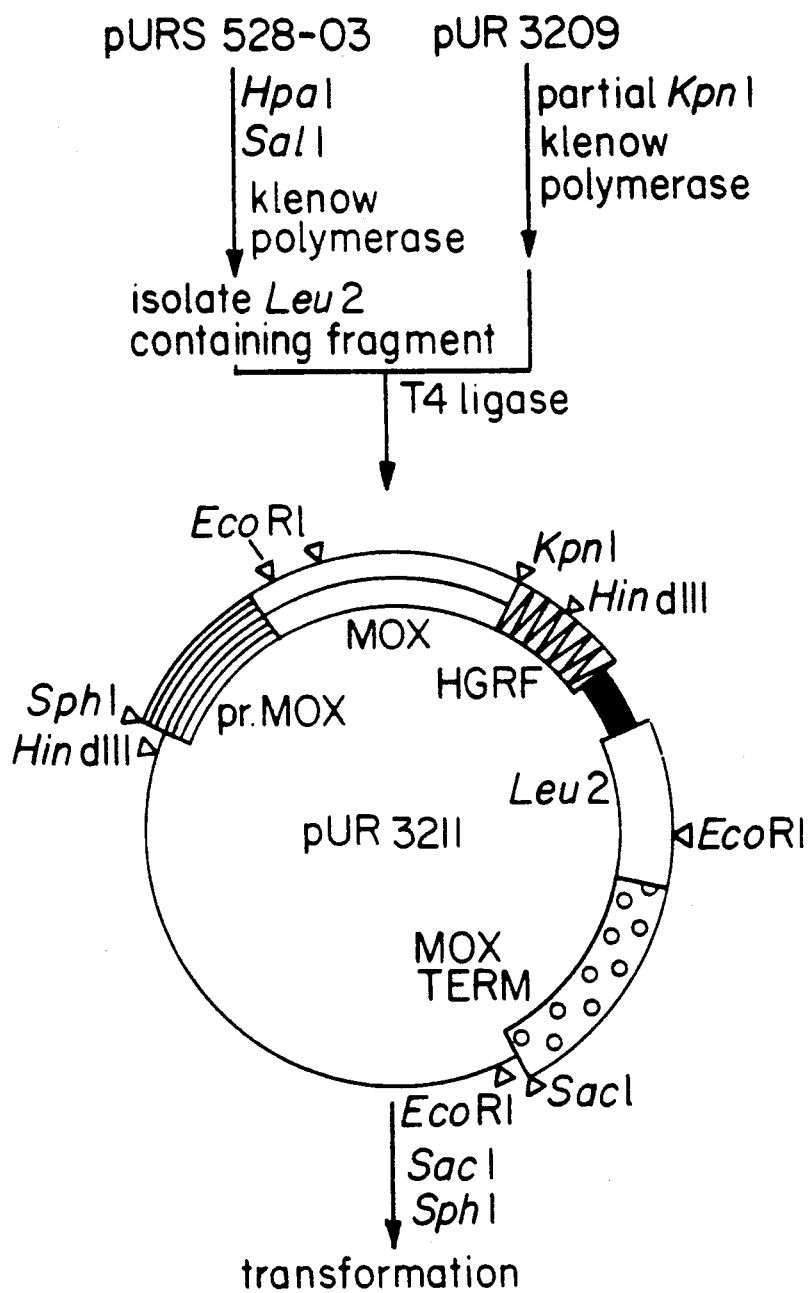

FIG. 15F. The construction of pUR 3211, by which the gene coding for HGRF integrates into the chromosomal MOX gene of a *H. polymorpha* leu− derivative, fused to the structural MOX gene. Selection on leu+.

FIG. 16. The DNA sequence of the HGRF gene, derived from the published amino acid sequence. The gene is synthesised as mentioned in FIG. 15, but constructed in such a way that it could be inserted into the unique KpnI site of the structural MOX gene. Therefore it was equipped with KpnI sites on both sides of the gene, and KpnI-HindIII fragments were used for subcloning. Synthesis will be as a fusion product to the MOX enzyme. The internal met (ATG) at position 82 is converted into a cys (TGT). Translational start (met) and stop (***) codon are indicated.

FIG. 17A-G. The nucleotide sequence of the DAS structural gene and its 5'- and 3'-flanking sequence.

Figures 18A, 18B:
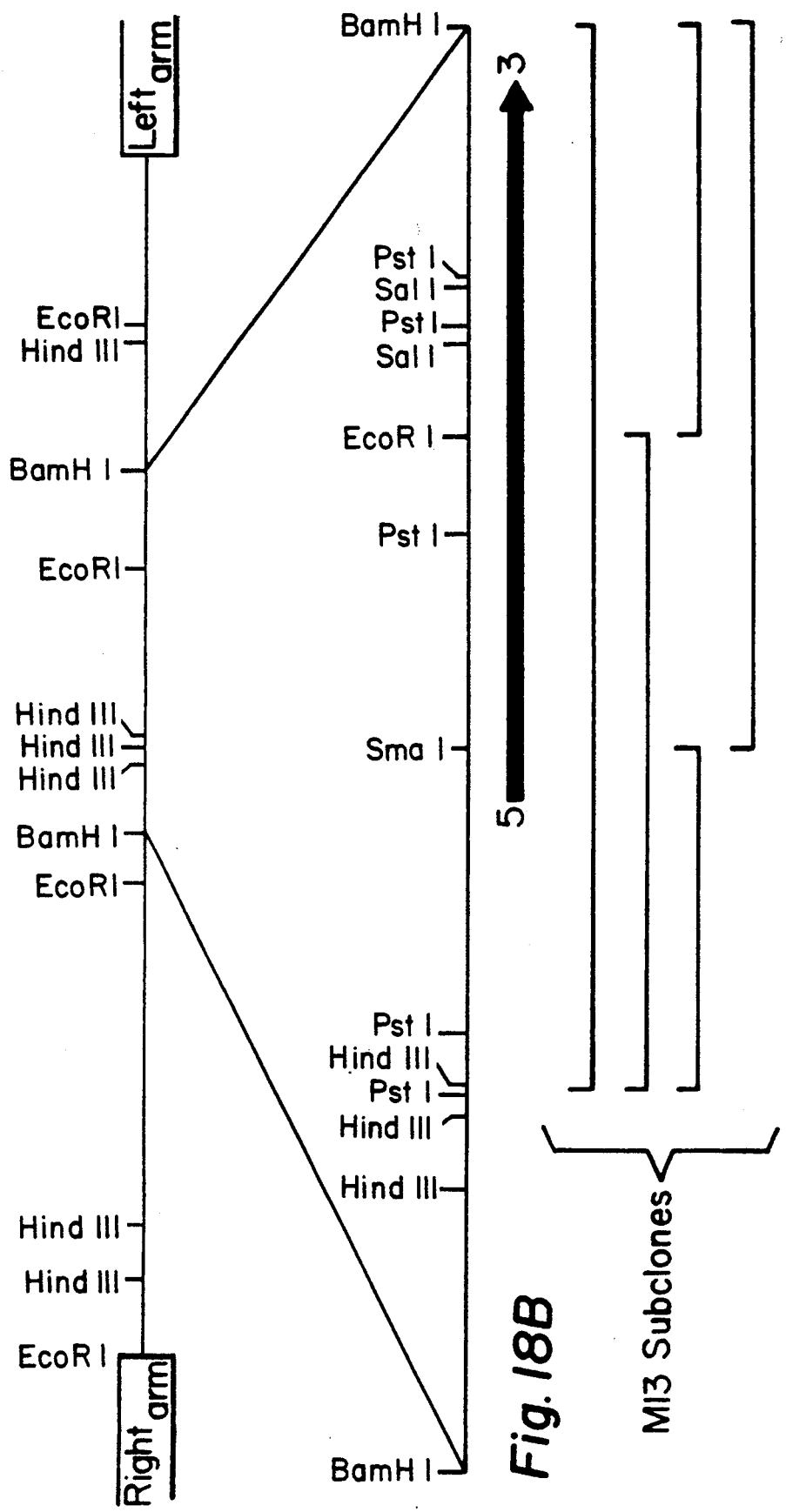

FIG. 18. Restriction map for the DAS-lambda clone. Only relevant restriction sites are indicated that have been used for subcloning and sequencing of the MOX gene. The open reading frame, containing the structural DAS sequence, and the M13 subclones made, are depicted.

FIG. 19. Identical sequences in −1000 region of DAS and MOX genes.

Materials and methods a) Microorganisms and cultivation conditions *Hansenula polymorpha* CBS 4732 was obtained from Dr J.P. van Dijken (University of Technology, Delft, The Netherlands). Cells were grown at 37° C. in 1 liter Erlenmeyer flasks containing 300 ml minimal medium (Veenhuis et al., 1978), supplemented with 0.5% (v/v) methanol or 0.5% (v/v) ethanol as indicated. Phage lambda L47.1 and the P2 lysogenic *E. coli* K12 strain Q 364 were obtained from Dr P. van der Elsen (Free University of Amsterdam, The Netherlands) and propagated as described (Loenen and Brammar, 1980).

*E. coli* K12 strains BHB 2600, BHB 2688 and BHB 2690 (Hohn, 1979) were obtained from Dr M. van Montagu (University of Gent, Belgium), while *E. coli* K12 strain JM 101.7118 and the M13 derivatives M13 mp 8, 9, 18 and 19 were obtained from Bethesda Research Laboratories Inc. (Gaithersburg, MD, U.S.A.).

b) Enzymes

All enzymes used were obtained from Amersham International PLC, Amersham, U.K., except alpha-helicase which was obtained from Pharm Industrie, Clichy, France. Enzyme incubations were performed according to the instructions of the manufacturer. ATP:RNA adenyl transferase was purified as described by Edens et al. (1982).

c) Other materials

[$^{35}$S] methionine, [alpha-$^{35}$S] dATP, [alpha-$^{32}$P] dNTP's, [alpha-$^{32}$P] ATP and [gamma-$^{32}$P] ATP were obtained from Amersham International PLC, Amersham, U.K.

Nitrobenzyloxy-methyl (NBM) paper was obtained from Schleicher and Schuell, and converted into the diazo form (DBM) according to the instructions of the manufacturer.

Nitrocellulose filters (type HATF) were obtained from Millipore.

RNA isolation, fractionation and analysis

*Hansenula polymorpha* cells were grown to mid-Hansenula exponential phase, either in the presence of methanol or ethanol. The cells were disrupted by forcing them repeatedly through a French Press at 16 000 psi, in a buffer containing 10 mM Tris-HCl pH 8, 5 mM MgCl$_2$, 1% NaCl, 6% para-aminosalicylic acid, 1% sodium dodecylsulphate (SDS) and 5% phenol. The purification of polyadenylated RNA was subsequently performed, as described previously (Edens et al., 1982). One gram cells yielded four mg total RNA and 0.1 mg polyadenylated RNA. Five microgram samples of total RNA or polyadenylated RNA were radioactively labelled at their 3'-ends with ATP:RNA adenyl transferase and [alpha-$^{32}$P] ATP, and subsequently separated on a 2.5% polyacrylamide gel containing 7M urea (Edens et al., 1982). For the preparative isolation of a specific mRNA fraction, 40 micrograms polyadenylated RNA was mixed with four micrograms of labelled polyadenylated RNA and separated on the denaturing polyacrylamide gel. The radioactive 2.4 kb RNA class was eluted from slices of the gel and freed from impurities by centrifugation through a 5-30% glycerol gradient in 100 mM NaCl, 10 mM Tris-HCl pH 7.5, 1 mM EDTA and 0.1% SDS for 15 h at 24 000 rev./min. in a Beckmann centrifuge using an SW 60 rotor at 20° C. The radioactive fractions were pooled and precipitated with ethanol. Polyadenylated RNA was translated in vitro in a rabbit reticulocyte lysate according to Pelham and Jackson (1976), using [$^{35}$S] methionine as a precursor. The translation products were immuno-precipitated with MOX antiserum as described by Valerio et al. (1983).

cDNA synthesis

One third of the RNA fraction, isolated from the polyacrylamide gel, was used to procure a radioactive cDNA with reverse transcriptase (Edens et al., 1982). Using [alpha-$^{32}$P] dATP and [alpha-$^{32}$P] dCTP of a high specific activity (more than 3000 Ci/mM), 20 000 cpm of high molecular weight cDNA was formed during 1 h at 42° C. in the presence of human placental ribonuclease inhibitor.

DNA isolation

Ten g of *Hansenula polymorpha* cells were washed with 1M sorbitol and resuspended in 100 ml 1.2M sorbitol, 10 mM EDTA and 100 mM citric acid pH 5.8, to which 100 microliter beta-mercapto-ethanol was added. Cells were spheroplasted by incubation with 500 mg alpha-helicase for 1 h at 30° C. Spheroplasts were collected by centrifugation at 4000 rev./min. in a Sorvall GSA rotor, resuspended in 40 ml 20 mM Tris-HCl pH 8, 50 mM EDTA and lysed by adding 2.5% SDS. Incompletely lysed cells were pelleted for 30 min. at 20 000 rev./min. in a Sorvall SS34 rotor and DNA was isolated from the viscous supernatant by centrifugation using a CsCl-ethidium bromide density gradient at 35 000 rev./min. for 48 h in a Beckmann centrifuge using a 60 Ti rotor. 2 mg of DNA was isolated with a mean length of 30 kb.

Preparation of a clone bank in phage lambda L47.1

150 microgram *Hansenula polymorpha* DNA was partially digested with Sau3AI and sedimented through a 10-40% sucrose gradient in 1M NaCl, 20 mM Tris-HCl pH 8 and 5 mM EDTA for 22 h at 23 000 rev./min. in an SW 25 rotor. The gradient was fractionated and samples of the fractions were separated on a 0.6% agarose gel in TBE buffer (89 mM Tris, 89 mM Boric acid, 2.5 mM EDTA).

Fractions that contained DNA of 5-20 kb were pooled and the DNA was precipitated with ethanol. Phage lambda L47.1 was grown, and its DNA was isolated as described by Ledeboer et al. (1984). The DNA was digested with BamHI and arms were isolated by centrifugation through a potassium acetate gradient as described by Maniatis et al. (1982). Two microgram phage lambda DNA arms and 0.5 /µg Sau3AI digested *Hansenula polymorpha* DNA thus obtained were ligated and packaged in vitro using a protocol from Hohn (1979). Phages were plated on *E. coli* strain Q 364 to a plaque density of 20,000 pfu per 14 cm Petri dish. Plaques were blotted onto a nitrocellulose filter (Benton and Davis, 1977) and the blot was hybridized with the radioactive cDNA probe isolated as described above. Hybridization conditions were the same as described by Ledeboer et al. (1984) and hybridizing plaques were detected by autoradiography.

Isolation and partial amino acid sequence analysis of alcohol oxidase (MOX)

*Hansenula polymorpha* cells grown on methanol were disintegrated by ultrasonification and the cell debris was removed by centrifugation. The MOX-containing protein fraction was isolated by $(NH_4)_2SO_4$ precipitation, (40-60% saturation). After dialysis of the precipitate, MOX was separated from catalase and other proteins by ion-exchange chromatography (DEAE-Sepharose) and gel filtration (Sephacryl S-400). Antibodies against MOX were raised in rabbits by conventional methods using complete and incomplete Freund's adjuvants (Difco Lab, Detroit, U.S.A.). Sequence analysis of alcohol oxidase treated with performic acid was performed on a Beckman sequenator. Identification of the residues was done with HPLC. The amino acid composition was determined on a Chromaspek analyser (Rank Hilger, U.K.), using standard procedures and staining by ninhydrin. The carboxy terminal amino acid was determined as described by Ambler (1972).

Chemical synthesis of deoxyoligonucleotides

Deoxyoligonucleotides were synthesized on a Biosearch SAM I gene machine, using the phosphite technique (Matteucci and Caruthers, 1981). They were purified on 16% or 20% polyacrylamide gels in TBE.

Hybridization with deoxyoligonucleotide probes

The deoxyoligonucleotides were radioactively labelled with T4-polynucleotide kinase and [gamma-$^{32}$P] ATP. The DNA of the MOX clones obtained was digested with different restriction enzymes, separated on 1% agarose gel and blotted onto DBM paper. Hybridizations were performed as described by Wallace et al. (1981).

DNA sequence analysis

From clone 4 (see Example 1) containing the complete MOX gene, several subclones were made in phage M13mp-8, -9 or M13mp-18, -19 derivatives by standard techniques. Small subclones (less than 0.5 kb), cloned in two orientations, were sequenced directly from both sides. From the larger subclones, also cloned in two orientations, sequence data were obtained by an exonuclease Bal31 digestion strategy (see FIG. 1). For each of both cloned orientations the RF M13 DNA is digested with a restriction enzyme that preferably cleaves only in the middle of the insert. Subsequently, both orientations of the clones were cut at this unique site, and digested with exonuclease Bal31 at different time intervals. Incubation times and conditions were chosen such that about 100-150 nucleotides were eliminated during each time interval. Each fraction was digested subsequently with the restriction enzyme, recognizing the restriction site situated near the position at which the sequence reaction is primed in the M13 derivatives. Ends were made blunt end by incubation with T4-polymerase and all dNTP's, and the whole mix was ligated under diluted conditions, thereby favouring the formation of internal RF molecules. The whole ligation mix was used to transform to *E. coli* strain JM 101-7118.

From each time interval several plaques were picked up and sequenced using recently described modifications of the Sanger sequencing protocol (Biggin et al., 1983).

The isolation of auxotrophic mutants

LEU-1 (CBS N° 7171) is an auxotrophic derivative of H. polymorpha strain NCYC 495 lacking β-isopropylmalate dehydrogenase activity. The isolation of this mutant has been described by Gleeson et al. (1984).

LR9 (CBS N° 7172) is an auxotrophic derivative of H. polymorpha ATCC 34438, lacking orotidine 5′-decarboxylase activity.

For the isolation, all procedures were carried out at 30° C. instead of 37° C., which is the optimal temperature for growth of this yeast. Yeast cells were mutagenized with 3% ethylmethanesulphonate for 2 hr (Fink, 1970). The reaction was stopped with 6% sodium thiosulphate (final concentration) and the solution was incubated for another 10 min. Mutagenized cells were then washed once with $H_2O$ and incubated for 2 days on YEPD or YNB supplemented with uracil for segregation and enrichment of uracil-auxotrophs followed by a 15 hr cultivation on MM without nitrogen source. Finally a nystatin enrichment was employed for 12 hr on MM with a concentration of 10 /μg antibiotic per ml. The treated cells were plated on YNB plates containing 200 /μg uracil per ml and 0.8 mg 5-fluoroorotic acid (Boeke et al., 1984). Usually $10^6$ cells were plated on a single plate. Resistant colonies were picked after 3 days of incubation, replica plated twice on YNB plates to establish the auxotrophy. From the auxotrophic mutants ura⁻ cells were isolated. Alternatively, $1.5 \times 10^6$ yeast cells were incubated in one ml of YNB liquid medium supplemented with 200 /μg of uracil and 0.8 mg of 5-fluoroorotic acid. After incubation of 2 days, the treated cells were plated on YNB containing uracil, replica-plated twice on YNB and analysed as described above. Such resistant mutants have been shown to be uracil auxotrophs affected at the URA3 or the URA5 locus in S. cerevisiae (F. Lacroute, personal communication). Of about 600 resistant colonies of H. polymorpha tested, 52 exhibited a uracil phenotype. Since URA3 and URA5 mutations in S. cerevisiae lack orotidine 5′-decarboxylase and orotidine 5′-phosphate pyrophosphorylase, respectively (Jones and Fink, 1982), the obtained uracil auxotrophs of H. polymorpha were tested for both enzymatic activities (Lieberman et al., 1955). Mutants affected in either of the two enzymes were found (Table I). They have been designated odcl and oppl mutants, respectively. The odcl mutants exhibit adequate low reversion frequencies (Table II) and thus are suitable for transformation purposes by complementation.

TABLE I

Activities of orotidine 5′-phosphate decarboxylase and orotidine 5′-phosphate pyrophosphorylase in H. polymorpha mutants requiring uracil for growth.

| Strain/Genotype | Reversion rate | Orotidine 5′-phosphate decarboxylase Activity (%)[a] | Orotidine 5 phosphate pyrophosphorylase Activity (%)[a] |
|---|---|---|---|
| Wild type | — | 100 | 100 |
| LR 9/odcl | <2 × 10⁹ | <1 | 106 |
| MR 7/odcl | 6 × 10⁷ | <1 | 71 |
| NM 8/odcl | 3 × 10⁸ | <1 | 105 |
| CLK 55/oppl | n.e.[b] | 90 | <1 |
| CLK 68/oppl | n.e. | 82 | <1 |

TABLE I-continued

Activities of orotidine 5′-phosphate decarboxylase and orotidine 5′-phosphate pyrophosphorylase in H. polymorpha mutants requiring uracil for growth.

| Strain/Genotype | Reversion rate | Orotidine 5′-phosphate decarboxylase Activity (%)[a] | Orotidine 5 phosphate pyrophosphorylase Activity (%)[a] |
|---|---|---|---|
| YNN 27/ura3 | n.e. | 0 | n.e. |

Strains were grown in YEPD until late exponential phase. Extraction of cells was performed with glass beads using a Braun homogenizer. Protein was estimated by the optical density at 280 nm.
[a]Expressed as the percentage of wild type activity.
[b]Not estimated.

TABLE II

Transformation of uracil-requiring mutants of H. polymorpha

| Strain | Plasmid | Transformation frequency[a] | Stability[b] (%) | Status of transformed DNA |
|---|---|---|---|---|
| LR 9 | YRP17 | 2.2 × 10² | <1 | Autonomous replication |
| LR 9 | pHARS1 | 1.5 × 10³ | 2 | Autonomous replication |
| LR 9 | pHARS2 | 4.6 × 10² | 1.5 | Autonomous replication |
| LR 9 | YIP5 | 3 (38)[c] | 105 | Integration |
| LR 9 | pRB58 | 0 | — | — |
| LR 9 | pHH85 | 0 | — | — |
| YNN 27 | YIP5 | 0 | — | — |

[a]Expressed as total number per μg of DNA. Intact cells treated with polyethyleneglycol were used for transformation as described in Materials and Methods.
[b]Expressed as the percentage of remaining uracil prototrophs after growth on YEPD for ten generations.
[c]Number in parentheses indicates the amount of mini-colonies containing free plasmid YIP5.

Isolation of au replication sequences (HARS) from H. polymorpha

Chromosomal DNA from H. polymorpha was partially digested either with SalI or BamHI and ligated into the single SalI and BamHl site of the integrative plasmid YIp5, respectively. The ligation mixture was used to transform E. coli 490 to ampicillin resistance. YIp5 is an integrative plasmid containing the URA3 gene as a selective marker (Stinchcomb et al., 1980).

The plasmid pool of H. polymorpha SalI clones was used to transform H. polymorpha mutant LR9. A total of 27 transformants was obtained being also positive in the β-lactamase assay. From all of them, plasmids could be recovered after transformation of E. coli 490 with yeast minilysates. Restriction analysis of the plasmids revealed that most of the inserts show the same pattern. The two different plasmids, pHARS1 and pHARS2, containing inserts of 0.4 and 1.6 kb respectively, were used for further studies (FIG. 2). Both plasmids transform H. polymorpha mutant LR9 with a frequency of about 500–1,500 transformants per /μg of DNA using the transformation procedure of intact cells treated with polyethyleneglycol. Southern analysis of the H. polymorpha transformants after retransformation with pHARS1 and pHARS2 recovered from E. coli plasmid preparations shows the expected plasmid bands and thus excludes integration of the URA3 gene as a cause of the uracil protrophy. Therefore, we conclude that the HARS sequences like ARS1 (Stinchcomb et al., 1982) allow autonomous replication in H. polymorpha. Neither HARS1 nor HARS2 enabled autonomous replication in S. cerevisiae. HARS1 was sequenced completely.

Estimation of plasmid copy number in *H. polymorpha* transformants

The copy number of plasmids conferring autonomous replication in *H. polymorpha* either by ARS sequences or by HARS sequences was estimated by Southern blot analysis (FIG. 3). For comparison, plasmid YRP17 in *S. cerevisiae* (FIG. 3, lanes 6, 7), which has a copy number of 5-10 per cell (Struhl et al., 1979) and the high copy number plasmid pRB58 in *S. cerevisiae* (FIG. 3, lanes 4, 5) with about 30-50 copies per cell were used. YRP17 is a URA3-containing yeast plasmid, bearing an ARS sequence (Stinchcomb et al., 1982), while pRB58 is a 2 /μm derivative containing the URA3 gene (Carlson and Botstein, 1982). A *Kluyveromyces lactis* transformant carrying 2 integrated copies of pBR pBR322 was used as a control (FIG. 3, lanes 2, 3). The intensity of staining in the autoradiogram reveals that the plasmid YRP17 in *H. polymorpha* has practically the same copy number as in *S. cerevisiae*, whereas plasmids pHARS-1 and pHARS-2 show a copy number which is in the range of about 30-40 copies per cell like pRB58 in *S. cerevisiae*. This proves once more the autonomously replicating character of the HARS sequence.

Transformation procedures

Several protocols were used.

a) *H. polymorpha* strain LEU-1 was transformed using a procedure adapted from Beggs (1978). The strain was grown at 37° C. with vigorous aeration in 500 ml YEPD liquid medium up to an OD$_{600}$ of 0.5. The cells were harvested, washed with 20 ml distilled water and resuspended in 20 ml 1.2M sorbitol, 25 mM EDTA pH 8.0, 150 mM DTT and incubated at room temperature for 15 minutes. Cells were collected by centrifugation and taken up in 20 ml 1.2M sorbitol, 0.01M EDTA, 0.1M sodium citrate pH 5.8 and 2% v/v beta-glucuronidase solution (Sigma 1500000 units/ml) and incubated at 37° C. for 105 minutes. After 1 hr, the final concentration of beta-glucuronidase was brought to 4% v/v. For transformation, 3 ml aliquots of the protoplasts were added to 7 ml of ice cold 1.2M sorbitol, 10 mM Tris-HCl pH 7. Protoplasts were harvested by centrifugation at 2000 rpm for 5 minutes and washed three times in ice cold sorbitol buffer. Washed cells were resuspended in 0.2 ml 1.2M sorbitol, 10 mM CaCl$_2$, 10 mM Tris-HCl pH 7 on ice. 2 /μg of YEP13 DNA - an autonomous replicating *S. cerevisiae* plasmid consisting of the LEU2 gene of *S. cerevisiae* and the 2 micron-ori (Broach et al., 1979)—were added to 100 ml of cells and incubated at room temperature. 0.5 ml of a solution of 20% PEG 4000 in 10 mM CaCl$_2$, 10 mM Tris-HCl pH 7.5 was added and the whole mixture was incubated for 2 minutes at room temperature. Cells were collected by brief (5 sec.) centrifugation in an MSG microfuge set at high speed and resuspended in 0.1 ml YEPD 1.2M sorbitol pH,7.0, and incubated for 15 minutes at room temperature. The cells were plated directly by surface spreading on plates containing 2% Difco agar, 2% glucose, 0.67% Difco yeast nitrogen base and 20 mg/1 of each of L-adenine Hemisulphate, methionine, uracil, histidine, tryptophan, lysine and 1.2M sorbitol. Leu+ transformants appear after 5 days incubation at 37° C. with a frequency of 50 colonies//ug DNA, while no transformants appear if no DNA is added.

b) Alternatively, *H. polymorpha* LEU-1 was transformed with YEP13, using a procedure adapted from Das et al. (1984). Exponentially growing cells were grown up to an OD$_{600}$ of 0.4, washed in TE buffer (50 mM Tris-HCl pH 8.0, 1 mM EDTA) and resuspended in 20 ml TE buffer. 0.5 ml cells were incubated with 0.5 ml 0.2M LiCl for 1 hr at 30° C. To 100 ml of these cells 4 /μg YEP13 in 20 ml TE buffer was added and the sample was incubated for a further 30 minutes at 30° C. An equal volume of 70% v/v PEG 4000 was added and the mixture was incubated for 1 hr at 30° C., followed by 5 min. at 42° C. After addition of 1 ml H$_2$O, cells were collected by a brief centrifugation as described under a), washed twice with H$_2$O and resuspended in 0.1 ml YEPD 1.2M sorbitol and incubated for 15 minutes at room temperature. Cells were plated as described. Leu+ transformants appear with a frequency of 30//μg DNA.

c) The *H. polymorpha* URA mutant LR9 was transformed with YRP17, a plasmid containing the URA3 gene of *S. cerevisiae* as a selective marker and an autonomously replicating sequence (ARS) for *S. cerevisiae* (Stinchomb et al, 1982). Using the protoplast method described by Beggs (1978), 2-5 transformants//μg DNA were obtained. This number was enlarged, using the LiSO$_4$ method of Ito et al. (1983), up to 15-20 transformants per /μg of DNA. However, the best procedure was the procedure described by Klebe et al. (1983), using intact cells treated with PEG 4000. Up to 300 transformants were obtained per /μg DNA. The LiSO$_4$ procedure, as well as the Klebe procedure, was performed at 37° C.

Transformation of *H. polymorpha* based on autonomous replication of the vector was indicated by two characteristics (1) the instability of the uracil+ phenotype. After growth of transformants on YEPD for ten generations, more than 99% had lost the ability to grow on selective medium (Table II). (2) Autonomous replication was further ascertained by transforming *E. coli* cells with yeast minilysates and retransformation of *H. polymorpha*. Subsequent Southern analysis showed the presence of the expected plasmid.

*H. polymorpha* LR9 could not be transformed with pRB58, or with pHH85, constructed by insertion of the whole 2 micron circle DNA (Hollenberg, 1982) into the PstI site of the ampicillin gene of plasmid YIP5. YIP5, containing the DNA sequence of HARS1 or HARS2, was transferred to *H. polymorpha* LR9 using the Klebe protocol with a frequency of 500-1500 transformants per /μg of DNA. Thus, transformation frequency is 2-5 times higher than described above, using the heterologous ARS 1 in YRP17 of *S. cerevisiae*. Similarly, the stability of the HARS plasmid in transformants is slightly higher than the ARS 1 plasmid (Table II).

Transformation of *H. polymorpha* by integration of the URA3 gene from *S. cerevisiae*

The URA3 gene of *S. cerevisiae* shows no homology to the ODC gene in *H. polymorpha*, as revealed by Southern hybridisation of nick-translated YIp5 plasmid DNA to chromosomal DNA of *H. polymorpha*. Therefore, low-frequency integration of the URA3 gene at random sites of the *H. polymorpha* genome had to be anticipated. Transformation of mutant LR9 with the integrative vector YIp5 resulted in 30-40 colonies per /μg of DNA on YNB plates using the polyethyleneglycol method, whereas no transformants were obtained in the control experiment using YIp5 for transformation of *S. cerevisiae* mutant YNN27. Analysis of 38 transformants revealed 4 stable integrants after growth on non-selective medium. The integration event was further demonstrated by Southern analysis (FIG. 4).

A second procedure for generating integration of the URA3 gene into chromosomal DNA of *H. polymorpha* was performed by enrichment of stable Ura+ transformants from transformants carrying plasmid pHARS1. Transformants were grown in liquid YEPD up to a density of $10^9$ cells per ml. An aliquot containing $5 \times 10^6$ cells was used to inoculate 100 ml of fresh medium and was grown up to a cell density of $10^9$ per ml. The procedure was repeated until about 100 generations had been reached. Since the reversion rate of mutant LR9 is $2 \times 10^{-9}$ and the frequency of plasmid loss per 10 generations is 97% in pHARS1 transformants, the predominant part of the Ura+ cells after 100 generations should be integrants. The Ura+ colonies tested were all shown to maintain a stable Ura+ phenotype indicating an integration of the URA3 gene. This was further verified by Southern blot analysis. In addition, these data indicate that the integration frequency is $5 \times 10^6$.

Example 1

CLONING OF THE GENE FOR ALCOHOL OXIDASE (MOX) FROM HANSENULA POLYMORPHA

Characterization of polyadenylated RNA

Total RNA and polyadenylated RNA, isolated from cells grown on methanol, were labelled at their 3'-termini with ATP:RNA adenyl transferase, and separated on a denaturing polyacrylamide gel (FIG. 5). Apart from the rRNA bands, two classes of RNA appear in the poly-adenylated RNA lane, respectively 1 kb and 2.3 kb in length. Since these RNA classes are not found in polyadenylated RNA of ethanol-grown cells (result not shown), they obviously are transcripts of genes derepressed by growth on methanol. The 2.3 kb class can code for a protein of 700 to 800 amino acids, depending on the length of the non-translated sequences. Likewise, the 1 kb class codes for a protein of 250-300 amino acids. Enzymes that are derepressed by growth on methanol and are 700 to 800 amino acids long, most likely are MOX (Kato et al., 1976; Roa and Blobel, 1983) and DHAS (Bystrykh et al., 1981). Derepressed enzymes in the 250 to 300 amino acid range are probably formaldehyde and formate dehydrogenase (Schütte et al., 1976). The polyadenylated RNA was characterized further by in vitro translation in a reticulocyte cell free translation system. Two microliters of the polyadenylated RNA directed protein mixture were separated directly on a 10% SDS polyacrylamide gel, while the remaining 18 microliters were subjected to immuno-precipitation with antiserum against MOX (FIG. 6). Six strong bands dominate in the total protein mixture, having molecular weights of respectively 78kd, 74kd, 58kd, 42kd, 39kd and 36kd. Essentially the same molecular weights were found by Roa and Blobel (1983) in a total cell extract from methanol-grown *H. polymorpha* cells.

The 74kd protein can tentatively be assigned to the monomer of MOX, the 58kd protein to the monomer of catalase and the 39kd and 36kd proteins to the monomers of formaldehyde dehydrogenase and formate dehydrogenase, respectively. The 78kd polypeptide possibly is DHAS, while the 42kd polypeptide remains unidentified. After immuno-precipitation, both high molecular weight proteins react with the MOX antiserum.

Cloning of the gene for MOX

Although the 2.3 kb mRNA class induced by growth on methanol obviously codes for at least 2 polypeptides, it seemed a good candidate for screening a *Hansenula polymorpha* clone bank by hybridization. The 5-20 kb fraction of partially Sau3AI digested *H. polymorpha* DNA was cloned in phage lambda L47.1.

Per microgram insert DNA, 300 000 plaques were obtained while the background was less than 1:1000. Two Benton Davis blots, containing about 20 000 plaques each, were hybridized with 15 000 cpm of the mRNA-derived cDNA probe. After 3 weeks of autoradiography about 40–50 hybridizing plaques could be detected. All plaques were picked up and five were purified further by plating at lower density and by a second hybridization with the cDNA probe. From four, single hybridizing plaques (1, 3, 4, 5) DNA was isolated. The insert length varied from 8 to 13 kb.

Hybridization selection using organic-synthetic DNA probes

The sequence of 30 amino acids at the amino terminus of purified MOX was determined (FIG. 7).

Using the most abundant codon use for the yeast *S. cerevisiae*, a sequence of 14 bases could be derived from part of this protein sequence, with only one ambiguity. Both probes, indicated in FIG. 3, were synthesised. In both probes an EcoRI site is present. DBM blots were made from the DNA of the MOX clones digested with the restriction enzymes BamHI, EcoRI/HindIII, HindIII/SalI and PstI/SalI and separated on 1.5% agarose gels. After hybridization of the blot with a mixture of both radioactively labelled probes, the clones 1, 4 and 5 hybridize, while clone 3 does not, as shown for the HindIII/SalI blot in FIG. 8. However, the probes did not hybridize with the EcoRI/HindIII digested DNA of these clones (result not shown). Since an EcoRI site is present in the probes, the hybridizing DNA in the clones probably is cut by this enzyme too. Consequently the hybridization overlap has become too small to allow the formation of stable hybrids.

Restriction map and sequence analysis

By comparing restriction enzyme digests and by cross-hybridization experiments it was concluded that clones 1, 4 and 5 covered identical stretches of DNA.

In order to definitely establish the nature of this stretch of cloned DNA the insert of clone 4 was analyzed in detail. Hybridization with the amino terminal probe showed that the complete MOX gene (ca. 2 kb) was present, including 2 kb sequences upstream and 3.5 kb downstream (FIG. 9).

DNA sequence analysis of the smallest EcoRI fragment revealed the nucleotide sequence corresponding to the amino terminus of MOX as was determined by amino acid sequence analysis.

For sequence analysis, several fragments were subcloned in M13mp8/M13mp9 or M13mp18/M13mp19 respectively in two orientations, as indicated in FIG. 9. Clones that were smaller than 0.5 kb were sequenced directly from both sides. The larger clones were cut at the unique restriction sites situated in the middle of the cloned fragment, to allow generation of exonuclease Bal31 digested subclones as described in materials and methods. Using specific oligonucleotide primers, sequences around the restriction sites used for subcloning and sequences that did not allow an unequivocal sequence determination were sequenced once more, using the 5.5 kb BamHI/SacI subclone that covers the whole sequence. The complete nucleotide sequence is given in FIG. 10A and 10B.

The sequence contains an open reading frame of 2046 nucleotides that can code for a protein of 664 amino acids. The last codon of the open reading frame codes for Phe, which is in agreement with the carboxy terminus of purified MOX. The amino acid composition derived from the DNA sequence encoding this protein, and the amino acid composition of purified MOX are virtually identical (Table III). The only important differences involve the serine and threonine residues, which are notoriously difficult to determine.

TABLE III

| Amino acid composition of MOX | | |
|---|---|---|
| Amino Acid | DNA sequence | Hydrolysate[a] |
| PHE | 31 | 32 |
| LEU | 47 | 49 |
| ILE | 34 | 34 |
| MET | 12 | 11 |
| VAL | 42 | 43 |
| SER | 43 | 33[a] |
| PRO | 43 | 42 |
| THR | 44 | 38 |
| ALA | 47 | 50 |
| TYR | 27 | 27 |
| HIS | 19 | 21 |
| GLN | 13 | |
| GLU | 36 | ]51 |
| ASN | 32 | |
| ASP | 50 | ]84 |
| LYS | 35 | 38 |
| CYS | 13 | 12 |
| TRP | 10 | —[b] |
| ARG | 36 | 36 |
| GLY | 50 | 53 |

[a]Hydrolysis was performed for 24 h.
[b]Not determined.

The calculated molecular weight of the protein is 74 050 Dalton, which agrees well with the molecular weight of 74 kd of MOX, as determined on polyacrylamide/SDS gels.

Codon usage

In Table IV the codon usage for MOX is given. A bias towards the use of a selective number of codons is evident.

TABLE IV

| Comparison of preferred codon usage in S. cerevisiae, H. polymorpha and E. coli | | |
|---|---|---|
| | Hansenula | |
| Saccharomyces | MOX | E. coli |
| ALA | GCU, GCC | GCC | GCC not used, no clear pref. |
| SER | UCU, UCC | UCC, UCG | UCU, UCC |
| THR | ACU, ACC | ACC | ACU, ACC |
| VAL | GUU, GUC | GUA not used, no clear pref. | GUU, GUA |
| ILE | AUU, AUC | AUC, AUU | AUC |
| ASP | GAC | GAC | GAC |
| PHE | UUC | UUC | UUC |
| TYR | UAC | UAC | UAC |
| CYS | UGU | no clear pref. | no clear pref. |
| ASN | AAC | AAC | AAC |
| HIS | CAC | CAC | CAC |
| GLU | GAA | GAG | GAA |
| GLY | GGU | GGC practically not used, no clear pref. | GGU, GGC |
| GLN | CAA | CAG | CAG |
| LYS | AAG | AAG | AAA |
| PRO | CCA | CCU, CCA | CCG |
| LEU | UUG | CUG, CUC | CUG |
| ARG | AGA | AGA | CGU |

Example 2

CONSTRUCTION OF A PLASMID, pUR 3105, BY WHICH THE GENE CODING FOR NEOMYCIN PHOSPHOTRANSFERASE, THAT CONFERS RESISTANCE AGAINST THE ANTIBIOTIC G 418, IS INTEGRATED INTO THE CHROMOSOMAL MOX GENE UNDER CONTROL OF THE MOX PROMOTER AND OPERATOR REGION.

*H. polymorpha* cells, transformed with either the plasmids YEP 13, YRP 17, pHARS 1 or pHARS 2, were unstable and lost their leu+ or ura+ phenotype already after 10 generations upon growth under non-selective conditions. In order to obtain stable transformants and to test the MOX promoter, a plasmid pUR 3105 is constructed in which the neomycin phosphotransferase gene (NEO$^R$) is brought under direct control of the MOX promoter and operator region. The construction is made in such a way that the first ATG of the NEO$^R$ gene is coupled to 1.5 kb of the MOX promoter and operator region. The cloning of such a large promoter and operator region fragment is necessary as shorter fragments, that do not contain the −1000 region of the promoter and operator region, were less efficient.

The NEO$^R$ gene was isolated as a 1.1 kb XmaIII-SalI fragment from the transposon Tn5, situated from 35 bp downstream of the first ATG up to 240 bp downstream of the TGA translational stop codon. To avoid a complex ligation mixture, first pUR 3101 is constructed (FIG. 11A), which is a fusion of the far upstream SalI-XmaIII (position -1510 to position -1128) fragment of the MOX promoter and operator region, and the NEO$^R$ gene, subcloned on M13mp9. Another plasmid is constructed, pUR 3102, in which the 1.5 kb SalI-HgiAI fragment of the MOX gene, that covers nearly the whole MOX promoter and operator region, is ligated to a MOX-NEO$^R$ adapter (FIG. 11B) sequence and cloned in M13-mp9. The 1.2 kb XmaIII fragment of this plasmid is cloned into the XmaIII site of pUR 3101, resulting in pUR 3103, which is the exact fusion of the MOX promoter and operator region and the NEO$^R$ gene (FIG. 11C). The orientation is checked by cleavage with HgiAI and SalI. From the lambda-MOX-4 clone, a SalI-SacI fragment is subcloned that reaches from the SalI site, still in the structural MOX gene (position 894), up to the SacI site, far downstream of the structural MOX gene (position 3259) (see FIG. 9). This M13mp19 subclone is called pUR 3104. The plasmid pUR 3105 is obtained by the direct ligation of the 2.7 kb SalI fragment from pUR 3103 into the SalI site of pUR 3104. The orientation is tested by cleavage with SmaI and SacI.

After cleavage of this plasmid with HindIII and SacI and the transformation of this cleaved plasmid to *H. polymorpha*, G 418-resistant colonies are found that do not lose their resistance upon growth under nonselective conditions for a large number of generations.

Example 3

THE CONSTRUCTION OF pUR 3004, BY WHICH THE GENE CODING FOR D-AMINO ACID OXIDASE IS TRANSFERRED TO THE CHROMOSOME OF *H. POLYMORPHA* UNDER CONTROL OF THE MOX-PROMOTER AND OPERATOR REGION

D-amino acid oxidase (AAO) is an example of an oxido-reductase for the production of which the methylotrophic *H. polymorpha* is extremely suited. It might be expected that the enzyme, being an oxidase like MOX, is translocated to the peroxisomes of the yeast that are induced during growth on methanol or a mixture of methanol and a fermentable sugar as carbon source and D-amino acids as the sole nitrogen source. Under these conditions the cell will be protected from the $H_2O_2$ produced. Alternatively, AAO can be produced without the production of $H_2O_2$, when it is placed under control of the MOX- or DAS-promoter and operator region. The AAO production will be induced by the presence of methanol in the medium.

The amino acid sequence of the AAO enzyme has been published (Ronchi et al., 1982) and the complete gene is synthesised, using the phosphite technique (Matteuci and Caruthers, 1981). The gene is constructed in such a way that the optimal codon use for *H. polymorpha*, as derived from the sequence of the MOX gene, is used. Moreover, several unique restriction sites are introduced without changing the amino acid sequence, to facilitate subcloning during the synthesis. The DNA sequence is shown in FIG. 12. The gene is synthesised in oligonucleotides of about 50 nucleotides in length. Oligonucleotides are purified on 16% polyacrylamide gels. The oligonucleotides that form a subclone are added together in ligase buffer (Maniatis et al., 1982) and heated to 70° C. in a waterbath. The waterbath is slowly cooled to 16° C. and $T_4$-ligase is added. After two hours of ligation, the DNA is separated on a 1.5% agarose gel and the fragment, having the expected length, is isolated from the gel. It is subcloned in an M13mp18 vector cleaved at the respective restriction sites situated at the end of the fragment. The gene is subcloned in this way in 4 subclones, respectively SalI-HindIII (position 39–346), HindIII-XmaI (position 346–589), XmaI-KpnI (position 589–721) and KpnI-SalI (position 721–1044). The SalI-HindIII and HindIII-XmaI subclones and the XmaI-KpnI and Kpn-I-SalI subclones are ligated together as two SalI-XmaI subclones in SalI-XmaI cleaved M13mp18. These two subclones are ligated into a SalI cleaved M13mp8, resulting in pUR 3001 (FIGS. 12, 13A). The whole sequence is confirmed by the determination of the nucleotide sequence using the modified Sanger dideoxy sequencing technique (Biggin et al., 1983).

The construction of the integrative plasmid, containing the AAO gene is shown in FIG. 13A,B. The nearly complete AAO gene is placed upstream of the MOX termination region, by insertion of the AAO gene-containing SalI fragment of pUR 3001, in the unique SalI site of pUR 3104 (see also FIG. 13A), resulting in pUR 3002. The orientation is checked by cleavage with HindIII. The MOX promoter region is isolated as a 1.4 kb SalI-HgiAI fragment from pUR 3102 (FIG. 13A). This fragment is subsequently placed upstream of the AAO gene in pUR 3002, by ligation to partially SalI-digested pUR 3002 in the presence of the HgiAI-SalI MOX-AAO adapter, shown in FIG. 13A. The orientation of the resulting plasmid pUR 3003 is checked again by cleavage with HindIII. This plasmid is integrated into the MOX gene after cleavage with SacI and transformation to *H. polymorpha* cells. Transformants are selected by their ability to grow on D-amino acids as nitrogen source in the presence of methanol as inducer.

As the selection of cells containing the AAO gene is not simple, another selection marker is introduced. To this end, the *S. cerevisiae* LEU2 gene is integrated in between the structural AAO gene and the MOX terminator. For this construction, the plasmid pURS 528-03 is used. This plasmid is derived from pURY 528-03 described in European patent application 0096910. The construction is shown in FIG. 13C. The deleted carboxy terminal LEU2 gene sequence of pURY 528-03 was replaced by the complete carboxy terminal LEU2 gene sequence from pYeleu 10 (Ratzkin and Carbon, 1977) and the *E. coli* lac-lac regulon was eliminated. Subsequently the HpaI-SalI fragment of pURS 528-03 containing the LEU2 gene, is blunt end inserted in the SalI site of pUR 3003, situated in between the AAO structural gene and the MOX terminator. The orientation of the resulting plasmid pUR 3004 can be checked by cleavage with SalI and SacI. pUR 3004 integrates in the chromosomal MOX gene of *H. polymorpha* after transformation of the SacI-cleaved plasmid to a *H. polymorpha* leu− mutant. Selected leu+ transformants are integrated in the chromosomal MOX gene, together with the AAO gene.

Example 4

THE CONSTRUCTION OF pUR 3204, pUR 3205, pUR 3210 and pUR 3211, BY WHICH THE SMALL PEPTIDE HORMONE, THE HUMAN GROWTH RELEASING FACTOR, IS EXPRESSED UNDER CONTROL OF THE MOX-PROMOTER AND OPERATOR REGION, EITHER BY INTEGRATION INTO THE CHROMOSOMAL MOX GENE (pUR 3203, pUR 3204), OR BY INTEGRATION INTO A HARS1-CONTAINING PLASMID (pUR 3205) OR BY FUSION TO THE MOX STRUCTURAL GENE (pUR 3209, pUR 3210 and pUR 3211).

Human growth hormone releasing factor (HGRF) is a small, 44 amino acids long, peptide, that activates the secretion of human growth hormone from the pituitary glands. HGRF can be used in the diagnosis and treatment of pituitary dwarfism in man. Since HGRF has been shown to induce growth hormone stimulation in numerous species, HGRF might be used in the vetinary field too, by stimulating growth of animals and increase of milk production (Coude et al., 1984). It is difficult to obtain HGRF from human sources, but it could very well be produced by biotechnological processes, once the gene has been cloned and transferred to an appropriate host organism. Also, as a general example of the production of a peptide hormone by *H. polymorpha*, the gene for HGRF is synthesised in the optimal codon use of *H. polymorpha* and brought to expression in several ways.

For the construction of pUR 3204 and pUR 3205, the gene fragment that codes for the carboxy terminal part of the protein is synthesised in DNA oligomers of about 50 nucleotides in length and subcloned as a HindIII-SalI fragment in HindIII-SalI cleaved M13mp18, resulting in pUR 3201 (FIGS. 14, 15A). This HindIII-SalI fragment is subsequently inserted upstream of the MOX terminator in HindIII-SalI cleaved pUR 3104 (FIG. 15A), resulting in pUR 3202. The MOX promoter is inserted in front of the HGRF gene, by insertion of the SalI-HgiAI MOX-promoter fragment from pUR 3102 (FIG. 15A) in HindIII cleaved pUR 3202, using a HgiAI-HindIII adapter between the MOX-promoter and the HGRF gene (FIGS. 14, 15A). The orientation of the resulting plasmid pUR 3203 is checked by cleavage with SalI and HgiAI. pUR 3203 integrates into the chromosomal MOX gene of H. polymorpha after transformation of the SacI cleaved plasmid. Transformants are selected on immunological activity. pUR 3203 is cleaved with SalI, to insert the SalI-HpaI fragment of pURS 528-03 (FIG. 15B) that contains the LEU2 gene. The orientation of this gene in pUR 3204 is checked by cleavage with HindIII and EcoRI. pUR 3204 integrates into the chromosomal MOX gene of H. polymorpha after transformation of the SacI cleaved plasmid (FIG. 15B) to a leu− H. polymorpha mutant. Selection on on leu+ transformants. A plasmid, called pUR 3205, that replicates autonomously in .H. polymorpha and contains the HGRF gene, is obtained by insertion of the EcoRI, partially HindIII cleaved 4 kb long fragment of pUR 3203, containing the HGRF gene inserted in between the MOX-promoter and terminater, into partially HindIII-EcoRI cleaved pHARS1 (FIGS. 2, 15C). The construction of pUR 3205 is checked by cleavage with HindIII.

The production of small peptides as HGRF by microorganisms is often unstable as a result of enzymic degradation (Itakura et al., 1977). Fusion to a protein like MOX, and subsequent transport to the peroxisomes, could prevent degradation. Therefore, we decided to insert the HGRF gene into the unique KpnI site at position 1775 (amino acid 591, FIGS. 9, 10) of the MOX structural gene. The HGRF gene is synthesised again in DNA oligomers of 50 nucleotides in length, but now as two KpnI-HindIII subclones that are cloned as a complete HGRF structural gene in M13mp19, cleaved with KpnI (plasmid pUR 3206, FIGS. 16, 15D). Moreover, the ATG triplet coding for the internal methionine of HGRF at position 27 (Coude et al., 1984) (position 82 of the DNA sequence) is converted into a TGT triplet coding for cysteine. This does not alter the HGRF activity essentially, and facilitates the cleavage of HGRF from the fusion protein by CNBr cleavage (Itakura et al., 1977). From phage lambda MOX-4 (FIG. 19 SphI (position -491)-KpnI fragment is isolated and inserted into SphI-KpnI cleaved M13mp19. This results in pUR 3207. pUR 3206 is cleaved with KpnI and the HGRF gene is inserted into the KpnI site of pUR 3207, resulting in pUR 3208. The orientation is checked by direct sequence analysis on the single-stranded DNA of pUR 3208. Subsequently the downstream part of the MOX gene, from the unique KpnI site up to the SacI site, is isolated as a 1.5 kb fragment from phage lambda MOX-4 and inserted into SacI - partially KpnI cleaved pUR 3208. The orientation of the resulting plasmid pUR 3209 is checked by digestion with KpnI. pUR 3209 integrates into the chromosomal MOX gene of H. polymorpha after transformation of the SacI, SphI cleaved plasmid. Selection on immunological activity.

This MOX-HGRF fusion gene-is inserted into pHARS1 by isolation of the whole fusion gene from partially HindIII, partially EcoRI cleaved pUR 3209, into EcoRI partially HindIII cleaved pHARS1. This results in pUR 3210, which replicates in H. polymorpha after transformation (FIG. 15E). Alternatively, the LEU2-containing SalI-HpaI fragment of pURS 528-03 is inserted into the blunt-ended KpnI site of the HGRF gene, located at the carboxy terminus of the encoded protein, after partial KpnI cleavage of pUR 3209. The resulting plasmid pUR 3211 integrates into the chromosomal MOX gene of H. polymorpha, after transformation of the SacI, SphI cleaved plasmid (FIG. 15F).

Discussion

From the length of the open reading frame, from the similarity in the amino acid composition of purified MOX and the DNA derived protein sequence and from the identical 30 N-terminal amino acids, it is concluded that the complete gene for MOX from the yeast Hansenula polymorpha has been cloned. Its calculated molecular weight agrees well with the molecular weight determined on SDS polyacrylamide gels. Apart from the coding sequence, more than 1200 bp has been sequenced from both the 5'- and the 3'-non-coding regions, reaching from the SalI site upstream of the coding sequence, up to the SacI site downstream. The gene appears not to be interrupted with intervening sequences.

The protein is not transcribed in the form of a precursor. Based on the determination of the molecular weight, N-terminal signal sequences could not be detected in earlier studies of Roa and Blobel (1983) or Roggenkamp et al. (1984) as well. In similar studies, it was suggested that also the rat liver peroxisomal enzymes uricase (Goldman and Blobel, 1978) and catalase (Goldman and Blobel, 1978; Robbi and Lazarow, 1978) do not contain a cleavable N-terminal signal peptide. However, as discussed by these authors, proteolytic degradation could possibly explain the lack of the detection of such a signal sequence.

Our sequence results definitely prove that for translocation of this protein to the peroxisome, a cleavable N-terminal signal sequence is not required. Such a translocation signal may well be situated in the internal sequence of the mature protein, as is the case for ovalbumin (Lingappa et al., 1979). Inspection of the protein sequence reveals the amino acid sequence Gly X Gly Y Z Gly (amino acids 13–18), which is characteristic for FAD-(flavin adenine dinucleotide)-containing enzymes (Ronchi et al., 1981).

The isolation of the MOX gene described above gives a way how to determine the DNA sequence coding for MOX and the amino acid sequence of the MOX enzyme.

Similarly, the DNA sequences and amino acid sequences belonging to other oxidase-enzymes can be isolated and determined. The knowledge of the MOX gene sequence can be used to facilitate the isolation of genes coding for alcohol oxidases or even other oxidases. By comparing the properties and the structure of enzymes one can probably establish structure function and activity relationships. One can also apply methods as site-directed mutagenesis, or shortening or lengthening of the protein coding sequences, modifying the corresponding polypeptides, to select oxidase-enzymes with improved properties, e.g. with increased alkali stability, improved production, or oxidase-enzymes which need a substrate which is more compatible with detergent products.

Besides the isolation and characterization of the structural gene for MOX from the yeast H. polymorpha, also the isolation and characterization of the structural gene for DAS from the yeast H. polymorpha has been carried out in a similar way.

The DNA sequence of DAS is given in FIG. 17A–17C. A restriction map is given in FIG. 18. The amino acid composition calculated from the DNA sequence of DAS appeared to be in agreement with the amino acid composition determined after hydrolysis of purified DAS. The DAS enzyme catalyses the synthesis of dihydroxyacetone from formaldehyde and xylulose monophosphate. This reaction plays a crucial role in the methanol-assimilation process (cf. Veenhuis et al., 1983).

As described before, the synthesis of MOX and DAS is subject to glucose repression. It has now been found that higher levels of MOX are reached when using glucose/methanol mixtures as substrates instead of 0.5% (v/v) methanol. Under the former conditions up to 30% of the cellular protein consists of MOX, compared with up to 20% under the latter conditions.

It was considered that in the regulons of MOX and DAS sequences must exist that play a decisive role in the regulation of repression/derepression by glucose or of the induction by methanol. Some homology therefore might be expected.

A striking homology of the "TATA-boxes" has been found, both having the sequence CTATAAATA. No other homologies in the near upstream region of the MOX and DAS promoter and operator regions have been found. Unexpectedly, a detailed study of both promoter and operator regions has shown a remarkable homology of the promoter and operator regions for MOX and DAS in the region about 1000 bp upstream of the translation initiation codon. A practically complete consecutive region of 65 bp in the promoter and operator region of MOX is homologous to a 139 bp region in the DAS promoter and operator region, interspersed by several non-homologous regions (see FIG. 19). A similar homology is not found in any other region of both genes, that are over 4 kb in length including their upstream and downstream sequences. It is suggested that these homologous sequences play a role in the regulation of both genes by glucose and methanol. Transformation studies with vectors containing as regulon the first 500 bp upstream of the ATG of the structural gene of MOX, showed that this shortened MOX-promoter and operator region gave rise to a relatively low expression of the indicator gene beta-lactamase. Indicator genes are genes which provide the yeast with properties that can be scored easily, e.g. The gene for neomycin phosphotransferase giving resistance to the antibiotic G 418 (cf. Watson et al., 1983) or an auxotrophic marker such as leucin.

The fact that the far upstream homologous regions in the MOX and DAS genes have different interruptions and the fact that DAS is repressed at 0.1% glucose and MOX is not, suggest that these homologous regions are of importance to the repression-derepression by glucose and/or the induction of the expression in the presence of methanol. This assumption has been found correct indeed, and the presence or absence of these homologous regions can therefore be important for specific applications. For example, if the −1052 to −987 region of the MOX gene or the −1076 to −937 region of the DAS gene is important for the induction of MOX or DAS by methanol, the presence of these regions is required for the expression of MOX or DAS and/or for the induction of other enzymes by methanol. Another example might be the removal of the regions to avoid repression by glucose, which is needed for the expression of genes coding for proteins other than MOX and DAS under influence of the MOX and/or DAS regulatory regions with glucose as a carbon source.

Thus one aspect of the present invention relates to the isolation and complete characterization of the structural genes coding for MOX and DAS from the yeast *H. polymorpha*. It further relates to the isolation and complete characterization of the DNA sequences that regulate the biosynthesis of MOX and DAS in *H. polymorpha*, notably the promoter and operator regions and terminators.

Moreover, it relates to combinations of genes coding for alcohol oxidase or other oxidases originating from *H. polymorpha* strains other than *H. polymorpha* CBS 4732, or Hansenula species other than *H. polymorpha*, or yeast genera other than Hansenula, or moulds, or higher eukaryotes, with the powerful promoter and operator regions and terminator of the MOX gene from *H. polymorpha* CBS 4732. These combinations may be located on vectors carrying amongst others an autonomously replicating sequence originating from *H. polymorpha* or related species or minichromosomes containing centromers, and optionally selection marker(s) and telomers. These combinations may also be integrated in the chromosomal DNA of *H. polymorpha*.

Furthermore it relates to combinations of the powerful regulon or parts of it and terminators of the MOX and/or DAS and—by site-directed mutagenesis or other methods—changed structural genes coding for alcohol oxidase or another oxidase. These changed structural genes may be located on episomal vectors, in minichromosomes or integrated in the chromosomes of *H. polymorpha*, *H. wingeii*, *H. anomala*, and *S. cerevisiae* or in other yeasts.

Besides this, the present invention relates to combinations of the regulon and terminators of the MOX and/or DAS gene of *H. polymorpha* with structural genes coding for other proteins than oxidases.

A very important and preferred embodiment of the invention is a process for preparing a polypeptide, such as a protein or an enzyme, by culturing a microorganism under suitable conditions, optionally concentrating the polypeptide and collecting same in a manner known per se, characterized in that a microorganism is used that has been obtained by recombinant DNA technology and carries a structural gene coding for the polypeptide concerned, the expression of which is under the control of a promoter and operator region, comprising a promoter and at least either the −1052 to −987 region of the MOX gene of *Hansenula polymorpha* CBS 4732, or the −1076 to −937 region of the DAS gene of *Hansenula polymorpha* CBS 4732, or a corresponding region of other methylotrophic moulds or yeasts, or an effective modification of any of these regions.

Surprisingly, it has been observed by the present inventors that the regions concerned, which are shown in FIG. 20 and are referred to herein as the −1000 regions of the MOX and DAS genes, are of crucial importance for the expression of the structural gene concerned. Experiments performed with recombinants containing the MOX regulon from which this region was eliminated showed a low level of expression. Therefore, use of a promoter and operator region comprising such −1000 region, or an effective modification thereof, i.e. any modification which does not result in a significant mutilation of the function of said region, makes it possible to realize production of a relatively high amount of the desired polypeptide.

A preferred embodiment of this process according to the invention is characterized in that the structural gene concerned has been provided with one or more DNA sequences coding for amino acid sequences involved in the translocation of the gene product into the peroxisomes or equivalent microbodies of the microbial host. Translocation of the produced polypeptide into the peroxisomes or equivalent microbodies improves their stability, which results in a higher yield. For certain kinds of polypeptides, in particular oxidases, such translocation is imperative for survival of the microbial host, i.e. to protect the host against the toxic effects of the hydrogen peroxide produced when the microbial host cells are growing on the substrate of the oxidase. If the oxidase concerned does not contain addressing signals which are functional in the microbial host used in the production process, one should provide the structural gene with sequences coding for host specific addressing signals, for example by adding such sequences or by substituting these for the original addressing sequences of the gene. Production of a fused polypeptide, in which the fusion partner carries suitable addressing signals, is another possibility. In case methylotrophic yeasts are used in the production process, it is preferred that the DNA sequences consist of the MOX gene or those parts thereof which are responsible for MOX translocation into the peroxisomes or microbodies.

Finally, this aspect of the present invention is related to the synthesis of MOX originating from *H. polymorpha* in other yeasts.

Some microorganisms with the potential of producing alcohol oxidases are summarized below.

Yeasts producing alcohol oxidases
(Taxonomic division according to Lee and Komagata, 1980)

| Group 1 | *Candida boidinii* |
|---|---|
| Group 2a | *Hansenula philodendra* |
| | *Pichia lindnerii* |
| | *Torulopsis nemodendra* |
| | *Torulopsis pinus* |
| | *Torulopsis sonorensis* |
| Group 2b | *Candida cariosilignicola* |
| | *Hansenula glucozyma* |
| | *Hansenula henricii* |
| | *Hansenula minuta* |
| | *Hansenula nonfermentans* |
| | *Hansenula polymorpha* |
| | *Hansenula wickerhamii* |
| | *Pichia pinus* |
| | *Pichia trehalophila* |
| Group 2c | *Candida succiphila* |
| | *Torulopsis nitratophila* |
| Group 3 | *Pichia cellobiosa* |
| Group 4 | *Hansenula capsulata* |
| | *Pichia pastoris* |
| | *Torulopsis molischiana* |

Moulds producing alcohol oxidases:
*Lenzites trabea*
*Polyporus versicolor*
*Polyporus obtusus*
*Poria contigua*

Among the oxidases other than alcohol oxidases, the most interesting are:
glycerol oxidase,
aldehyde oxidase,
amine oxidase,
aryl-alcohol oxidase,
amino acid oxidase,
glucose oxidase,
galactose oxidase,
sorbose oxidase,
uric acid oxidase,
chloroperoxidase, and
xanthine oxidase.

Combinations of the powerful promoter and operator region and terminators of the MOX and DAS genes from *H. polymorpha* and structural genes for oxidases may be combined with one or more DNA sequences that enable replication of the structural gene in a particular host organism or group of host organisms, for example autonomously replicating sequences or centromers (and telomers) originating from *H. polymorpha*, to suitable vectors that may be transferred into *H. polymorpha* and related yeasts or other microorganisms.

*H. polymorpha* mutants LEU-1 and LR9, mentioned on page 12 of this specification, were deposited at the Centraalbureau voor Schimmelcultures at Delft on 15th Jul., 1985, under numbers CBS 7171 and CBS 7172, respectively.

The above description is followed by a list of references, claims and Figures.

References

1. GB-PS 1 225 713 (Colgate-Palmolive Company; publ. 24th Mar. 1971; priority date 19th Apr. 1968).
2. DE-PA 2 557 623 (Henkel & Cie GmbH; publ. 30th Jun. 1977; priority date 20th Dec. 1975).
3. GB-PA 2 101 167 (Unilever PLC; publ. 12th Jan. 1983; priority date 7th Jul. 1981).
4. van Dijken, J.P., Otto, R. and Harder, W. (1976), Arch.Microb. 111, 137–144.
5. Veenhuis, M., van Dijken, J.P. and Harder, W. (1983) in Advances in Microbial Physiology, Rose, A.H., Gareth Morris, J. and Tempest, D.W., Eds, Vol. 24, pp 1–82, Academic Press, New York.
6. Roggenkamp, R., Janowicz, Z., Stanikowski Hollenberg, C.P. (1984), Mol.Gen.Genet. 194, 489–493.
7. Sahm, H. (1977) in Advances in Microbiol. Engineering, Ghose, T.K., Fiechter, A. and Blakebrough, N., Eds, Vol. 6, pp 77–103, Springer-Verlag, Berlin.
8. Bystrykh, L.V., Sokolov, A.P. and Trotsenko, Y.A. (1981), FEBS Letters 132, 324–328.
9. Roa, M. and Blobel, G. (1983), Proc.Natl.Acad.Sci. USA, 80, 6872–6876.
10. Veenhuis, M., van Dijken, J.P., Pilon, S.A.F. and Harder, W. (1978), Arch.Microbiol. 117, 1953–163.
11. Loenen, W.A.M. and Brammar, W.J. (1980), Gene 20, 249–259.
12. Hohn, B. (1979) in Methods in Enzymology, Wu, R., Ed., Vol. 68, pp 299–309, Academic Press, New York.
13. Edens, L., Heslinga, L., Klok, R., Ledeboer, A.M., Maat, J., Toonen, M.Y., Visser, C. and Verrips, C.T. (1982), Gene 18, 1–12.
14. Pelham, H.R.B. and Jackson, R.J. (1976), Eur.J. Biochem. 67, 247–257.
15. Valerio, D., Duyvensteijn, M.G.C., Meera Khan, P., Geurts van Kessel, A., de Waard, A. and van der Eb, A.J. (1983), Gene 25, 231–240.
16. Ledeboer, A.M., Verrips, C.T. and Dekker, B.M.M. (1984), Gene 30, 23–32.
17. Maniatis, T., Fritsch, E.F. and Sambrook, J. (1982), Molecular Cloning, p 278, Cold Spring Harbor Laboratory Publ., New York.

18. Benton, W.D. and Davis, R.W. (1977), Science 196, 180-182.
19. Ambler, R.P. (1972), Methods in Enzymology, Vol. 25, pp 262-272, Academic Press, New York.
20. Matteucci, M.D. and Caruthers, M.H. (1981), J.Am. Chem.Soc. 103, 3185-3191.
21. Wallace, R.B., Johnson, M.J., Hirose, T., Miyake, T., Kawashima, E.H. and Itakura, K. (1981), Nucl. Acids Res. 9, 879-894.
22. Biggin, M.D., Gibson, T.J. and Hong, G.F. (1983), Proc.Natl.Acad.Sci.USA 80, 3963-3965.
23. Gleeson, M.A., Waites, M.J. and Sudbery, P.E. (1984), in: Microbial growth on C1 compounds, Eds. Crawford, R.L. and Hanson, R.S., Publ. A.S.M., Washington, 228-235.
24. Fink, G.D. (1970), Methods in Enzymology, Tabor, H. and Tabor, C.W., Eds., Vol. 17, pp 59-78, Academic Press, New York.
25. Boeke, J.D., LaCroute, F. and Fink, G.D. (1984), Mol. Gen.Genet. 197, 345-346.
26. Jones, E.W. and Fink, G.D. (1982), Cold Spring Harbour Monogr.Ser., 11B, 181-299.
27. Lieberman, I., Kornberg, A. and Simms, E.S. (1955), J.Biol.Chem. 215, 403-415.
28. Stinchcomb, D.T., Thomas, M., Kelly, J., Selker, E. and Davis, R.W. (1980), Proc.Natl.Acad.Sci.USA 77, 4559-4563.
29. Stinchcomb, D.T., Mann, C. and Davis, R.W. (1982), J.Mol.Biol. 158. 157-179.
30. Struhl, K., Stinchcomb, D.T., Scherer, S. and Davis, R.W. (1979), Proc.Natl.Acad.Sci.USA 76. 1035-1039.
31. Carlson, M. and Botstein, D. (1982), Cell 28, 145-154.
32. Beggs, J.D. (1978), Nature 275, 104-109.
33. Broach, J.R., Strathern, J.N. and Hicks, J.B. (1979). Gene 8, 121-133.
34. Das, S., Kellerman, E. and Hollenberg, C.P. (1984), J.Bacteriol. 158, 1165-1167.
35. Ito, H., Fukuda, Y., Murata, K. and Kimura, A. (1983), J.Bacteriol. 153, 163-168.
36. Klebe, R.J., Harriss, J.V., Sharp, Z.D. and Douglas, M.G. (1983), Gene 25, 333-341.
37. Hollenberg, C.P. (1982), Curr.Top.Microbiol.Immunol. 96, 119-144.
38. Kato, N., Omori, Y., Tani, Y. and Ogata, K. (1976), Eur.J.Biochem. 64, 341-350.
39. Schütte, H., Flossdorf, J., Sahm, H. and Kula, M.R., (1976), Eur.J.Biochem. 62, 151-160.
40. Ronchi, S., Minchiotti, L., Galliano, M., Curti, B., Swenson, R.P., Williams, C.H. and Massey, V. (1982), J.Biol.Chem. 257, 8824-8834.
41. Ratzkin, B. and Carbon, J. (1977), Proc.Natl.Acad. Sci.USA 74, 487-491.
42. Coude, F.X., Diaz, J., Morre, M., Roskam, W. and Roncucci, R. (1984), Trends in Biotechnology 2, 83-88.
43. Itakura, K., Hirose, T., Crea, R., Riggs, A.D., Heyneker, H.L., Bolivar, F. and Boyer, H.W. (1977), Science 198. 1056-1063.
44. Goldman, B.M. and Blobel, G. (1978), Proc.Natl. Acad.Sci.USA 75, 5066-5070.
45. Robbi, M. and Lazarow, P.B. (1978), Proc.Natl.Acad. Sci.USA 75, 4344-4348.
46. Lingappa, V.R., Lingappa, J.R. and Blobel, G. (1979), Nature 281, 117-121.
47. Watson, J.D., Tooze, J. and Kurtz, D.T. (1983), Recombinant DNA, A Short Course, page 178, published by W.H. Freeman and Company, New York.
48. Lee, J.D. and Komagata, K. (1980), J.Gen.Appl. Microbiol. 26, 133-158.

We claim:

1. DNA segment for transforming a microbial host to produce a protein, comprising a promoter and operator region operably linked to a heterologous structural gene coding for said protein wherein said promoter and operator region is selected from the group consisting of the promoter and operator region of nucleotides −1 to about −1500 of the methanol oxidase gene given in FIG. 10, the promoter and operator region of nucleotides −1 to about −2125 of the DAS gene given in FIG. 17.

2. DNA segment according to claim 1 further comprising a terminator selected from the group consisting of the terminator designated 1993 to about 3260 in FIGS. 10, the terminator designated 2110 to about 2350 in FIG. 17.

3. A microbial yeast cell of the genus Hansenula, transformed with the DNA segment of claim 1.

4. A microbial yeast cell of the genus Saccharomyces transformed with the DNA segment of claim 1.

* * * * *